(12) United States Patent
Gaudernack et al.

(10) Patent No.: US 7,192,927 B2
(45) Date of Patent: Mar. 20, 2007

(54) PEPTIDES

(75) Inventors: Gustav Gaudernack, Sandvika (NO); Jon Amund Eriksen, Porsgrunn (NO); Mona Moller, Porsgrunn (NO); Marianne Klemp Gjertsen, Snaroya (NO); Ingvil Saeterdal, Oslo (NO)

(73) Assignee: Gemvax AS, Oslo (NO)

( * ) Notice: Subject to any disclaimer, the term of this patent is extended or adjusted under 35 U.S.C. 154(b) by 359 days.

(21) Appl. No.: 10/776,224

(22) Filed: Feb. 12, 2004

(65) Prior Publication Data

US 2005/0074849 A1 Apr. 7, 2005

Related U.S. Application Data

(62) Division of application No. 09/674,973, filed as application No. PCT/NO92/00032 on May 3, 1999, now Pat. No. 6,759,046.

(30) Foreign Application Priority Data

May 8, 1998 (NO) .................................. 19982097

(51) Int. Cl.
- A61K 38/10 (2006.01)
- A61K 38/16 (2006.01)
- C07K 7/08 (2006.01)
- C07K 14/00 (2006.01)

(52) U.S. Cl. .................. 514/13; 514/12; 530/324; 530/326; 424/278.1

(58) Field of Classification Search .................. 514/12, 514/13; 530/324, 326; 424/278.1
See application file for complete search history.

(56) References Cited

U.S. PATENT DOCUMENTS 5,856,171 A * 1/1999 Korsmeyer ............... 435/254.2

FOREIGN PATENT DOCUMENTS

| WO | WO 92/14756 | 9/1992 |
|----|-------------|--------|
| WO | WO 95/32731 | 12/1995 |
| WO | WO 96/18409 | 6/1996 |
| WO | WO 97/12992 | 4/1997 |
| WO | WO 99/10382 | 3/1999 |
| WO | WO 99/58564 | 11/1999 |

OTHER PUBLICATIONS

Rampino et al. (1997), Science 275:967-969, "Somatic Frameshift Mutations in the BAX Gen in Colon Cancers of the Microsatellite Mutator Pheotype".
Yamamoto et al. (Mar. 1998), Cancer Research 58:997-1003, "Somatic Frameshift Mutations in DNA Mismatch Repair and Proapoptosis Genes in Hereditary Nonpolyposis Colorectal Cancer".

(Continued)

Primary Examiner—Michael Borin
(74) Attorney, Agent, or Firm—Fitzpatrick, Cella, Harper & Scinto

(57) ABSTRACT

Isolated peptides that are fragments of protein products arising from frameshift mutations in genes associated with cancer are disclosed. The isolated peptides of the invention are capable of eliciting T cell immunity against cells harboring genes with such frameshift mutations. Cancer vaccines and therapeutically effective compositions containing the peptides of the invention are also described.

12 Claims, 14 Drawing Sheets

OTHER PUBLICATIONS

Markowitz et al. (1995), Science 268:1336-1338, "Inactivation of the Type II TGF-β Receptor in Colon Cancer Cells with Microsatellite Instability".

Gaudernack (1996), Immunotechnology 2:3-9, "T cell responses against mutant *ras*: a basis for novel cancer vaccines".

Gjertsen et al. (1996), Int. Journal of Cancer 65:450-453, "*Ex Vivo* ras Peptide Vaccination in Patients with Advanced Pancreatic Cancer: Results of a Phase I/II Study".

Gjertsen et al. (1996), British Journal of Cancer 74:1828-1833, "Characterisation of immune responses in pancreatic carcinoma patients after mutant p21 ras peptide vaccination".

Gjertsen et al. (1997), Int. J. Cancer 72:784-790, "Cytotoxic CD4+and CD8+T-Lymphocyt s, Generated by Mutant p21-*ras* (12Val) Peptide Vaccination of a Patient, Recognize . . . Tumour Cells Carrying This Mutation".

Gjertsen et al. (1998) Vox Sanguinis 74(suppl. 2): 489-495, "Mutated Ras Peptides as Vaccines in Immunotherapy of Cancer".

Barinaga, (1992) Science, vol. 257, pp. 880-881, "Getting Some Backbone: How MHC Binds Peptides".

Deres et al., (1989) Nature, vol. 342, pp. 561-564, "*In vivo* priming of virus-specific cytotoxic T lymphocytes with synthetic lipopeptide vaccine".

Tighe et al., (1998) Immun. Today, vol. 19(2), pp. 89-97, "Gene vaccination: plasmid DNA is more than just a blueprint".

* cited by examiner

PEPTIDES

This application is a divisional application of application Ser. No. 09/674,973, filed on Jun. 4, 2001, now U.S. Pat. No. 6,759,046 which was filed as PCT/NO92/00032 filed on May 3, 1999.

SUMMARY OF THE INVENTION

This invention relates to peptides which are fragments of protein products arising from frameshift mutations in genes, which peptides elicit T cellular immunity, and to cancer vaccines and compositions for anticancer treatment comprising said peptides.

The invention further relates to a method for identifying such peptides which are fragments of protein products arising from frameshift mutations in genes, which may elicit T cellular immunity which is useful for combating cancer associated with said mutated genes.

The invention also relates to DNA sequences encoding at least one frameshift mutant peptide, and vectors comprising at least one insertion site containing a DNA sequence encoding at least one frameshift mutant peptide.

Further the invention relates to methods for the treatment or prophylaxis of cancers associated with frameshift mutations in genes by administration of at least one frameshift mutant peptide or a recombinant virus vector comprising at least one insertion site containing a DNA sequence encoding at least one frameshift mutant peptide, or an isolated DNA sequence comprising a DNA sequence encoding at least one frameshift mutant peptide.

The present invention represents a further development of anticancer treatment or prophylaxis based on the use of peptides to generate activation and strengthening of the anti cancer activity of the T cellular arm of the body's own immune system.

TECHNICAL BACKGROUND

Tumour Antigens, Status:

T cell defined antigens have now been characterised in a broad spectrum of cancer types. These antigens can be divided into several main groups, depending on their expression. The two main groups are constituted by developmental differentiation related antigens (tumour-testis antigens, oncofoetal antigens etc., such as MAGE antigens and CEA) and tissue specific differentiation antigens (Tyrosinase, gp100 etc.). The group containing the truly tumour specific antigens contains proteins that are altered due to mutations in the genes encoding them. In the majority of these, the mutations are unique and have been detected in a single or in a small number of tumours. Several of these antigens seem to play a role in oncogenesis.

Cancer Vaccines, Status:

The focus in cancer vaccine development has been on antigens expressed in a high degree within one form of cancer (such as melanoma) or in many kinds of cancers. One reason for this is the increased recruitment of patients into clinical protocols. The field is in rapid growth, illustrated by the accompanying table listing the cancer vaccine protocols currently registered in the PDQ database of NCI.

Inheritable Cancer/Cancer Gene Testing:

Inherited forms of cancer occur at a certain frequency in the population. For several of these cancer forms, the underlying genetic defects have been mapped. This is also the case in Lynch syndrome cancers which constitute an important group of inheritable cancer. In families inflicted with this syndrome, family members inherit defect genes encoding DNA Mismatch Repair (MMR) Enzymes. Carriers of such MMR defects frequently develop colorectal cancer (HNPCC) and other forms of cancer (list?). Mutations in MMR enzymes can be detected using gene testing in the same way as other cancer related genes can be detected.

Gene testing of risk groups in this case represents an ethical dilemma, since no acceptable forms for prophylactic treatment exist. At present surgery to remove the organ in danger to develop cancer has been the only treatment option. In these patients, cancer vaccines will be a very (interesting) form of prophylaxis, provided efficient vaccines can be developed.

The lack of efficient repair of mismatched DNA results in deletions and insertions in one strand of DNA, and this happens preferentially in stretches of DNA containing repeated units (repeat sequences). Until now, focus has been on repeat sequences in the form of non-coding microsattelite loci. Indeed microsattelite instability is the hallmark of cancers resulting from MMR defects. We have taken another approach, and have concentrated on frameshift mutations occurring in DNA sequences coding for proteins related to the oncogenic process. Such frameshift mutations result in completely new amino acid sequences in the C-terminal part of the proteins, prematurely terminating where a novel stop codon appears. This results in two important consequences:

1) The truncated protein resulting from the frameshift is generally nonfunctional, in most cases resulting in "knocking out" of an important cellular function. Aberrant proteins may also gain new functions such as the capacity to aggragate and form plaques. In both cases the frameshift results in disease.

2) The short new C-terminal amino acid sequence resulting from the shift in the reading frame (the "frameshift sequence") is foreign to the body. It does not exist prior to the mutation, and it only exists in cells having the mutation, i.e. in tumour cells and their pre malignant progenitors. Since they are completely novel and therefore foreign to the immune system of the carrier, they may be recognised by T-cells in the repertoire of the carrier. So far, nobody has focused on this aspect of frameshift mutations, and no reports exist on the characterisation of frameshift peptides from coding regions of proteins as tumour antigens. This concept is therefore novel and forms the basis for developing vaccines based on these sequences. It follows that such vaccines may also be used prophyllactively in persons who inherit defective enzymes belonging to the MMR machinery. Such vaccines will therefore fill an empty space in the therapeutic armament against inherited forms of cancer.

It has been shown that single amino acid substitutions in intracellular "self"-proteins may give rise to tumour rejection antigens, consisting of peptides differing in their amino acid sequence from the normal peptide. The T cells which recognise these peptides in the context of the major histocompatibility (MHC) molecules on the surface of the tumour cells, are capable of killing the tumour cells and thus rejecting the tumour from the host.

In contrast to antibodies produced by the B cells, which typically recognise a free antigen in its native conformation and further potentially recognise almost any site exposed on the antigen surface, T cells recognise an antigen only if the antigen is bound and presented by a MHC molecule. Usually this binding will take place only after appropriate antigen processing, which comprises a proteolytic fragmentation of the protein, so that the resulting peptide fragment fits into the groove of the MHC molecule. Thereby T cells are enabled to also recognise peptides derived from intracellular proteins. T cells can thus recognise aberrant peptides derived from anywhere in the tumour cell, in the context of MHC molecules on the surface of the tumour cell, and can subsequently be activated to eliminate the tumour cell harbouring the aberrant peptide.

M. Barinaga, Science, 257, 880–881, 1992 offers a short review of how MHC binds peptides. A more comprehensive explanation of the Technical Background for this Invention may be found in D. Male et al, Advanced Immunology, 1987, J.B.lippincott Company, Philadelphia. Both references are hereby included in their entirety.

The MHC molecules in humans are normally referred to as HLA (human leukocyte antigen) molecules. They are encoded by the HLA region on the human chromosome No 6.

The HLA molecules appear as two distinct classes depending on which region of the chromosome they are encoded by and which T cell subpopulations they interact with and thereby activate primarily. The class I molecules are encoded by the HLA A, B and C subloci and they primarily activate CD8+ cytotoxic T cells. The HLA class II molecules are encoded by the DR, DP and DQ subloci and primarily activate CD4+ T cells, both helper cells and cytotoxic cells.

Normally every individual has six HLA Class I molecules, usually two from each of the three groups A, B and C. Correspondingly, all individuals have their own selection of HLA Class II molecules, again two from each of the three groups DP, DQ and DR. Each of the groups A, B, C and DP, DQ and DR are again divided into several subgroups. In some cases the number of different HLA Class I or II molecules is reduced due to the overlap of two HLA subgroups.

All the gene products are highly polymorphic. Different individuals thus express distinct HLA molecules that differ from those of other individuals. This is the basis for the difficulties in finding HLA matched organ donors in transplantations. The significance of the genetic variation of the HLA molecules in immunobiology is reflected by their role as immune-response genes. Through their peptide binding capacity, the presence or absence of certain HLA molecules governs the capacity of an individual to respond to peptide epitopes. As a consequence, HLA molecules determine resistance or susceptibility to disease.

T cells may control the development and growth of cancer by a variety of mechanisms. Cytotoxic T cells, both HLA class I restricted CD8+ and HLA Class II restricted CD4+, may directly kill tumour cells carrying the appropriate tumour antigens. CD4+ helper T cells are needed for cytotoxic CD8+ T cell responses as well as for antibody responses, and for inducing macrophage and LAK cell killing.

A requirement for both HLA class I and II binding is that the peptides must contain a binding motif, which usually is different for different HLA groups and subgroups. A binding motif is characterised by the requirement for amino acids of a certain type, for instance the ones carrying large and hydrophobic or positively charged side groups, in definite positions of the peptide so that a narrow fit with the pockets of the HLA binding groove is achieved. The result of this, taken together with the peptide length restriction of 8–10 amino acids within the binding groove, is that it is quite unlikely that a peptide binding to one type of HLA class I molecules will also bind to another type. Thus, for example, it may very well be that the peptide binding motif for the HLA-A1 and HLA-A2 subgroups, which both belong to the class I gender, are as different as the motifs for the HLA-A1 and HLA-B1 molecules.

For the same reasons it is not likely that exactly the same sequence of amino acids will be located in the binding groove of the different class II molecules. In the case of HLA class II molecules the binding sequences of peptides may be longer, and it has been found that they usually contain from 10 to 16 amino acids, some of which, at one or both terminals, are not a part of the binding motif for the HLA groove.

However, an overlap of the different peptide binding motifs of several HLA class I and class II molecules may occur. Peptides that have an overlap in the binding sequences for at least two different HLA molecules are said to contain "nested T cell epitopes". The various epitopes contained in a "nested epitope peptide" may be formed by processing of the peptide by antigen presenting cells and thereafter be presented to T cells bound to different HLA molecules. The individual variety of HLA molecules in humans makes peptides containing nested epitopes more useful as general vaccines than peptides that are only capable of binding to one type of HLA molecule.

Effective vaccination of an individual can only be achieved if at least one type of HLA class I and/or II molecule in the patient can bind a vaccine peptide either in it's full length or as processed and trimmed by the patient's own antigen presenting cells.

The usefulness of a peptide as a general vaccine for the majority of the population increases with the number of different HLA molecules it can bind to, either in its full length or after processing by antigen presenting cells.

In order to use peptides derived from a protein encoded by a mutated gene as vaccines or anticancer agents to generate anti tumour CD4+ and/or CD8+ T cells, it is necessary to investigate the mutant protein in question and identify peptides that are capable, eventually after processing to shorter peptides by the antigen presenting cells, to stimulate T cells.

PRIOR ART

In our International Application PCT/NO92/00032 (published as WO92/14756), the content of which is herein incorporated by reference, we described synthetic peptides and fragments of oncogene protein products which have a point of mutation or translocations as compared to their proto-oncogene or tumour suppressor gene protein. These peptides correspond to, completely cover or are fragments of the processed oncogene protein fragment or tumour suppressor gene fragment as presented by cancer cells or other antigen presenting cells, and are presented as a HLA-peptide complex by at least one allele in every individual. These peptides were also shown to induce specific T cell responses to the actual oncogene protein fragment produced by the cell by processing and presented in the HLA molecule. In particular, we described peptides derived from the P21 ras protein which had point mutations at particular amino acid positions, namely position 12, 13 and 61. These peptides have been shown to be effective in regulating the growth of cancer cells in vitro. Furthermore, the peptides were shown to elicit CD4+ T cell immunity against cancer cells harbouring the mutated P21 ras oncogene protein through the administration of such peptides in vaccination or cancer therapy schemes. Later we have shown that these peptides also elicit CD8+ T cell immunity against cancer cells harbouring the mutated P21 ras onco gene protein through the administration mentioned above.

However, the peptides described above will be useful only in certain number of cancers, namely those which involve oncogenes with point mutations or translocation in a proto-oncogene or tumour suppressor gene. There is therefore a strong need for an anticancer treatment or vaccine which will be effective against a more general range of cancers.

In general, tumors are very heterogenous with respect to genetic alterations found in the tumour cells. This implies that both the potential therapeutic effect and prophylactic strength of a cancer vaccine will increase with the number of targets that the vaccine is able to elicit T cell immunity against. A multiple target vaccine will also reduce the risk of new tumour formation by treatment escape variants from the primary tumour.

DEFINITION OF PROBLEM SOLVED BY THE INVENTION

There is a continuing need for new anticancer agents based on antigenic peptides giving rise to specific T cellular responses and toxicity against tumours and cancer cells carrying genes with mutations related to cancer. The present invention will contribute largely to supply new peptides that can have a use in the combat and prevention of cancer as ingredients in a multiple target anti-cancer vaccine.

Another problem solved by the present invention is that a protection or treatment can be offered to the individuals belonging to family's or groups with high risk for hereditary cancers. Hereditary cancers are in many cases associated with genes susceptible to frameshift mutations as described in this invention (i.e. mutations in mismatch repair genes). Today it is possible to diagnose risk of getting hereditary cancer but no pharmaceutical method for protection against the onset of the cancer is available.

DEFINITION OF THE INVENTION

A main object of the invention is to obtain peptides corresponding to peptide fragments of mutant proteins produced by cancer cells which can be used to stimulate T cells.

Another main object of the invention is to develop a cancer therapy for cancers based on the T cell immunity which may be induced in patients by stimulating their T cells either in vivo or in vitro with the peptides according to the invention.

A third main object of the invention is to develop a vaccine to prevent the establishment of or to eradicate cancers based solely or partly on peptides corresponding to peptides of the present invention which can be used to generate and activate T cells which produce cytotoxic T cell immunity against cells harbouring the mutated genes.

A fourth main object of the invention is to design an anticancer treatment or prophylaxis specifically adapted to a human individual in need of such treatment or prophylaxis, which comprises administering at least one peptide according to this invention.

These and other objects of the invention are achieved by the attached claims.

Since frameshift mutations result in premature stop codons and therefore deletion in large parts of the proteins, proteins with frameshift mutations have generally not been considered to be immunogenetic and have therefore not been considered as targets for immunotherapy. Thus it has now surprisingly been found that a whole group of new peptides resulting from frameshift mutations in tumour relevant genes are useful for eliciting T cell responses against cancer cells harbouring genes with such frameshift mutations.

Genes containing a mono nucleoside base repeat sequence of at least five residues, for example of eighth deoxyadenosine bases (AAAAAAA), or a di-nucleoside base repeat sequence of at least four di-nucleoside base units, for example of two deoxyadenosine-deoxycytosine units (ACAC), are susceptible to frameshift mutations. The frameshift mutations occur, respectively, either by insertion of one or two of the mono-nucleoside base residue or of one or two of the di-nucleoside base unit in the repeat sequence, or by deletion of one or two of the mono-nucleoside base residue or of one or two of the di-nucleoside base unit from the repeat sequence. A gene with a frameshift mutation will from the point of mutation code for a protein with a new and totally different amino acid sequence as compared to the normal gene product. This mutant protein with the new amino acid sequence at the carboxy end will be specific for all cells carrying the modified gene.

In the remainder of this specification and claims the denomination frameshift mutant peptides will comprise such proteins and peptide fragments thereof.

It has now according to the present invention been found that such new protein sequences arising from frameshift mutations in genes in cancer cells give rise to tumour rejection antigens that are recognised by T cells in the context of HLA molecules.

It has further according to the present invention been found a group of peptides corresponding to fragments of mutant proteins arising from frameshift mutations in genes in cancer cells which can be used to generate T cells. The said peptides can therefore also be used to rise a T cell activation against cancer cells harbouring a gene with a frameshift mutation as described above.

These peptides are at least 8 amino acids long and correspond, either in their full length or after processing by antigen presenting cells, to the mutant gene products or fragments thereof produced by cancer cells in a human patient afflicted with cancer.

A peptide according to this invention is characterised in that it a) is at least 8 amino acids long and is a fragment of a mutant protein arising from a frameshift mutation in a gene of a cancer cell; and b) consists of at least one amino acid of the mutant part of a protein sequence encoded by said gene; and c) comprises 0–10 amino acids from the carboxyl terminus of the normal part of the protein sequence preceding the amino terminus of the mutant sequence and may further extend to the carboxyl terminus of the mutant part of the protein as determined by a new stop codon generated by the frameshift mutation in the gene; and d) induces, either in its full length or after processing by antigen presenting cell, T cell responses.

The peptides of this invention contain preferably 8–25, 9–20, 9–16, 8–12 or 20–25 amino acids. They may for instance contain 9, 12, 13, 16 or 21 amino acids.

It is most preferred that the peptides of the present invention are at least 9 amino acids long, for instance 9–18 amino acids long, but due to the processing possibility of the antigen presenting cells also longer peptides are very suitable for the present invention. Thus the whole mutant amino acid sequence may be used as a frameshift mutant peptide according to the present invention, if it comprises 8 amino acids or more.

The invention further relates to a method for vaccination of a person disposed for cancer, associated with a frameshift mutation in a gene, consisting of administering at least one peptide of the invention one or more times in an amount sufficient for induction of T-cell immunity to the mutant proteins encoded by the frameshift mutated gene.

The invention also relates to a method for treatment of a patient afflicted with cancer associated with frameshift mutation in genes, consisting of administering at least one peptide of the invention one or more times in an amount sufficient for induction of T-cell immunity to mutant proteins arising from frameshift mutations in the genes of cancer cells.

Furthermore, it has according to the present invention been found a method for identifying new peptides which correspond to fragments of proteins arising from frameshift mutations in genes. This method is characterised by the following steps:

1) identifying a gene in a cancer cell susceptible to frameshift mutation by having a mono nucleoside base repeat sequence of at least five residues, or a di-nucleoside base repeat sequence of at least four di-nucleoside base units; and
2) removing, respectively, one nucleoside base residue or one di-nucleoside base unit from the repeat sequence and identifying the amino acid sequence of the protein encoded by the altered gene sequence as far as to include a new stop codon; and/or
3) removing, respectively, two nucleoside base residues or two di-nucleoside base units from the repeat sequence and identifying the amino acid sequence of the protein encoded by the altered gene sequence as far as to include a new stop codon; and/or
4) inserting, respectively, one nucleoside base residue or one di-nucleoside base unit in the repeat sequence and identifying the amino acid sequence of the protein encoded by the altered gene sequence as far as to include a new stop codon; and/or
5) inserting, respectively, two nucleoside base residues or two di-nucleoside base units in the repeat sequence and identifying the amino acid sequence of the protein encoded by the altered gene sequence as far as to include a new stop codon.

In order to determine whether the peptides thus identified are useable in the compositions and methods according to the present invention for the treatment or prophylaxis of cancer, the following further step should be performed:

6) determining whether the new peptide, either in their full length or as shorter fragments of the peptides, are able to stimulate T cells.

Optionally a further step may be added as follows:

7) determining peptides containing nested epitopes for different major HLA class I and/or HLA class II molecules.

DETAILED DESCRIPTION OF THE INVENTION

In the present description and claims, the amino acids are represented by their one letter abbreviation as known in the art.

The peptides of the present invention shall be explicitly exemplified through two different embodiments, wherein cancer develops based on frameshift mutations in specific genes, namely the BAX gene and TGFβRII gene:

I) BAX Gene

It has been established that the BAX gene is involved in regulation of survival or death of cells by promoting apoptosis. The human BAX gene contains a repeat sequence of eight deoxyguanosine bases (G8) in the third exon, spanning codons 38 to 41 (AT<u>GGGGGGGG</u>AG).

Frameshift mutations in this G8 repeat have been observed, both as G7 (AT<u>GGGGGGG</u> AGG) and G9 (AT <u>GGGGGGGGG</u>A) repeats, both in colon cancer cells and prostate cancer cells. The occurency is more than 50% of the examined cases (Rampino, N. et al., "Somatic frameshift mutations in the BAX gene in colon cancers of the microsatellite mutator phenotype.", Science (Washington D.C.), 275: 967–969, 1997). The modified BAX gene products are unable to promote apoptosis and thus makes further tumour progress possible. Furthermore the modified gene products are only found in cancer cells and are therefore targets for specific immunotherapy.

According to the present invention, peptides corresponding to the transformed BAX protein products arising from frameshift mutations in the BAX gene can be used as anticancer therapeutical agents or vaccines with the function to trigger the cellular arm of the immune system (T-cells) against cancer cells in patients afflicted with cancers associated with a modified BAX gene.

Frameshift mutations in the BAX gene result in mutant peptide sequences with the first amino acid of the altered sequence in position 41 as compared to the normal BAX protein (Table 1, seq.id. no. 1 to 4).

TABLE 1

| amino acid pos | 41 | 51 | 61 | 71 | |
|---|---|---|---|---|---|
| normal bax peptide; DS . . . | EAPELALDPV | PQDASTKKLS | ECLKRIGDEL | | |
| (bax − 1G); | RHPSWPWTRC | LRMRPPRS | | | seq. id. no. 1 |
| (bax + 2G); | GRHPSWPWTR | CLRMRPPRS | | | seq. id. no. 4 |
| (bax − 2G); | GTRAGPGPGA | SGCVHQEAER | VSQAHRGRTG | Q | seq. id. no. 2 |
| (bax + 1G); | GGTRAGPGPG | ASGCVHQEAE | RVSQAHRGRT | GQ | seq. id. no. 3 |

Table 2 shows one group of peptides according to the present invention:

TABLE 2

| | |
|---|---|
| IQDRAGRMGGRHPSWPWTRCLRMRPPRS: | seq. id. no. 5 |
| IQDRAGRMGGGRHPSWPWT: | seq. id. no. 6 |
| IQDRAGRMGGGTRAGPGPGASGCVHQEAERVSQAHRGRTGQ: | seq. id. no. 7 |
| IQDRAGRMGGGTRAGPGPG: | seq. id. no. 8 |

The peptides listed in Table 3 were used for in vitro generation of T cells that recognise mutant BAX peptides.

TABLE 3

| | |
|---|---|
| RHPSWPWTRCLRMRPPRS: | seq id no 1 |
| IQDRAGRMGGRHPSWPWTRCLR: | seq id no 9 |
| IQDRAGRMGGGRHPSWPWT: | seq id no 6 |
| ASGCVHQEAERVSQAHRGRTGQ: | seq id no 10 |
| GGTRAGPGPGASGCVHQEAERV: | seq id no 11 |
| IQDRAGRMGGGTRAGPGPGAS: | seq id no 12 |
| IQDRAGRMGGGTRAGPGPG: | seq id no 8 |

The most preferred peptides according to this embodiment of the present invention are listed in Table 4:

TABLE 4

| | |
|---|---|
| RHPSWPWTRCLRMRPPRS: | seq id no 1 |
| GTRAGPGPGASGCVHQEAERVSQAHRGRTGQ: | seq id no 2 |
| GGTRAGPGPGASGCVHQEAERVSQAHRGRTGQ: | seq id no 3 |
| GRHPSWPWTRCLRMRPPRS: | seq id no 4 |
| IQDRAGRMGGRHPSWPWTRCLRMRPPRS: | seq. id. no. 5 |
| IQDRAGRMGGGRHPSWPWT: | seq. id. no. 6 |
| IQDRAGRMGGGTRAGPGPGASGCVHQEAERVSQAHRGRTGQ: | seq. id. no. 7 |
| IQDRAGRMGGGTRAGPGPG: | seq id no 8 |
| IQDRAGRMGGRHPSWPWTRCLR: | seq id no 9 |
| ASGCVHQEAERVSQAHRGRTGQ: | seq id no 10 |
| GGTRAGPGPGASGCVHQEAERV: | seq id no 11 |
| IQDRAGRMGGGTRAGPGPGAS: | seq id no 12 |

2) TGFβRII

It has been established that the TGFβRII gene is involved in regulation of cell growth. TGFβRII is a receptor for TGFβ which down regulates cell growth. The human gene coding for TGFβRII contains a repeat sequence of ten deoxyadenosine bases (A10) from base no. 709 to base no. 718 (G AAAAAAAAAAG CCT). In colon cancers and pancreatic cancers frameshift mutations in this A10 repeat have been observed, both as A9 (GAAAAAAAAAGC CT) and A11 (G AAAAAAAAAAA GCC) repeats, in approximately 80% of the examined cases (Yamamoto, H., "Somatic frameshift mutations in DNA mismatch repair and proapoptosis genes in hereditary nonpolyposis colorectal cancer.", Cancer Research 58, 997–1003, Mar. 1, 1998). The modified TGFβRII gene products are unable to bind TGFβ and the signal for down regulation of cell growth is eliminated and thus makes further tumour progress possible. Furthermore the modified gene products are only found in cancer cells and are therefore targets for immunotherapy.

Consequently peptides corresponding to the transformed. TGFβRII protein products arising from frameshift mutations in the TGFβRII gene can be used as anticancer therapeutical agents or vaccines with the function to trigger the cellular arm of the immune system (T-cells) against cancer cells in patients afflicted with cancers associated with a modified TGFβRII gene.

Frameshift mutations in the TGFβRII gene result in mutant peptide sequences with the first amino acid of the altered sequence in either Position 133 (one and two base deletions) or 134 (one and two base insertions) as compared to the normal TGFβRII protein (Table 5, seq.id.nos. 13 and 21).

TABLE 5

| amino acid pos. | 133 | | | | | |
|---|---|---|---|---|---|---|
| normal TGFβRII; | K | PGETFFMCSC | SSDECNDNII | FSEEYNTSNP | DLLL | |
| (−1A); | S | LVRLSSCVPV | ALMSAMTTSS | SQKNITPAIL | TCC | seq id no 13 |
| (+2A); |   | SLVRLSSCVP | VALMSAMTTS | SSQKNITPAI | LTCC | seq id no 13 |
| TGFbRII + 1A); |   | AW | | | | |
| TGFbRII − 2A); | A | W | | | | |

Table 6 shows one groups of peptides of this invention:

TABLE 6

| | |
|---|---|
| SPKCIMKEKKSLVRLSSCVPVALMSAMTTSSSQKNITPAILTCC: | seq id no 14 |
| PKCIMKEKKKSLVRLSSCV: | seq id no 15 |
| SPKCIMKEKKAW: | seq id no 19 |
| PKCIMKEKKKAW: | seq id no 20 |

Table 7 presents peptides that were used for in vitro generation of T cells that recognise mutant TGFβRII peptides.

TABLE 7

| | |
|---|---|
| PKCIMKEKKKSLVRLSSCV: | seq id no 15 |
| ALMSAMTTSSSQKNITPAILTCC: | seq id no 16 |
| SLVRLSSCVPVALMSAMTTSSSQ: | seq id no 17 |
| SPKCIMKEKKSLVRLSSCVPVA: | seq id no 18 |

TABLE 7-continued

| | |
|---|---|
| SPKCIMKEKKAW: | seq id no 19 |
| PKCIMKEKKKAW: | seq id no 20 |
| AMTTSSSQKNITPAILTCC: | seq id no 21 |
| SLVRLSSCV: | seq id no 428 |

The most preferred peptides of this embodiment of the present invention are:

TABLE 8

| | |
|---|---|
| SLVRLSSCVPVALMSAMTTSSSQKNITPAILTCC: | seq id no 13 |
| SPKCIMKEKKSLVRLSSCVPVALMSAMTTSSSQKNITPAILTCC: | seq id no 14 |
| PKCIMKEKKKSLVRLSSCV: | seq id no 15 |
| ALMSAMTTSSSQKNITPAILTCC: | seq id no 16 |
| SLVRLSSCVPVALMSAMTTSSSQ: | seq id no 17 |
| SPKCIMKEKKSLVRLSSCVPVA: | seq id no 18 |
| SPKCIMKEKKAW: | seq id no 19 |
| PKCIMKEKKKAW: | seq id no 20 |
| AMTTSSSQKNITPAILTCC: | seq id no 21 |
| SLVRLSSCV: | seq id no 428 |

Other peptides of the invention can be fragments of the peptides listed in the Tables 1–8 above. Such fragments are most preferred from 9–16 amino acids long and include at least one amino acid from the mutant part of the protein.

As used in this description and claims the term fragment is intended to specify a shorter part of a longer peptide or of a protein.

Other cancer associated genes containing repeat sequences of a nucleoside base and which therefore are susceptible to frameshift mutations and consequently are potential candidates for peptides according to the present invention (seq id nos according to table 9 are given in parentheses in each case) are the following:

Human TGF-β-2 (hTGFβ2) gene (seq id nos 22–29)
Deleted in colorectal cancer (DCC) gene (seq.id.nos. 30–34)
Human breast and ovarian cancer susceptibility (BRCA1) gene (seq.id.nos. 378–387)
Human breast cancer susceptibility (BRCA2) gene (seq.id. nos. 35–94)
Human protein tyrosine phosphatase (hPTP) gene (seq.id. nos. 95–102)
Human DNA topoisomerase II (top2) gene (seq.id.nos. 103–108)
Human kinase (TTK) gene (seq.id.nos. 109–120)
Human transcriptional repressor (CTCF) gene (seq.id.nos. 121–127)
Human FADD-homologous ICE/CED-3-like protease gene (seq.id.nos. 128–133)
Human putative mismatch repair/binding protein (hMSH3) gene (seq.id.nos. 134–147)
Human retinoblastoma binding protein 1 isoform I (hRBP1) gene (seq.id.nos. 148–156)
Human FMR1 (hFMR1) gene (seq.id.nos. 157–161)
Human TINUR gene (seq.id.nos. 162–169) b-raf oncogene (seq.id.nos. 170–175)
Human neurofibromin (NF1) gene (seq.id.nos. 176–181)
Human germline n-myc gene (seq.id.nos. 182–188)
Human n-myc gene (seq.id.nos. 189–194)
Human ras inhibitor gene (seq.id.nos. 195–199)
Human hMSH6 gene (seq.id.nos. 200–203 and 293–297)
Human nasopharynx carcinoma EBV BNLF-1 gene (seq.id. nos. 204–210)
Human cell cycle regulatory protein (E1A-binding protein) p300 gene (seq.id.nos. 211–218)
Human B-cell lymphoma 3-encoded protein (bcl-3) gene (seq.id.nos. 219–226)
Human transforming growth factor-beta induced gene product (BIGH3) (seq.id.nos. 227–232)
Human transcription factor ETV1 gene. (seq.id.nos. 233–239)
Human insulin-like growth factor binding protein (IGFBP4) gene (seq.id.nos. 240–246)
Human MUC1 gene (seq.id.nos. 247–266)
Human protein-tyrosine kinase (JAK1) gene (seq.id.nos. 267–271)
Human protein-tyrosine kinase (JAK3) gene (seq.id.nos. 272–279)
Human Flt4 gene (for transmembrane tyrosinase kinase) (seq.id.nos. 280–284)
Human p53 associated gene (seq.id.nos. 285–292)
Human can (hCAN) gene (seq.id.nos. 298–300)
Human DBL (hDBL) proto-oncogene/Human MCF2PO (hMCF2PO) gene (seq.id.nos. 301–306)
Human dek (hDEK) gene (seq.id.nos. 307–309)
Human retinoblastoma related protein (p107) gene (seq.id. nos. 310–313)
Human G protein-coupled receptor (hGPR1) gene (seq.id. nos. 314–319)
Human putative RNA binding protein (hRBP56) gene (seq. id.nos. 320–325)
Human transcription factor (hITF-2) gene (seq.id.nos. 326–327)
Human malignant melanoma metastasis-supressor (hKiSS-1) gene (seq.id.nos. 328–334)
Human telomerase-associated protein TP-1 (hTP-1) gene (seq.id.nos. 335–348)
Human FDF-5 (hFDF-5) gene (seq.id.nos. 349–356)
Human metastasis-assosiated mta1 (hMTA1) gene (seq.id. nos. 357–362)
Human transcription factor TFIIB 90 kDa subunit (hTFIIB90) gene (seq id nos 363–369)
Human tumour suppressor (hLUCA-1) gene (seq id nos 370–377)
Human Wilm's tumour (WIT-1) associated protein (seq id nos 388–393)
Human cysteine protease (ICErel-III) gene (seq id nos 394–398 and 459)
Human Fas ligand (FasL) gene (seq id nos 399–403)
Human BRCA1-associated RING domain protein (BARD1) gene (seq id nos 404–417)
Human mcf.2 (hMCF.2) gene (seq id nos 418–422)
Human Fas antigen (fas) gene (seq id nos 423–427)
Human DPC4 gene (seq id nos 429–437).

The mutant peptides that are the results of frameshift mutation in these genes, in accordance with the present invention, are listed in table 9.

TABLE 9

| | |
|---|---|
| TVGRPHISC; | seq id no 22 |
| KTVGRPHISC; | seq id no 23 |
| KQWEDPTSPANVIALLQT; | seq id no 24 |
| QWEDPTSPANVIALLQT; | seq id no 25 |
| QKTIKSTRKKTVGRPHISC; | seq id no 26 |
| QKTIKSTRKKKTVGRPHISC; | seq id no 27 |
| QKTIKSTRKKKQWEDPTSPANVIALLQT; | seq id no 28 |
| QKTIKSTRKKQWEDPTSPANVIALLQT; | seq id no 29 |
| AADLQQQFVHFLDCWDVSSIPFTLHLPQAQDITT; | seq id no 30 |
| GKDAKEKSS; | seq id no 31 |
| GKDAKEKKSS; | seq id no 32 |
| GKDAKEKKAADLQQQFVHFLDCWDVSSIPFTLHLPQAQDITT; | seq id no 33 |
| GKDAKEKAADLQQQFVHFLDCWDVSSIPFTLHLPQAQDITT; | seq id no 34 |
| FSMKQTLMNVKNLKTK; | seq id no 35 |
| KFSMKQTLMNVKNLKTK; | seq id no 36 |
| VRTSKTRKKFSMKQTLMNVKNLKTK; | seq id no 37 |
| VRTSKTRKKKFSMKQTLMNVKNLKTK; | seq id no 38 |
| VRTSKTRKKNFP; | seq id no 39 |
| VRTSKTRKNFP; | seq id no 40 |

TABLE 9-continued

| Sequence | ID |
|---|---|
| IKKKLLQFQK; | seq id no 41 |
| KIKKKLLQFQK; | seq id no 42 |
| KSRRNYFNFKNNCQSRL; | seq id no 43 |
| SRRNYFNFKNNCQSRL; | seq id no 44 |
| TNLRVIQKIKKKLLQFQK; | seq id no 45 |
| TNLRVIQKKIKKKLLQFQK; | seq id no 46 |
| TNLRVIQKKSRRNYFNFKNNCQSRL; | seq id no 47 |
| TNLRVIQKSRRNYFNFKNNCQSRL; | seq id no 48 |
| KIMIT; | seq id no 49 |
| NIDKIPEKIMIT; | seq id no 50 |
| NIDKIPEKKIMIT; | seq id no 51 |
| IINAN; | seq id no 52 |
| KIINAN; | seq id no 53 |
| NDKTVSEKIINAN; | seq id no 54 |
| NDKTVSEKKIINAN; | seq id no 55 |
| NGLEKEYLMVNQKE; | seq id no 56 |
| SQTSLLEAKNGLEKEYLMVNQKE; | seq id no 57 |
| SQTSLLEAKKNGLEKEYLMVNQKE; | seq id no 58 |
| SQTSLLEAKKMA; | seq id no 59 |
| SQTSLLEAKMA; | seq id no 60 |
| TLVFPK; | seq id no 61 |
| KTLVFPK; | seq id no 62 |
| LKNVEDQKTLVFPK; | seq id no 63 |
| LKNVEDQKKTLVFPK; | seq id no 64 |
| LKNVEDQKKH; | seq id no 65 |
| LKNVEDQKH; | seq id no 66 |
| KKIQLY; | seq id no 67 |
| KKKIQLY; | seq id no 68 |
| RKRFSYTEYLASIIRFIFSVNRRKEIQNLSSCNFKI; | seq id no 69 |
| LRIVSYSKKKKIQLY; | seq id no 70 |
| LRIVSYSKKKKKIQLY; | seq id no 71 |
| LRIVSYSKKRKRFSYTEYLASIIRFIFSVNRRKEIQ-NLSSCNFKI; | seq id no 72 |
| LRIVSYSKRKRFSYTEYLASIIRFIFSVNRRKEIQN-LSSCNFKI; | seq id no 73 |
| QDLPLSSICQTIVTIYWQ; | seq id no 74 |
| KQDLPLSSICQTIVTIYWQ; | seq id no 75 |
| NRTCPFRLFVRRMLQFTGNKVLDRP; | seq id no 76 |
| GFVVSVVKKQDLPLSSICQTIVTIYWQ; | seq id no 77 |
| GFVVSVVKKKQDLPLSSICQTIVTIYWQ; | seq id no 78 |
| GFVVSVVKKNRTCPFRLFVRRMLQFTGNKVLDRP; | seq id no 79 |
| GFVVSVVKNRTCPFRLFVRRMLQFTGNKVLDRP; | seq id no 80 |
| YRKTKNQN; | seq id no 81 |
| KYRKTKNQN; | seq id no 82 |
| NTERPKIRTN; | seq id no 83 |
| DETFYKGKKYRKTKNQN; | seq id no 84 |
| DETFYKGKKYRKTKNQN; | seq id no 85 |
| DETFYKGKKNTERPKIRTN; | seq id no 86 |
| DETFYKGKNTERPKIRTN; | seq id no 87 |
| LSINNYRFQMKFYFRFTSHGSPFTSANF; | seq id no 88 |
| KLSINNYRFQMKFYFRFTSHGSPFTSANF; | seq id no 89 |
| NSVSTTTGFR; | seq id no 90 |
| NIQLAATKKLSINNYRFQMKFYFRFTSHGSPFTSANF; | seq id no 91 |
| NIQLAATKKKLSINNYRFQMKFYFRFTSHGSPFTSANF; | seq id no 92 |
| NIQLAATKKNSVSTTTGFR; | seq id no 93 |
| NIQLAATKNSVSTTTGFR; | seq id no 94 |
| MEHVAPGRMSASPQSPTQ; | seq id no 95 |
| KMEHVAPGRMSASPQSPTQ; | seq id no 96 |
| KWSTWLQAECQHLHSPQRSDKPQQAGLDQQHHCFAL-DSSPGPRPVFLQLLGLMGQGRHD; | seq id no 97 |
| WSTWLQAECQHLHSPQRSDKPQQAGLDQQHHCFALD-SSPGPRPVFLQLLGLMGQGRHD; | seq id no 98 |
| TFSVWAEKMEHVAPGRMSASPQSPTQ; | seq id no 99 |
| TFSVWAEKKMEHVAPGRMSASPQSPTQ; | seq id no 100 |
| TFSVWAEKKWSTWLQAECQHLHSPQRSDKPQQAGLD-QQHHCFALDSSPGPRPVFLQLLGLMGQGRHD; | seq id no 101 |
| TFSVWAEKWSTWLQAECQHLHSPQRSDKPQQAGLDQ-QHHCFALDSSPGPRPVFLQLLGLMGQGRHD; | seq id no 102 |
| HKWLKFCLLRLVKESFHE; | seq id no 103 |
| KHKWLKFCLLRLVKESFHE; | seq id no 104 |
| KGGKAKGKKHKWLKFCLLRLVKESFHE; | seq id no 105 |
| KGGKAKGKKKHKWLKFCLLRLVKESFHE; | seq id no 106 |
| KGGKAKGKKNTNG; | seq id no 107 |
| KGGKAKGKNTNG; | seq id no 108 |
| VNNFFKKL; | seq id no 109 |
| KVNNFFKKL; | seq id no 110 |
| LSQGNVKKVNNFFKKL; | seq id no 111 |
| LSQGNVKKKVNNFFKKL; | seq id no 112 |

TABLE 9-continued

| Sequence | ID |
|---|---|
| GEKNDLQLFVMSDRRYKIYWTVILLNPCGNLHLKTTSL; | seq id no 113 |
| KGEKNDLQLFVMSDRRYKIYWTVILLNPCGNLHLKTTSL; | seq id no 114 |
| KGKKMICSYS; | seq id no 115 |
| GKKMICSYS; | seq id no 116 |
| SSKTFEKKGEKNDLQLFVMSDRRYKIYWTVILLNPC-GNLHLKTTSL; | seq id no 117 |
| SSKTFEKKKGEKNDLQLFVMSDRRYKIYWTVILLNP-CGNLHLKTTSL; | seq id no 118 |
| SSKTFEKKKGKKMICSYS; | seq id no 119 |
| SSKTFEKKGKKMICSYS; | seq id no 120 |
| QRKPKRANCVIQRRAKM; | seq id no 121 |
| KQRKPKRANCVIQRRAKM; | seq id no 122 |
| NKENQKEQTALLYRGGQRCRCVCLRF; | seq id no 123 |
| NKENQKEQTALLYRGGQRCRCVCLRF; | seq id no 123 |
| PDYQPPAKKQRKPKRANCVIQRRAKM; | seq id no 124 |
| PDYQPPAKKKQRKPKRANCVIQRRAKM; | seq id no 125 |
| PDYQPPAKKNKENQKEQTALLYRGGQRCRCVCLRF; | seq id no 126 |
| PDYQPPAKNKENQKEQTALLYRGGQRCRCVCLRF; | seq id no 127 |
| NLSSLLI; | seq id no 128 |
| TCLPF; | seq id no 129 |
| QPTFTLRKNLSSLLI; | seq id no 130 |
| QPTFTLRKKNLSSLLI; | seq id no 131 |
| QPTFTLRKKTCLPF; | seq id no 132 |
| QPTFTLRKTCLPF; | seq id no 133 |
| RATFLLSLWECSLPQARLCLIVSRTGLLVQS; | seq id no 134 |
| GQHFYWHCGSAACHRRGCV; | seq id no 135 |
| KENVRDKKRATFLLSLWECSLPQARLCLIVSRTGLLVQS; | seq id no 136 |
| KENVRDKKKRATFLLSLWECSLPQARLCLIVSRTGLLVQS; | seq id no 137 |
| KENVRDKKGQHFYWHCGSAACHRRGCV; | seq id no 138 |
| KENVRDKKGQHFYWHCGSAACHRRGCV; | seq id no 139 |
| ITHTRWGITTWDSWSVRMKANWIQAQQNKSLILSPSFTK; | seq id no 140 |
| KITHTRWGITTWDSWSVRMKANWIQAQQNKSLILSPSFTK; | seq id no 141 |
| KLLTPGGELPHGILGQ; | seq id no 142 |
| LLTPGGELPHGILGQ; | seq id no 143 |
| PPVCELEKITHTRWGITTWDSWSVRMKANWIQAQQN--KSLILSPSFTK; | seq id no 144 |
| PPVCELEKKITHTRWGITTWDSWSVRMKANWIQAQQ--NKSLILSPSFTK; | seq id no 145 |
| PPVCELEKKLLTPGGELPHGILGQ; | seq id no 146 |
| PPVCELEKLLTPGGELPHGILGQ; | seq id no 147 |
| SLKDELEKMKI; | seq id no 148 |
| SLKDELEKKMKI; | seq id no 149 |
| LGQSSPEKNKN; | seq id no 150 |
| LGQSSPEKNKN; | seq id no 151 |
| RLRRINGRGSQIRSRNAFNRSEE; | seq id no 152 |
| EPKVKEEKKT; | seq id no 153 |
| EPKVKEEKKKT; | seq id no 154 |
| EPKVKEEKKRLRRINGRGSQIRSRNAFNRSEE; | seq id no 155 |
| EPKVKEEKRLRRINGRGSQIRSRNAFNRSEE; | seq id no 156 |
| TFRYKGKQHPFFST; | seq id no 157 |
| GPNAPEEKNH; | seq id no 158 |
| GPNAPEEKKNH; | seq id no 159 |
| GPNAPEEKKTFRYKGKQHPFFST; | seq id no 160 |
| GPNAPEEKTFRYKGKQHPFFST; | seq id no 161 |
| MQNTCV; | seq id no 162 |
| KMQNTCV; | seq id no 163 |
| KCKIRVFSK; | seq id no 164 |
| CKIRVFSK; | seq id no 165 |
| FFKRTVQKMQNTCV; | seq id no 166 |
| FFKRTVQKKMQNTCV; | seq id no 167 |
| FFKRTVQKKCKIRVFSK; | seq id no 168 |
| FFKRTVQKCKIRVFSK; | seq id no 169 |
| LPHYLAH; | seq id no 170 |
| CLITWLTN; | seq id no 171 |
| GSTTGLSATPLPHYLAH; | seq id no 172 |
| GSTTGLSATPPLPHYLAH; | seq id no 173 |
| GSTTGLSATPPCLITWLTN; | seq id no 174 |
| GSTTGLSATPCLITWLTN; | seq id no 175 |
| RFADKPRPN; | seq id no 176 |
| DLPTSPDQTRSGPVHVSVEP; | seq id no 177 |
| DSAAGCSGTPRFADKPRPN; | seq id no 178 |
| DSAAGCSGTPPRFADKPRPN; | seq id no 179 |
| DSAAGCSGTPPDLPTSPDQTRSGPVHVSVEP; | seq id no 180 |
| DSAAGCSGTPDLPTSPDQTRSGPVHVSVEP; | seq id no 181 |

TABLE 9-continued

| Sequence | ID |
|---|---|
| AHPETPAQNRLRIPCSRREVRSRACKPPGAQGSDERRGKASPGRDCDVRTGRP; | seq id no 182 |
| PAHPETPAQNRLRIPCSRREVRSRACKPPGAQGSDERRGKASPGRDCDVRTGRP; | seq id no 183 |
| RPTRRHPRRIASGSPAVGGR; | seq id no 184 |
| VAIRGHPRPPAHPETPAQNRLRIPCSRREVRSRACKPPGAQGSDERRGKASPGRDCDVRTGRP; | seq id no 185 |
| VAIRGHPRPPPAHPETPAQNRLRIPCSRREVRSRACKPPGAQGSDERRGKASPGRDCDVRTGRP; | seq id no 186 |
| VAIRGHPRPPRPTRRHPRRIASGSPAVGGR; | seq id no 187 |
| VAIRGHPRPRPTRRHPRRIASGSPAVGGR; | seq id no 188 |
| RGRTSGRSLSCCRRPRCRPAVASRSTAPSPRAGSRRCCLRTSCGAARPRRTRSACGDWVASPPTRSSSRTACGAASPPARSWSAP; | seq id no 189 |
| GGGHLEEV; | seq id no 190 |
| YFGGPDSTPRGRTSGRSLSCCRRPRCRPAVASRSTAPSPRAGSRRCCLRTSCGAARPRRTRSACGDWVASPPTRSSSRTACGAASPPARSWSAP; | seq id no 191 |
| YFGGPDSTPPRGRTSGRSLSCCRRPRCRPAVASRSTAPSPRAGSRRCCLRTSCGAARPRRTRSACGDWVASPPTRSSSRTACGAASPPARSWSAP; | seq id no 192 |
| YFGGPDSTPPGGGHLEEV; | seq id no 193 |
| YFGGPDSTPGGGHLEEV; | seq id no 194 |
| HRVADP; | seq id no 195 |
| LSQSSELDPPSSR; | seq id no 196 |
| LSQSSELDPPPSSR; | seq id no 197 |
| LSQSSELDPPHRVADP; | seq id no 198 |
| LSQSSELDPHRVADP; | seq id no 199 |
| VILLPEDTPPS; | seq id no 200 |
| VILLPEDTPPPS; | seq id no 201 |
| VILLPEDTPPLLRA; | seq id no 202 |
| VILLPELDPLLRA; | seq id no 203 |
| PSPLP; | seq id no 204 |
| PLLFHRPCSPSPALGATVLAVYRYE; | seq id no 205 |
| LLFHRPCSPSPALGATVLAVYRYE; | seq id no 206 |
| APRPPLGPPSPLP; | seq id no 207 |
| APRPPLGPPPSPLP; | seq id no 208 |
| APRPPLGPPPLLFHRPCSPSPALGATVLAVYRYE; | seq id no 209 |
| APRPPLGPPLLFHRPCSPSPALGATVLAVYRYE; | seq id no 210 |
| TQVLPQGCSLSLLHTTFPHRQVPHILDW; | seq id no 211 |
| PTQVLIPQGCSLSLLHTTFPHRQVPHILDW; | seq id no 212 |
| PLQSFPKDAASAFSTPRFPTDKFPTSWTGSCPGQPHGTRAFCQPGPEFNAFSAC; | seq id no 213 |
| LQSFPKDAASAFSTPRFPTDKFPTSWTGSCPGQPHGTRAFCQPGPEFNAFSAC; | seq id no 214 |
| PSPRPQSQPPTQVLPQGCSLSLLHTTFPHRQVPHILDW; | seq id no 215 |
| PSPRPQSQPPPTQVLPQGCSLSLLHTTFPHRQVPHILDW; | seq id no 216 |
| PSPRPQSQPPPLQSFPKDAASAFSTPRFPTDKFPTSWTGSCPGQPHGTRAFCQPGPEFNAFSAC; | seq id no 217 |
| PSPRPQSQPPPLQSFPKDAASAFSTPRFPTDKFPTSWTGSCPGQPHGTRAFCQPGPEFNAFSAC; | seq id no 218 |
| TAWPGRRRFTTPEPYCLCTPLGPWAPRFLW; | seq id no 219 |
| PTAWPGRRRFTTPEPYCLCTPLGPWAPRFLW; | seq id no 220 |
| PRPGPAGGALLPRSLTAFVPHSGHGLPVSSGEPAYTPIPHDVPHGTPPFC; | seq id no 221 |
| RPGPAGGALLPRSLTAFVPHSGHGLPVSSGEPAYTPIPHDVPHGTPPFC; | seq id no 222 |
| DLPAVPGPPTAWPGRRRFTTPEPYCLCTPLGPWAPRFLW; | seq id no 223 |
| DLPAVPGPPPTAWPGRRRFTTPEPYCLCTPLGPWAPRFLW; | seq id no 224 |
| DLPAVPGPPPRPGPAGGALLPRSLTAFVPHSGHGLPVSSGEPAYTPIPHDVPHGTPPFC; | seq id no 225 |
| DLPAVPGPPRPGPAGGALLPRSLTAFVPHSGHGLPVSSGEPAYTPIPHDVPHGTPPFC; | seq id no 226 |
| QWGLSWMS; | seq id no 227 |
| NGDCHGCPEGRQSL; | seq id no 228 |
| FTMDRVLTPQWGLSWMS; | seq id no 229 |
| FTMDRVLTPPQWGLSWMS; | seq id no 230 |
| FTMDRVLTPPNGDCHGCPEGRQSL; | seq id no 231 |
| FTMDRVLTPNGDCHGCPEGRQSL; | seq id no 232 |
| HHPARQCPHCIMHLQTQLIHRNLTGPSQLTSLHRSPYQIAATPWTTDFAASFFLNPVTPFLLCRRCQGKDVLCTNARCLSQTSPSHHKALSRTTTQCMNTTPWLAVRPAKAFPLL; | seq id no 233 |

TABLE 9-continued

| Sequence | ID |
|---|---|
| PHHPARQCPHCIMHLQTQLIHRNLTGPSQLTSLHRS-PYQIAATPWTTDFAASFFLNPVTPFLLCRRCQGK-DVLCTNARCLSQTSPSHHKALSRTTTQCMNTTP-WLAVRPAKAFPLL; | seq id no 234 |
| HTIQHASVPTASCISKLNSYTEN; | seq id no 235 |
| PQVGMRPSNPPHHPARQCPHCIMHLQTQLIHRNLT-GPSQLTSLHRSPYQIAATPWTTDFAASFFLNPVTP-FLLCRRCQGKDVLCTNARCLSQTSPSHHKALSRTT-TQCMNTTPWLAVRPAKAFPLL; | seq id no 236 |
| PQVGMRPSNP PPHHPARQCPHCIMHLQTQLIHRNL-TGPSQLTSLHRSPYQIAATPWTTDFAASFFLNPVT-PFLLCRRCQGKDVLCTNARCLSQTSPSHHKALSRT-TTQCMNTTPWLAVRPAKAFPLL; | seq id no 237 |
| PQVGMRPSNPPHTIQHASVPTASCISKLNSYTEN; | seq id no 238 |
| PQVGMRPSNPHTIQHASVPTASCISKLNSYTEN; | seq id no 239 |
| WAARSWCERRAAAVAPLAPWAWGCPAGCTPPVAARA-CAATRPEGWRSPCTH; | seq id no 240 |
| PWAARSWCERRAAAVAPLAPWAWGCPAGCTPPVAA-RACAATRPEGWRSPCTH; | seq id no 241 |
| RGLRGAGARGGLRLLRHLRPGLGDALRGVHPPLR-LGPALLPAPRGGEAPAHTDARARRVHGAGGDRGHP-GPAAL; | seq id no 242 |
| EEKLARCRPPWAARSWCERRAAAVAPLAPWAWGCPA-GCTPPVAARACAATRPEGWRSPCTH; | seq id no 243 |
| EEKLARCRPPPWAARSWCERRAAAVAPLAPWAWGCP-AGCTPPVAARACAATRPEGWRSPCTH; | seq id no 244 |
| EEKLARCRPPRGLRGAGARGGLRLLRHLRPGLGDA-LRGVHPPLRLGPALLPAPRGGEAPAHTDARARRVH-GAGGDRGHPGPAAL; | seq id no 245 |
| EEKLARCRPRGLRGAGARGGLRLLRHLRPGLGDALR-GVHPPLRLGPALLPAPRGGEAPAHTDARARRVHGA-GGDRGHPGPAAL; | seq id no 246 |
| QPPVSPRPRRPGRPAPPPPQPMVSPRRRTTGPPW-RPPPLQSTMSPPPQALHQAQLLLWCTTAPLPGLPQ-PQPARALHSQFPATTLILLPPLPAIAPRLMPVALT-IARYLLSPPPITALLPSCLLGSLSFSCLFTFQTSS-LIPLWKIPAPTTTKSCRETFLKW; | seq id no 247 |
| SPGCHLGPGDQAAPGLHRPPSPWCHLGAGQQARLGV-HRPSSPQCHLGLRLCIRLSFYSGAQRHLCQGYHNP-SQQEHSILNSQPPL; | seq id no 248 |
| KPAPGSTAPQPPVSPRPRRPGRPRAPPPPQPMVSPR-RRTTGPPWRPPPLQSTMSPPPQALHQAQLLLWCTT-APLPGLPQPQPARALHSQFPATTLILLPPLPAIAP-RLMPVALTIARYLLSPPPITALLPSCLLGSLSFSC-LFTFQTSSLIPLWKIPAPTTTKSCRETFLKW; | seq id no 249 |
| KPAPGSTAPPQPPVSPRPRRPGRPRAPPPPQPMVSP-RRRTTGPPWRPPPLQSTMSPPPQALHQAQLLLWCT-TAPLPGLPQPQPARALHSQFPATTLILLPPLPAIA-PRLMPVALTIARYLLSPPPITALLPSCLLGSLSFS-CLFTFQTSSLIPLWKIPAPTTTKSCRETFLKW; | seq id no 250 |
| KPAPGSTAPPSPGCHLGPGDQAAPGLHRPPSPWCHL-GAGQQARLGVHRPSSPQCHLGLRLCIRLSFYSGA-QRHLCQGYHNPSQQEHSILNSQPPL; | seq id no 251 |
| KPAPGSTAPSPGCHLGPGDQAAPGLHRPPSPWCHL-GAGQQARLGVHRPSSPQCHLGLRLCIRLSFYSGAQ-RHLCQGYHNPSQQEHSILNSQPPL; | seq id no 252 |
| QPMVSPRRRTTGPPWRPPPLQSTMSPPPQALHQAQL-LLWCTTAPLPGLPQPQPARALHSQFPATTLILLPP-LPAIAPRLMPVALTIARYLLSPPPITALLPSCLLG-SLSFSCLFTFQTSSLIPLWKIPAPTTTKSCRETFL-KW; | seq id no 253 |
| SPWCHLGAGQQARLGVHRPSSPQCHLGLRLCIRLSF-YSGAQRHLCQGYHNPSQQEHSILNSQPPL; | seq id no 254 |
| RPPPGSTAPQPMVSPRRR; | seq id no 255 |
| RPPPGSTAPPQPMVSPRRR; | seq id no 256 |
| RPPPGSTAPPSPWCHLGA; | seq id no 257 |
| RPPPGSTAPSPWCHLGA; | seq id no 258 |
| RPRAPPPPPSPWCHL; | seq id no 259 |
| RPRAPPPPPSPWC; | seq id no 260 |
| RPRAPPPPPAHGVTSAP; | seq id no 261 |
| RPRAPPPPPAHGV; | seq id no 262 |
| APGLHRPPQPMVSP; | seq id no 263 |
| AAPGLHRPQPMVSPR; | seq id no 264 |
| PGLHRPPPAHGVT; | seq id no 265 |
| APGLHRPPAHGVTS; | seq id no 266 |
| VDRPQHTEWLSWSNLYRIRHQ; | seq id no 267 |
| HYLCTDVAPR; | seq id no 268 |
| HYLCTDVAPPR; | seq id no 269 |
| HYLCTDVAPPVDRPQHTEWLSWSNLYRIRHQ; | seq id no 270 |
| HYLCTDVAPVDRPQHTEWLSWSNLYRIRHQ; | seq id no 271 |

TABLE 9-continued

| Sequence | SEQ ID |
|---|---|
| SAYLSPLGTTWLRTCACRLPRPAASCLCTTPSLLWPRRTCPAGSPRATSSPWRMPAPKSCCTTGLAFTSPIGLGWRSATASGYARIWPVLSLTCQSWSTSLPSTAVTW; | seq id no 272 |
| PSAYLSPLGTTWLRTCACRLPRPAASCLCTTPSLLWPRRTCPAGSPRATSSPWRMPAPKSCCTTGLAFTSPIGLGWRSATASGYARIWPVLSLTCQSWSTSLPSTAVTW; | seq id no 273 |
| PAPIFLLWGPLG; | seq id no 274 |
| APIFLLWGPLG; | seq id no 275 |
| LPARAPGPPSAYLSPLGTTWLRTCACRLPRPAASCLCTTPSLLWPRRTCPAGSPRATSSPWRMPAPKSCCTTGLAFTSPIGLGWRSATASGYARIWPVLSLTCQSWSTSLPSTAVTW; | seq id no 276 |
| LPARAPGPPPSAYLSPLGTTWLRTCACRLPRPAASCLCTTPSLLWPRRTCPAGSPRATSSPWRMPAPKSCCTTGLAFTSPIGLGWRSATASGYARIWPVLSLTCQSWSTSLPSTAVTW; | seq id no 277 |
| LPARAPGPPPAPIFLLWGPLG; | seq id no 278 |
| LPARAPGPPAPIFLLWGPLG; | seq id no 279 |
| DLEHHGGVTRHRHR; | seq id no 280 |
| LVSDYSMTPRP; | seq id no 281 |
| LVSDYSMTPPRP; | seq id no 282 |
| LVSDYSMTPPDLEHHGGVTRHRHR; | seq id no 283 |
| LVSDYSMTPDLEHHGGVTRHRHR; | seq id no 284 |
| FHHIATDVGPFVRIGFLKIKGKIKGKSLRKPNWKTQHKLKRALMFLIVKKL; | seq id no 285 |
| PFHHIATDVGPFVRIGFLKIKGKIKGKSLRKPNWKTQHKLKRALMFLIVKKL; | seq id no 286 |
| PSITLQQMLAPS; | seq id no 287 |
| SITLQQMLAPS; | seq id no 298 |
| TSCNEMNPPFHHIATDVGPFVRIGFLKIKGKIKGKSLRKPNWKTQHKLKRALMFLIVKKL; | seq id no 289 |
| TSCNEMNPPPFHHIATDVGPFVRIGFLKIKGKIKGKSLRKPNWKTQHKLKRALMFLIVKKL; | seq id no 290 |
| TSCNEMNPPSITLQQMLAPS; | seq id no 291 |
| TSCNEMNPPPSITLQQMLAPS; | seq id no 292 |
| LEMILFLMTF | seq id no 293 |
| HPCITKTFFLEMILFLMTF; | seq id no 294 |
| HPCITKTFFFLEMILFLMTF; | seq id no 295 |
| HPCITKTFFWR; | seq id no 296 |
| HPCITKTFWR; | seq id no 297 |
| LMFEHSQMRLNSKNAHLPIISF; | seq id no 298 |
| EYGSIIAFLMFEHSQMRLNSKNAHLPIISF; | seq id no 299 |
| EYGSIIAFFLMFEHSQMRLNSKNAHLPIISF; | seq id no 300 |
| HLNKGRRLGDKIRAT; | seq id no 301 |
| FHLNKGRRLGDKIRAT; | seq id no 302 |
| VTSGTPFFHLNKGRRLGDKIRAT; | seq id no 303 |
| VTSGTPFFFHLNKGRRLGDKIRAT; | seq id no 304 |
| VTSGTPFFFI; | seq id no 305 |
| VTSGTPFFI; | seq id no 306 |
| CEIERIHFFF; | seq id no 307 |
| CEIERIHFFSK; | seq id no 308 |
| CEIERIHFSK; | seq id no 309 |
| FRYISKSI; | seq id no 310 |
| RYISKSI; | seq id no 311 |
| FKKYEPIFFRYISKSI; | seq id no 312 |
| FKKYEPIFRYISKSI; | seq id no 313 |
| FPDSDQPGPLYPLDPSCLISSASNPQELSDCHYIHLAFGFSNWRSCPVLPGHCGVQ; | seq id no 314 |
| PDSDQPGPLYPLDPSCLISSASNPQELSDCHYIHLAFGFSNWRSCPVLPGHCGVQ; | seq id no 315 |
| LNMFASVFS; | seq id no 316 |
| LNMFASVFFS; | seq id no 317 |
| LNMFASVFFPDSDQPGPLYPLDPSCLISSASNPQELSDCHYIHLAFGFSNWRSCPVLPGHCGVQ; | seq id no 318 |
| LNMFASVFPDSDQPGPLYPLDPSCLISSASNPQELSDCHYIHLAFGFSNWRSCPVLPGHCGVQ; | seq id no 319 |
| AMEETVVVAVATVETEVEAMEETGVVAAMEETEVGATEETEVAMEAKWEEETTTEMISATDHT; | seq id no 320 |
| LWVRPWLWEWLRWRPKWRLWRRQEWWRLWRRPRWGLRRRPRWLWRENGRKKRLQK; | seq id no 321 |
| YGGDRSRGAMEETVVVAVATVETEVEAMEETGVVAAMEETEVGATEETEVAMEAKWEEETTTEMISATDHT; | seq id no 322 |
| YGGDRSRGGAMEETVVVAVATVETEVEAMEETGVVAAMEETEVGATEETEVAMEAKWEEETTTEMISATDHT; | seq id no 323 |
| YGGDRSRGGLWVRPWLWEWLRWEPKWRLWRRQEWWRLWRRPRWGLRRRPRWLWRENGRKKRLQK; | seq id no 324 |

TABLE 9-continued

| Sequence | ID |
|---|---|
| YGGDRSRGLWVRPWLWEWLRWEPKWRLWRRQEWWR-LWRRPRWGLRRRPRWLWRENGRKKRLQK; | seq id no 325 |
| EFGGGRRQK; | seq id no 326 |
| EFGGGRRQK; | seq id no 327 |
| RRAKGGGAGASNPRQ; | seq id no 328 |
| GRRAKGGGAGASNPRQ; | seq id no 329 |
| DVGLREGALELPTRGNKRNVA; | seq id no 330 |
| MRGGGGVGGRRAKGGGAGASNPRQ; | seq id no 331 |
| MRGGGGVGGRRAKGGGAGASNPRQ; | seq id no 332 |
| MRGGGGVGGDVGLREGALELPTRGNKRNVA; | seq id no 333 |
| MRGGGGVGDVGLREGALELPTRGNKRNVA; | seq id no 334 |
| VWQLAGPMLAGWRSLGSWFCRMYGI; | seq id no 335 |
| CGSWPALCWRAGGVWAVGSAGCMEYDPEALPAAWGP-AAAATVHPRR; | seq id no 336 |
| RRYPCEWGVWQLAGPMLAGWRSLGSWFCRMYGI; | seq id no 337 |
| RRYPCEWGGVWQLAGPMLAGWRSLGSWFCRMYGI; | seq id no 338 |
| RRYPCEWGGCGSWPAlCWRAGGVWAVGSAGCMEYD-EALPAAWGPAAAATVHPRR; | seq id no 339 |
| RRYPCEWGCGSWPALCWRAGGVWAVGSAGCMEYDPE-ALPAAWGPAAAATVHPRR; | seq id no 340 |
| LWLWAGWTVWWSCGPGEKGHGWPSLPTMALLLLRFS-CMRVASY; | seq id no 341 |
| GLWLWAGWTVWWSCGPGEKGHGWPSLPTMALLLL-RFSCMRVASY; | seq id no 342 |
| GCGCGPAGQYGGAVGLARRGTAGCLPCPPWLCCCCA-FPACGLPGTDGWRGWQGSGCVRVSGSAPWAPGFPF-SPPCPLCGTQPRW; | seq id no 343 |
| CGCGPAGQYGGAVGLARRGTAGCLPCPPWLCCCCAF-PACGLPGTDGWRGWQGSGCVRVSGSAPWAPGFPFSP-PCPLCGTQPRW; | seq id no 344 |
| LAFNVPGGLWLWAGWTVWWSCGPGEKGHGWPSLPTM-ALLLLRFSCMRVASY; | seq id no 345 |
| LAFNVPGGLWLWAGWTVWWSCGPGEKGHGWPSLPT-MALLLLRFSCMRVASY; | seq id no 346 |
| LAFNVPGGCGCGPAGQYGGAVGLARRGTAGCLPCP-PWLCCCCAFPACGLPGTDGWRGWQGSGCVRVSGSA-PWAPGFPFSPPCPLCGTQPRW; | seq id no 347 |
| LAFNVPGGCGCGPAGQYGGAVGLARRGTAGCLPCPP-WLCCCCAFPACGLPGTDGWRGWQGSGCVRVSGSAP-WAPGFPFSPPCPLCGTQPRW; | seq id no 348 |

TABLE 9-continued

| Sequence | ID |
|---|---|
| PPMPMPGQREAPGRQEA; | seq id no 349 |
| GPPMPMPGQREAPGRQEA; | seq id no 350 |
| GHQCQCQGKGRHRADRRPDTAQEE; | seq id no 351 |
| HQCQCQGKGRHRADRRPDTAQEE; | seq id no 352 |
| GGHSYGGGPPMPMPGQREAPGRQEA; | seq id no 353 |
| GGHSYGGGGPPMPMPGQREAPGRQEA; | seq id no 354 |
| GGHSYGGGGHQCQCQGKGRHRADRRPDTAQEE; | seq id no 355 |
| GGHSYGGGHQCQCQGKGRHRADRRPDTAQEE; | seq id no 356 |
| APCPQSSGGG; | seq id no 357 |
| LPAPSQAAADELDRRPG; | seq id no 358 |
| TKVRLIRGAPCPQSSGGG; | seq id no 359 |
| TKVRLIRGGAPCPQSSGGG; | seq id no 360 |
| TKVRLIRGGLPAPSQAAADELDRRPG; | seq id no 361; |
| TKVRLIRGLPAPSQAAADELDRRPG; | seq id no 362 |
| CSLAKDGSTEDTVSSLCGEEDTEDEELEAAASHLNK-DLYRELLGG; | seq id no 363 |
| GCSLAKDGSTEDTVSSLCGEEDTEDEELEAAASHLN-KDLYRELLGG; | seq id no 364 |
| AAAWQKMAPPRTPRPACVARR; | seq id no 365 |
| ENSRPKRGGCSLAKDGSTEDTVSSLCGEEDTEDEEL-EAAASHLNKDLYRELLGG; | seq id no 366 |
| ENSRPKRGGCSLAKDGSTEDTVSSLCGEEDTEDE-ELEAAASHLNKDLYRELLGG; | seq id no 367 |
| ENSRPKRGGAAAWQKMAPPRTPRPACVARR; | seq id no 368 |
| ENSRPKRGAAAWQKMAPPRTPRPACVARR; | seq id no 369 |
| HCVLAASGAS; | seq iD no 370 |
| GHCVLAASGAS; | seq id no 371 |
| GTASSRPLGLPKPHLHRPVPIRHPSCPK; | seq id no 372 |
| TASSRPLGLPKPHLHRPVPIRHPSCPK; | seq id no 373 |
| AGTLQLGGHCVLAASGAS; | seq id no 374 |
| AGTLQLGGGHCVLAASGAS; | seq id no 375 |
| AGTLQLGGGTASSRPLGLPKPHLHRPVPIRHPSCPK; | seq id no 376 |
| AGTLQLGGTASSRPLGLPKPHLHRPVPIRHPSCPK; | seq id no 377 |
| RRTPSTEKR; | seq id no 378 |
| RRTPSTEKKR; | seq id no 379 |
| RRTPSTEKKGRSEC; | seq id no 380 |
| RRTPSTEKGRSEC; | seq id no 381 |
| STTKCQSGTAETYNSWKVKNLQLEPRRVTSQMNRQV-KDMTAILSQS; | seq id no 382 |

TABLE 9-continued

| | |
|---|---|
| SSEEIKKKSTTKCQSGTAETYNSWKVKNLQLEPRRV-TSQMNRQVKDMTAILSQS | seq id no 384 |
| SSEEIKKKKSTTKCQSGTAETYNSWKVKNLQLEPRR-VTSQMNRQVKDMTAILSQS; | seq id no 385 |
| SSEEIKKKKVQPNASQAQQKPTTHGR; | seq id no 386 |
| SSEEIKKKVQPNASQAQQKPTTHGR; | seq id no 387 |
| NRGWVGAGE; | seq id no 388; |
| IEAG; | seq id no 389 |
| VHNYCNMKNRGWVGAGE; | seq id no 390 |
| VHNYCNMKKNRGWVGAGE; | seq id no 391 |
| VHNYCNMKKIEAG; | seq id no 392 |
| VHNYCNMKIEAG; | seq id no 393 |
| QLRCWNTWAKMFFMVFLIIWQNTMF; | seq id no 394 |
| VKKDNHKKQLRCWNTWAKMFFMVFLIIWQNTMF; | seq id no 395 |
| VKKDNHKKKQLRCWNTWAKMFFMVFLIIWQNTMF; | seq id no 396 |
| VKKDNHKKKNS; | seq id no 397 |
| VKKDNHKKNS; | seq id no 398 |
| GAEESGPFNRQVQLKVHASGMGRHLWNCPAFWSEV; | seq id no 399 |
| HPSPPPEKRS; | seq id no 400 |
| HPSPPPEKKRS; | seq id no 401 |
| HPSPPPEKKGAEESGPFNRQVQLKVHASGMGRHLW-NCPAFWSEV; | seq id no 402 |
| HPSPPPEKGAEESGPFNRQVQLKVHASGMGRHLWN-CPAFWSEV; | seq id no 403 |
| MQVLSKTHMNLFPQVLLQMFLRGLKRLLQDLEKSKK-RKL; | seq id no 404 |
| RCKSARLI; | seq id no 405 |
| VQTQPAIKKMQVLSKTHMNLFPQVLLQMFLRGLKRL-LQDLEKSKKRKL; | seq id no 406 |
| VQTQPAIKKKMQVLSKTHMNLFPQVLLQMFLRGLKR-LLQDLEKSKKRKL | seq id no 407 |
| VQTQPAIKKRCKSARLI; | seq id no 408 |
| VQTQPAIKRCKSARLI; | seq id no 409 |
| ARSGKKQKRKL; | seq id no 410 |
| ARSGKKQKKRKL; | seq id no 411 |
| ARSGKKQKKENFS; | seq id no 412 |
| ARSGKKQKENFS; | seq id no 413 |
| KASARSGKSKKRKL; | seq id no 414 |
| KASARSGKKSKKRKL; | seq id no 415 |

TABLE 9-continued

| | |
|---|---|
| KASARSGKKAKKENSF; | seq id no 416 |
| KASARSGKAKKENSF; | seq id no 417 |
| HLNKGRRLGDKIRAT; | seq id no 418 |
| VTSGTPFFHLNKGRRLGDKIRAT; | seq id no 419 |
| VTSGTPFFFHLNKGRRLGDKIRAT; | seq id no 420 |
| VTSGTPFFFI; | seq id no 421 |
| VTSGTPFFI; | seq id no 422 |
| VTLLYVNTVTLAPNVNMESSRNAHSPATPSAKRK-DPDLTWGGFVFFFCQFH; | seq id no 423 |
| KCRCKPNFFVTLLYVNTVTLAPNVNMESSRNAHSP-ATPSAKRKDPDLTWGGFVFFFCQFH; | seq id no 424 |
| KCRCKPNFFVTLLYVNTVTLAPNVNMESSRNAH-SPATPSAKRKDPDLTWGGFVFFFCQFH | seq id no 425 |
| KCRCKPNFFL; | seq id no 426 |
| KCRCKPNFL; | seq id no 427 |
| LVKKLKEKKMNWIL; | seq id no 429 |
| LVKKLKEKKKMNWIL; | seq id no 430 |
| LVKKLKEKKR; | seq id no 431 |
| LVKKLKEKR; | seq id no 432 |
| AAIVKDCCR; | seq id no 433 |
| SQPASILGRKL; | seq id no 434 |
| SQPASILGKRKL; | seq id no 435 |
| SQPASILGKAAIVKDCCR; | seq id no 436 |
| SQPASILGAAIVKDCCR; | seq id no 437 |
| NTWAKMFFMVFLIIWQNTMF; | seq id no 459 |

Examples of cancers particularly suitable for treatment with one or a combination of several of this compounds are: colorectal cancer, breast cancer, small-cell lung cancer, non small-cell lung cancer, liver cancer (primary and secondary), renal cancer, melanoma, ovarian cancer, cancer of the brain, head and neck cancer, pancreatic cancer, gastric cancer, eosophageal cancer, prostate cancer and leukemias and lymphomas.

Below are listed some examples of where these mutations may result in gene products that result in development of tumours:

Development of colorectal cancers are believed to result from a series of genetic alterations. Deleted in colorectal cancer (DCC) gene (seq id nos 30–34), Human cysteine protease (ICErel-III) gene (seq id nos 394–398 and 459), Human putative mismatch repair/binding protein (hMSH3) gene (Seq id nos 134–147), Human hMSH6 gene (seq id nos 200–203 and 293–297), Human n-myc gene (seq id nos 189–194), Human TGFβ2 (hTGFβ2) gene (seq id nos 22–29), Human p53 associated gene (seq id nos 285–292 may be involved in colorectal cancer.

Human breast cancer susceptibility (BRCA2) (seq id nos 35–94) and Human BRCA1-associated RING domain protein (BARD1) gene (seq id nos 404–417) are involved in breast cancer and ovarian cancer Human hMSH6 gene (seq id nos 200–203 and 293–297) may be involved in brain tumours.

Gene alteration are frequent in many types of adenocarcinomas, below are listed some genes that are mutated in many cancers:

Human breast cancer susceptibility (BRCA2) gene (seq id nos 35–94), Deleted in colorectal cancer (DCC) gene (seq id nos 30–34), Human putatative mismatch repair/binding protein (hMSH3) gene (seq id nos 134–147), Human hMSH6 gene (seq id nos 200–203 and 293–297), human N-MYC gene (seq id no 189–194), Human TGFb2 (hTGFb2) gene (seq id nos 22–29), Human p53 associated gene (seq id nos 285–292), Human MUC1 gene (seq id nos 247–266), Human germline n-myc gene (seq id nos 182–188), Human Wilm's tumour (WIT-1) associated protein (seq id nos 388–393), Human nasopharynx carcinoma EBV BNLF-1 gene (seq id nos 204–210), Human transforming growth factor-beta induced gene product (BIGH3) (seq id nos 227–232).

Many of the mutated genes may result in development of leukemias and lymphomas: Human neurofibromin (NF1) gene (seq id nos 176–181), b-raf oncogene (seq id nos 170–175), Human protein-tyrosine kinase (JAK1) gene (seq id nos 267–271), Human protein-tyrosine kinase (JAK3) gene (seq id nos 272–279) are examples.

Genes involved in malignant melanoma: Human malignant melanoma metastasis-supressor (hKiSS-1) gene (seq id nos 328–334), Genes involved in metastasis: Human metastasis-associated mtal (hMTA1) gene (seq id nos 357–362).

Cell cycle control and signal transduction is strictly regulated. Frameshift mutations in these genes may result in uncontrolled cell growth. Examples of genes which may be susceptible are: Human protein tyrosine phosphatase (hPTP) gene (seq id nos 95–102), Human kinase (TTK) gene (seq id nos 109–120), Human transcriptional repressor (CTCF) gene (seq id nos 121–127), Human cell cycle regulatory protein (E1A-binding protein) p300 gene (seq id nos 211–218), Human transforming growth factor-beta induced gene product (BIGH3) (seq id nos 227–232), Human FLt4 gene (for transmembrane tyrosinase kinase (seq id nos 280–284), Human G protein-coupled receptor (hGPR1) gene (seq id nos 314–319), Human transcription factor (hITF-2) gene (seq id nos 326–327), Human telomerase-associated protein TP-1 (hTP-1) gene (seq id nos 335–348), Human transcription factor TFIIB 90 kDa subunit (hTF-BIIB90) gene (seq id nos 363–369), Human FADD-homologous ICE/CED-3like protease gene (seq id nos 128–133)

Mutations in DNA synthesis or repair enzymes may also lead to uncontrolled cell growth. Human DNA topoisomerase II (top2) gene (seq id nos 103–108) and Human putative mismatch repair/binding protein (hMSH3) gene (seq id nos 134–147) and (hMSH6) gene (seq id nos 200–203 and 293–297).

The following are tumour suppressor genes, Human retinoblastoma binding protein 1 isoform I (hRBP1) gene (seq id nos 148–156), Human neurofibromin (NF1) gene (seq id nos 176–181), Human p53 associated gene (seq id nos 285–292, Human retinoblastoma related protein (p107) gene (seq id nos 310–313), Human tumour suppressor (hLUCA-1) gene (seq id nos 370–377), Mutations in these genes may result in development of cancer.

The following are oncogenes, proto-oncogenes or putative oncogenes;

Human germline n-myc gene (seq id nos 182–188), Human n-myc gene (seq id nos 189–194), Human can (hCAN) gene (seq id nos 298–300), Human dek (hDEK) gene (seq id nos 307–309), b-raf oncogene (seq id nos 170–175), Human DBL (hDBL) proto-oncogene/Human MCF2PO (hMCF2PO) gene (seq id nos 301–306). Frameshift mutations in these genes may lead to development of cancer.

Biological Experiments

Figure 1:
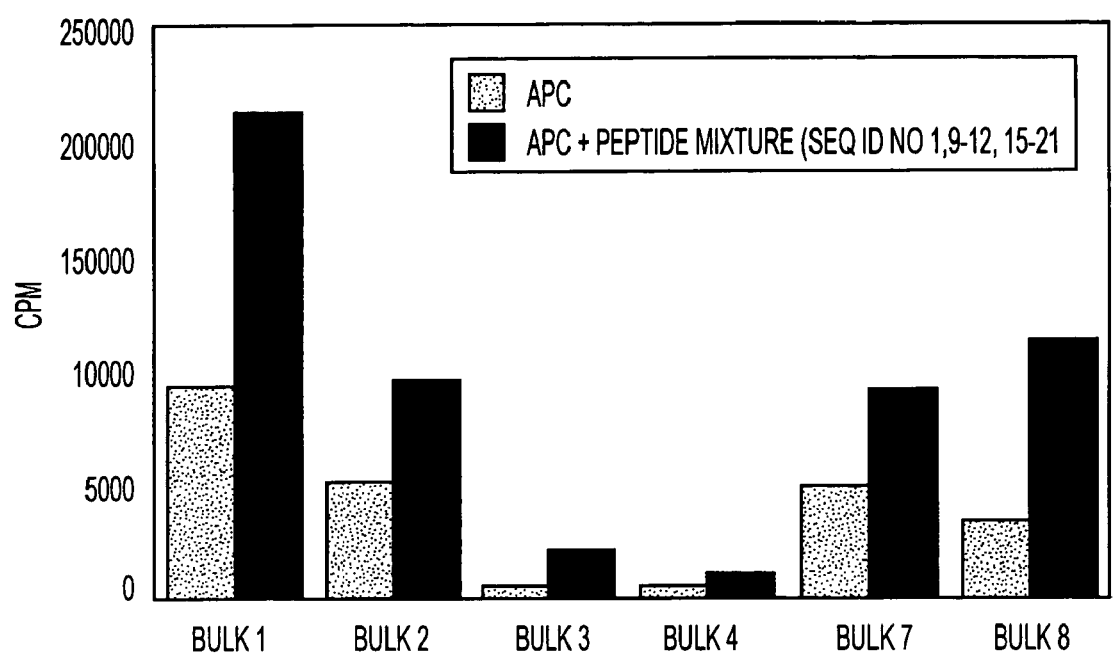
FIG. 1.

It has been demonstrated that T cells from normal donors can be stimulated with a mixture of peptides containing both mutant BAX and mutant TGFβRII peptides. Peptide mixture dependent T cell proliferation in blood samples from six different donors are shown in FIG. 1. The results were obtained by stimulating peripheral blood mononuclear cells (PBMCs) from each donor with a mixture of mutant BAX peptides (seq id nos 1,9–12) and mutant TGFβRII peptides (seq id nos 15–21). The concentration of each cells were isolated from the cell product before DCs were derived using standard methods.

Figure 4:
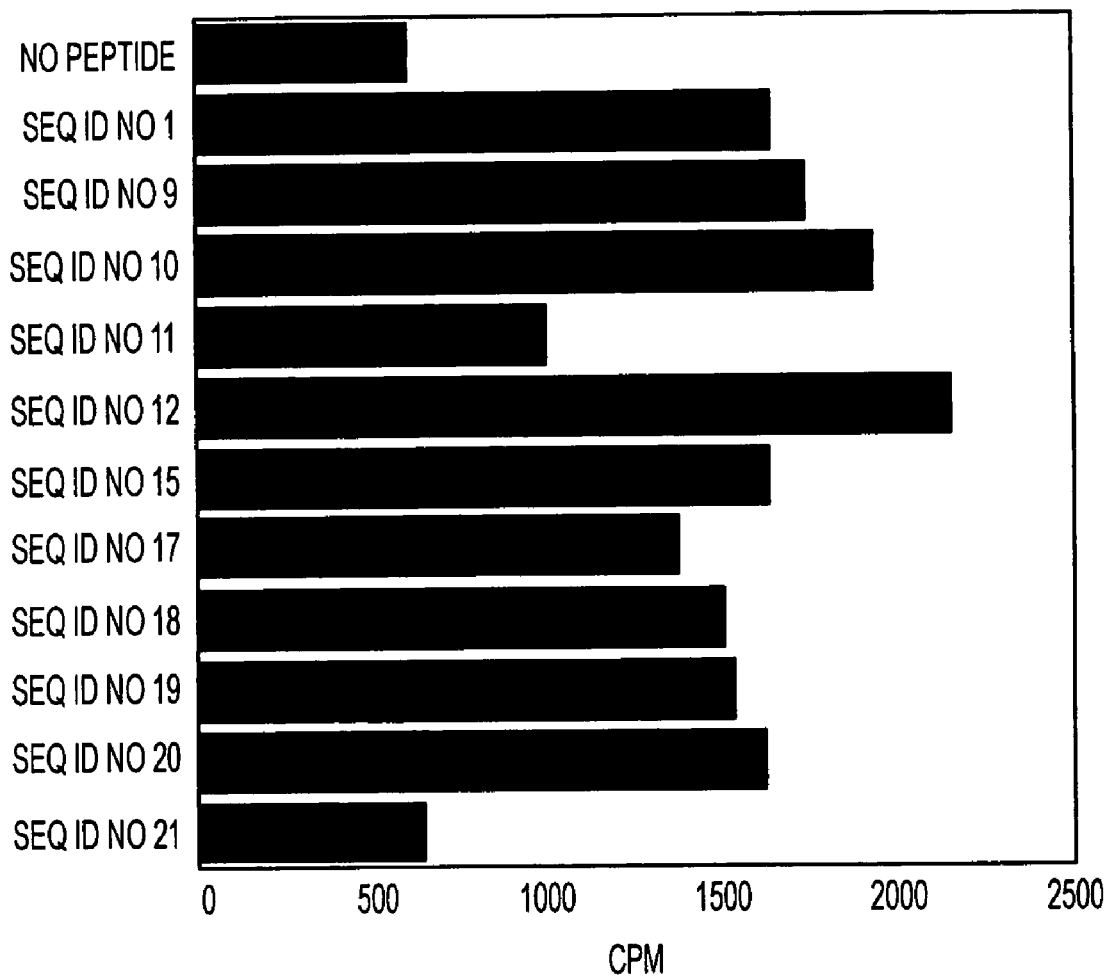

FIG. 4:

FIG. 4 shows the capability of T cells obtained from ascites fluid of a pancreatic cancer patient to recognise and proliferate to different synthetic peptides derived from mutant BAX (seq id nos 1,9–12) and mutant TGFβRII (seq id nos 15,17–21). The T cell line was obtained after expansion of T cells present in the ascites fluid of a patient with pancreatic adenocarcinoma. The T cell line was expanded in vitro by culturing with 100 U/ml recombinant interleukin-2 (rIL-2) (Amersham, Aylesbury, UK) for one week before beeing tested in a proliferation assay.

Autologous, irradiated (30Gy) PBMCs were seeded 5×104 in u-bottomed 96-well plates (Costar, Cambridge, Mass.) and pulsed with single synthetic peptides at 20 μM for 2 h. The T cells were added 5×104 per well and the plates were incubated for four days at 37° C. with addition of 18.5×104 Bq/mL 3H-thymidine for the last 12 hours before harvesting. The plates were counted in a liquid scintillation counter (Packard Topcount). Data represent specific proliferation to the different synthetic peptides and values are expressed as the mean of triplicate cultures. These results show that T cells isolated from a pancreatic cancer patient are capable of responding to a panel of peptides carrying amino acid sequences derived from mutant BAX and TGFβRII.

Figure 5:
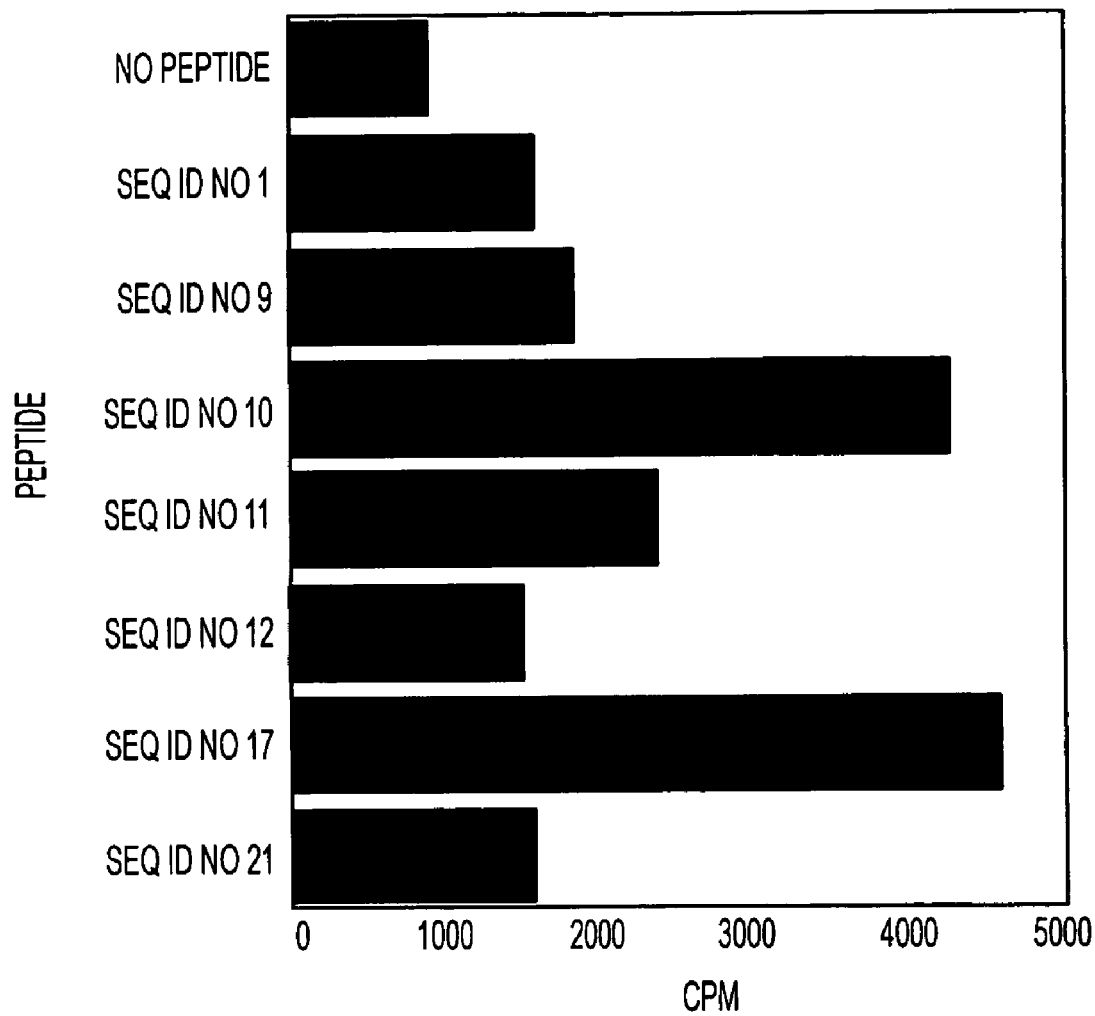

FIG. 5:

FIG. 5 further demonstrates the capability T cells from another pancreatic cancer patient to recognise and proliferate to different synthetic peptides derived from mutant BAX and mutant TGFβRII. The T cell line was obtained after expansion of T cells present in the ascites fluid of individual peptide in the mixture was 20 μM. After two weeks, and weekly thereafter, the bulk cultures were restimulated with autologous PBMCs pulsed with 10–25 μM of the peptide mixture. After 4–5 restimulations the bulk cultures were tested in a standard proliferation assay with PBMCs alone or as a control or PBMCs pulsed with 25 μM of the peptides as antigen presenting cells (APCs).

Figure 2:
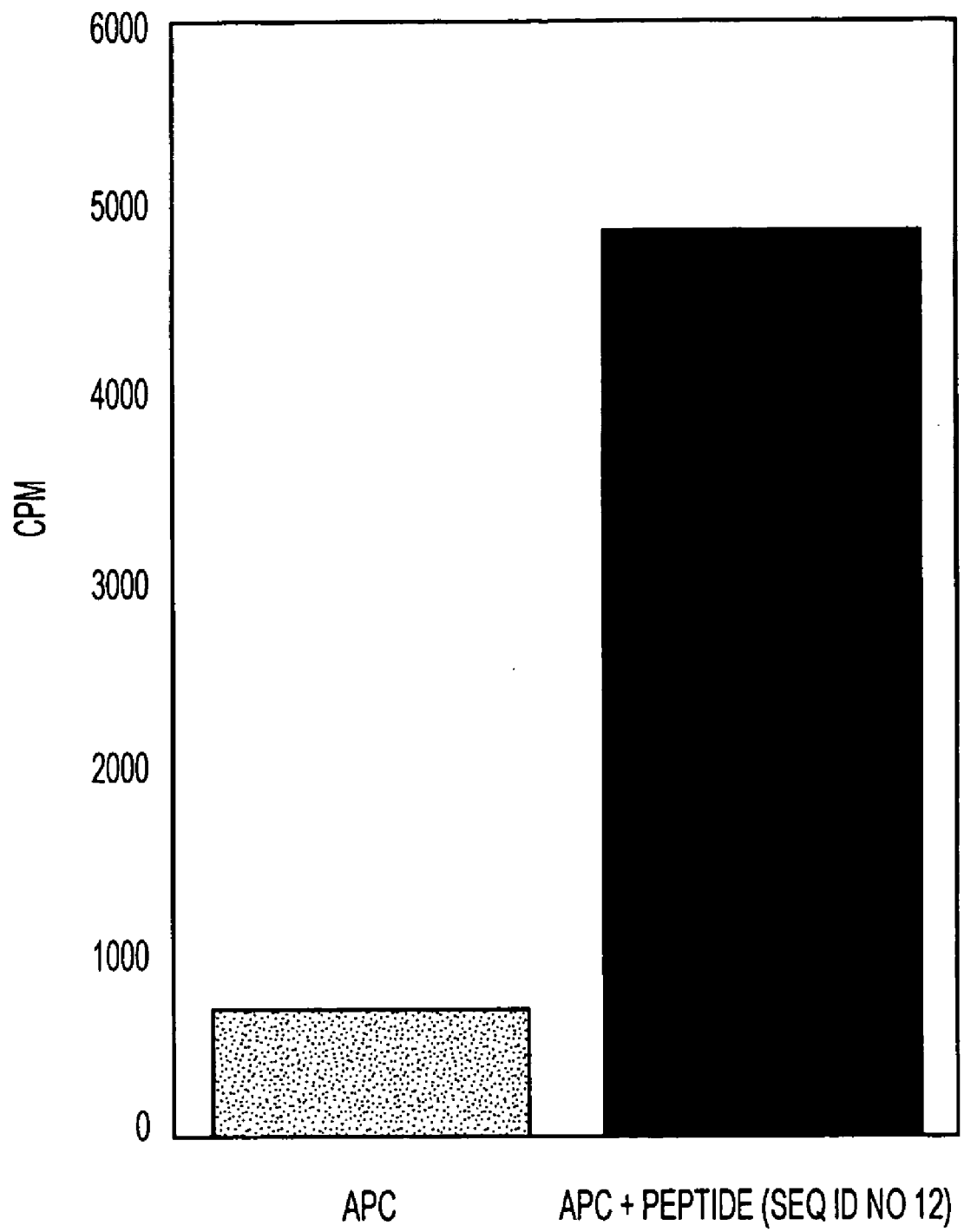

FIG. 2:

It has further been found that T cell clones can be generated against separate peptides of the mixture used in the bulk stimulation experiments. FIG. 2 shows the proliferation of T cell clone 521–2 which was obtained by cloning the bulk culture from donor 1 (FIG. 1) by seeding 5 cells per well in U-bottomed, 96-well microtiter plates and using autologous PBMCs pulsed with 25 μM of the mutant BAX peptide with seq id no 12 as feeder cells. Autologous B-lymphoblastoid cells were used as APCs in the proliferation assay.

Figure 3:
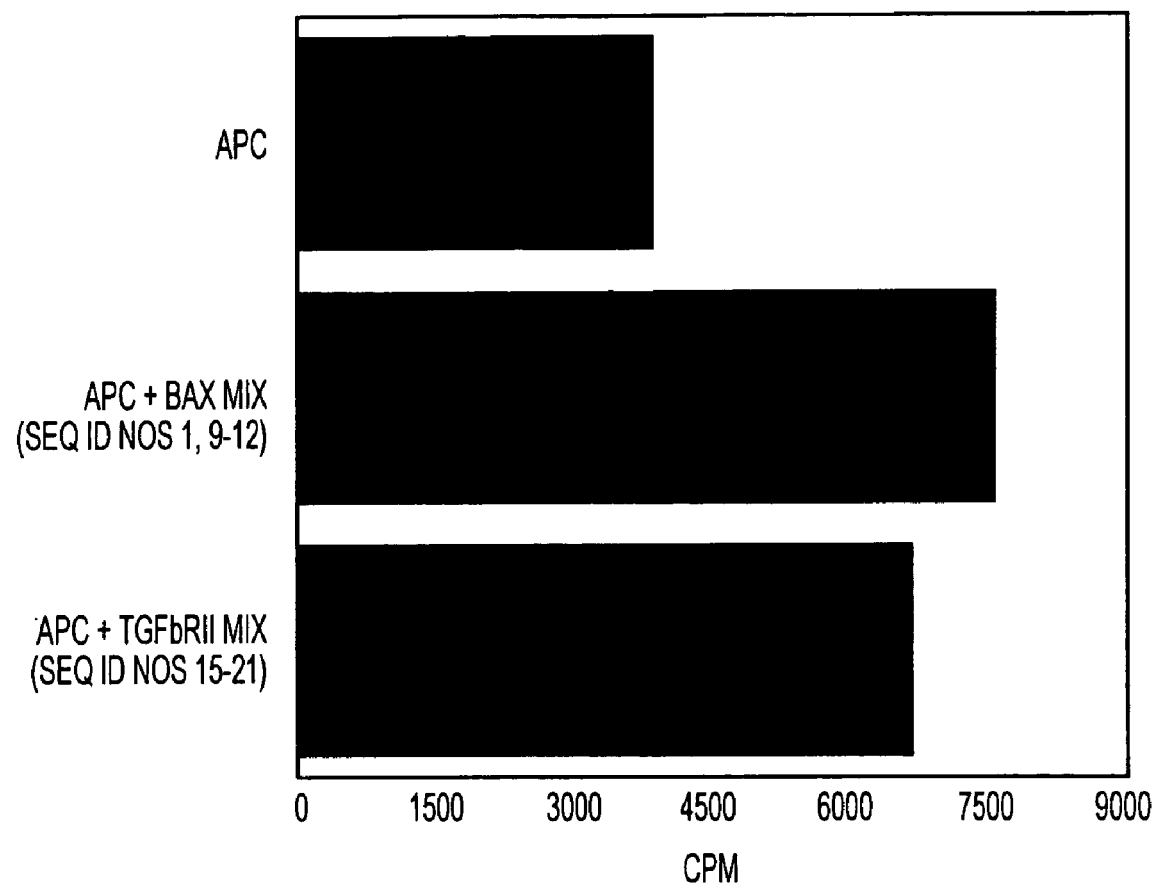

FIG. 3:

In figure three it is shown that mutant BAX peptides and mutant TGFβRII peptides can be used to stimulate T cells (PBMCs) from a patient with breast cancer. Dendritic cells (DCs) from the same cancer patient were used as APCs. The T cell stimulation (FIG. 3) was obtained by pulsing DCs separately with a mixture of mutant BAX peptides (seq id nos 1,9–12) and a mixture of mutant TGFβRII peptides (seq id nos 15–21) followed by addition of autologous PBMCs and 10 ng/ml tumour necrosis factor. The concentration of each peptide in the mixtures used for pulsing was 25 μM. The PBMCs and the DCs were obtained by leukapheresis from a patient with breast cancer who had been on a granulocyte colony stimulating factor (G-CSF) treatment. The CD34+ a patient with pancreatic adencarcinoma. The experiment was set up in the same way as described above. Data represent specific proliferation to the different synthetic peptides and values are expressed as the mean of triplicate cultures.

In order to investigate the T cell response from the latter pancreatic cancer patient, responding T cells were cloned. Peritoneal macrophages were irradiated (30 Gy) and plated 1×104 into U-bottomed 96-well plates (Costar) together with 25 μM of each peptide. T cell blasts were counted in a microscope and added 5 blasts per well together with 100 U/ml human recombinant interleukin-2 (rIL-2) (Amersham, Aylesbury, UK) in a total volume of 200 mL. After 14 days T cell clones were transferred onto 24-well plates (Costar) with 1 mg/mL phytohemagglutinin (PHA, Wellcome, Dartford, UK), 100 U/ml rIL-2 and allogeneic, irradiated PBMCs as feeder cells and screened for peptide specificity after 7 and 14 days.

Figure 6:
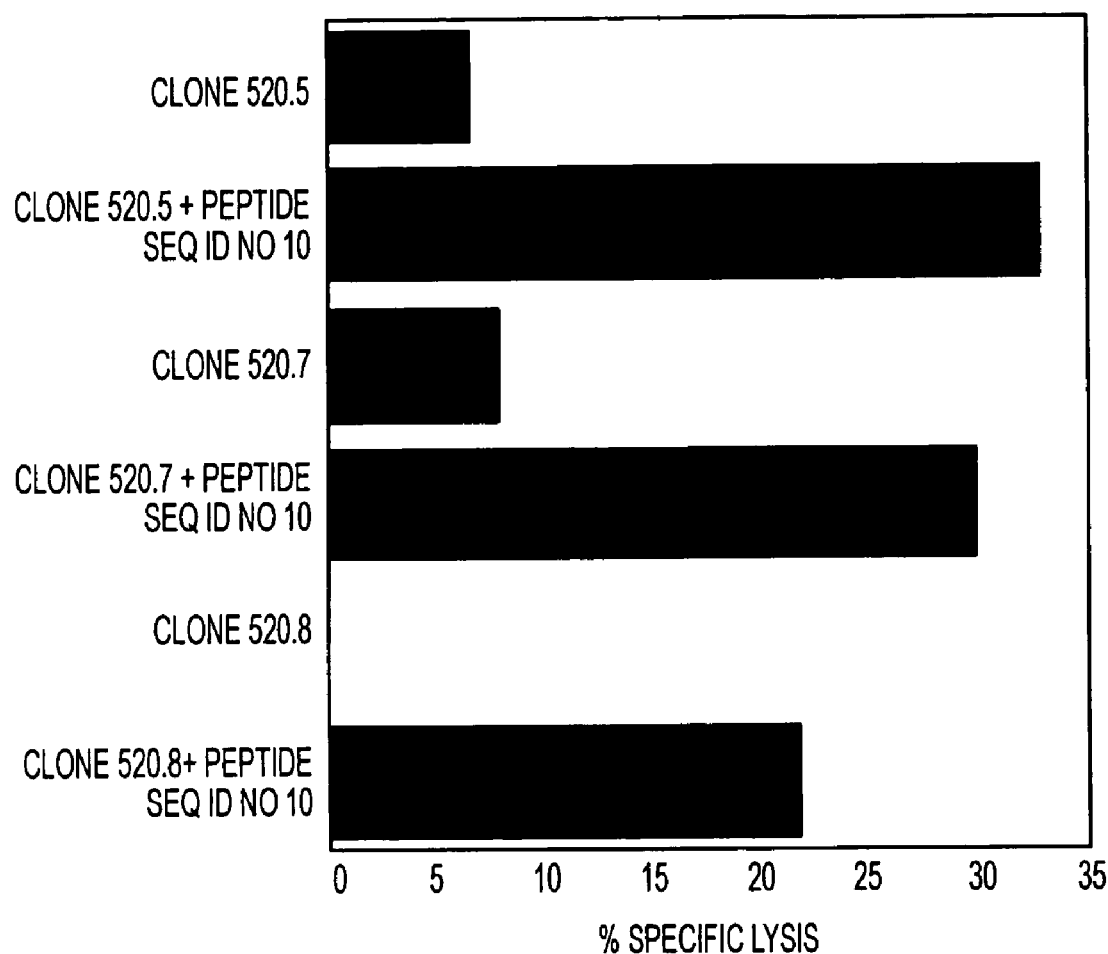

FIG. 6:

T cell clone 520.5, 520.7 and 520.8 were selected for further characterisation and express the cell surface phenotype CD3+, CD8+ and TcR+. FIG. 6 shows the recognition and cytotoxicity of T cell clone 520.5, 520.7 and 520.8 against peptide-pulsed autologous target cells pulsed with the seq id no 10 peptide. Autologous Epstein-barr virus transformed B-cells (EBV) were labelled with 3H-thymidine (9.25×104 Bq/ml) over night, washed once and plated 2500 cells per well in 96-well plates with or without 25 mM of synthetic peptide (seq id no 10) and 1% DMSO in medium. After 30 minutes incubation at 37° C. the plates were washed before addition of T cells. The plates were further incubated at 37° C. for 4 hours and then harvested before counting in a liquid scintillation counter (Packard Topcount). Data represent percent specific lysis of 3H-thymidine labelled peptide pulsed target cells at an effector/target ratio of 10/1. Values are expressed as the mean of triplicate cultures. These results demonstrate that the three different T cell clones obtained from ascites fluid of a pancreatic carcinoma patient, exhibit specific cytotoxicity of autologous EBV targets pulsed with the relevant peptide (seq id no 10) derived from mutant BAX.

Figure 7:
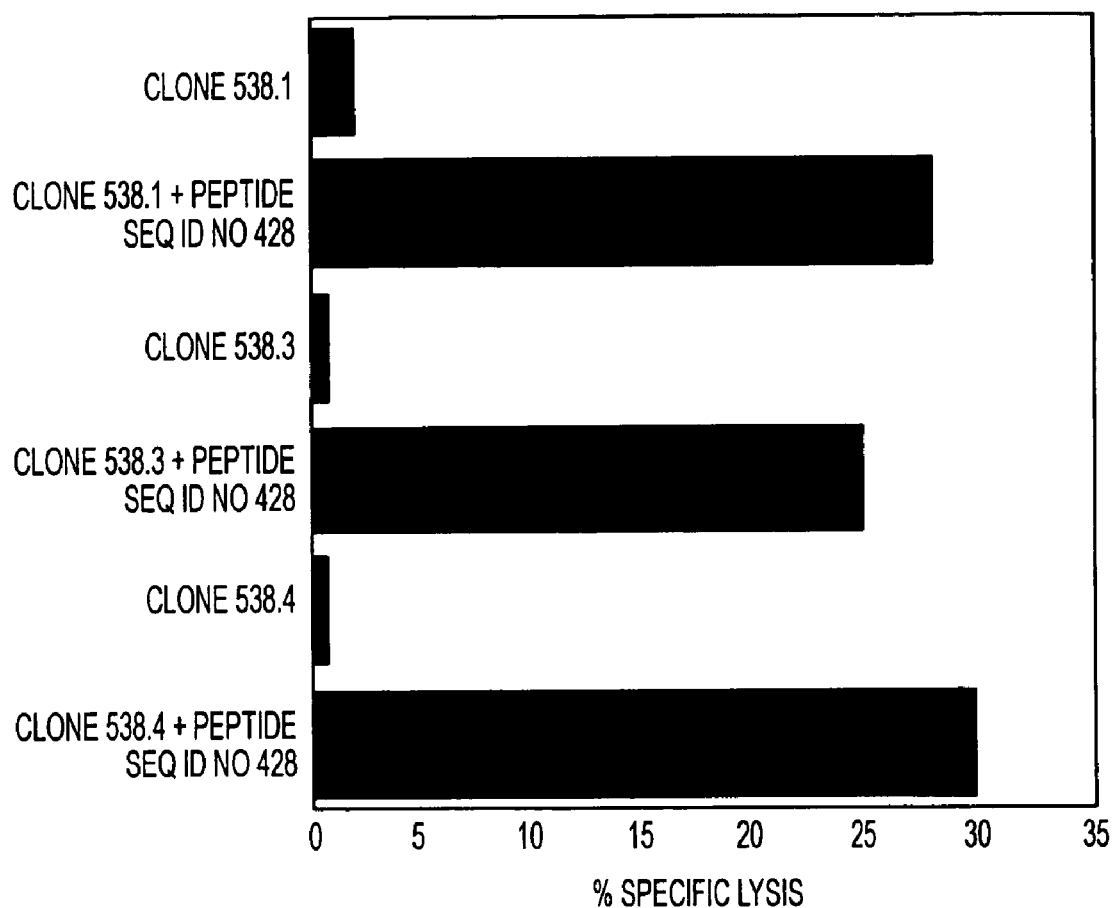

FIG. 7:

FIG. 7 shows the cytolytic properties of three different T cell clones obtained from the same patient. These T cell clones were cultured and expanded as described above, but they were generated against a synthetic peptide the seq id no 17 peptide carrying amino acid sequences derived from mutant TGFβRII. T cell clone 538.1, 538.3 and 538.4 all show the cell-surface phenotype CD3+, CD8+ and TcR+. The experimental conditions were as described above (FIG. 6). Data represent percent specific lysis of 3H-thymidine labelled peptide pulsed target cells pulsed with the seq id no 428 peptide at an effector/target ratio of 10/1. Values are expressed as the mean of triplicate cultures. These results demonstrate that the three different T cell clones obtained from ascites fluid of a pancreatic carcinoma patient, exhibit specific cytotoxicity of autologous EBV targets pulsed with the relevant peptide (seq id no 428) derived from mutant TGFβRII.

Figure 8:
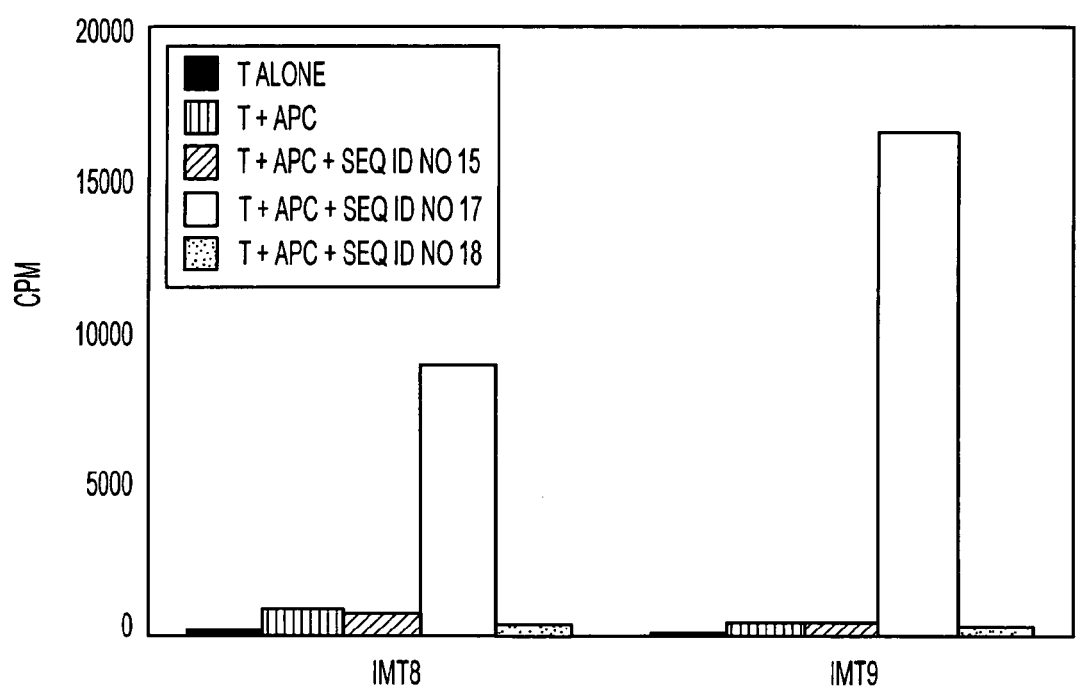

FIG. 8:

FIG. 8 shows the specificity of two CD4+ T cell clones, IMT8 and IMT9, obtained from a tumour biopsy taken from a patient with an adenocarcinoma localised to the proximal colon. Immunohistochemistry revealed that the patient had an abundant infiltrate of predominantly CD4+ T cells, many of which carried activation markers. In areas of CD4 T cell infiltration islands of HLA DR positive tumour cells were observed. The T cell clones were obtained from the component of tumour infiltrating lymphocytes which grew out of the biopsy following culture in medium containing 15 U/ml of recombinant human IL-2 for 16 days. The T cells from this culture were cloned by limiting dilution (1 cells/well) in Terasaki plates with irradiated peptide pulsed APC and 100 U/ml of IL-2. Pulsing of autologous APC was performed with a mixture of the TGFβRII frameshift peptides with sequence identity no. 15, 17 and 18 at 1 μg/ml of each peptide in the presence of 3 μg/ml of purified human β2 microglobulin and 10 ng/ml of recombinant human TNFα for 3 hrs at 37° C. Of the 14 clones that could be expanded preliminary tests showed that two of the clones were reactive with the peptide mixture used for cloning. After expansion the clones were screened for reactivity with the single peptides in a standard proliferative assay. The results show that IMT8 and IMT9 both react specifically with the TGFβRII frameshift peptide with seq. id. no. 17, no reactivity was observed with the two other frameshift peptides tested.

The figure (FIG. 8) depicts the results of conventional T cell proliferative assays, where cloned T cells (5×10$^4$) and irradiated APC (5×10$^4$) were cocultured for 3 days in triplicates before harvesting. To measure the proliferative capacity of the cultures, $^3$H-thymidine (3.7×10$^4$ Bq/well) was added to the culture overnight before harvesting) Values are given as mean counts per minute (cpm) of the triplicates.

Figure 9:
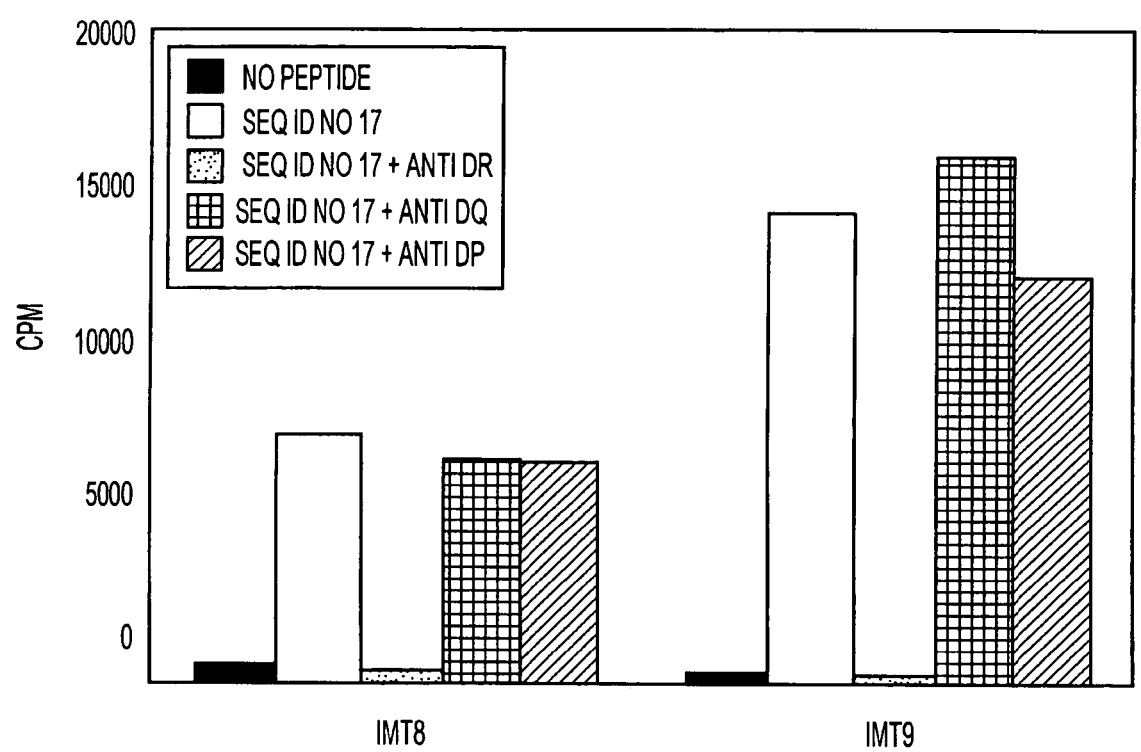

FIG. 9:

FIG. 9 demonstrates that the specific reactivity of the two T cell clones IMT8 and IMT9 against the peptide with seq. id.no. 17 is completely blocked by treatment of the cells with an antibody that specifically binds to HLA-DR molecules, since the reactivity after blocking is the same as the background reactivity of the clones with APC in the absence of the peptide. On the other hand antibodies to the HLA class II isotypes HLA-DQ and -DP failed to block the reactivity of the clones with peptide pulsed APC. This experiment unequivocally identifies HLA-DR as the molecule responsible to present the peptide to these two T cell clones. Antibody blocking experiments were performed using the homozygous EBV transformed cell line 9061 (IHWS9 nomenclature) as APC. The APC were pulsed with peptide at a concentration of 15 µg/1 ml for 1 hr at 37° C. before addition of blocking antibodies L243 (pan-DR antibody), SPVL3 (pan-DQ antibody) and B7.21 (pan-DP antibody) at 10 µg/ml. Unpulsed APC and APC pulsed with peptide in the absence of blocking antibody served as negative and positive controls respectively. Results are expressed as in FIG. 8.

Figure 10:
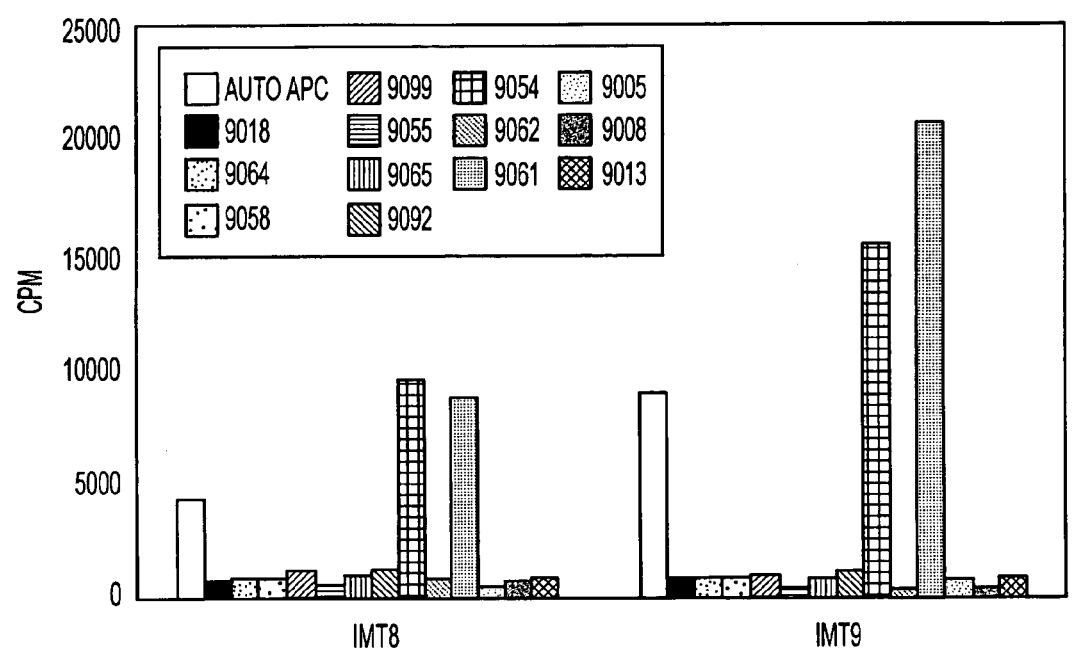

FIG. 10:

The patient IMT was HLA typed and turned out to be HLA: A1,2; B7,8; DR3,14; DQ1,2. To determine which of the HLA-DR molecules that were responsible for presentation of the peptide with seq. id. no. 17, a panel of HLA workshop derived homozygous BCL cell lines were obtained and pulsed with the peptide with seq. id. no. 17. FIG. 10 describes the identification of HLA-DR14 (DRA*0102, DRB*1401) as the HLA-DR molecule responsible for presentation of the peptide with seq. id. no. 17 to the T cell clones IMT8 and IMT9. A specific proliferative response was observed when peptide was presented by the autologous EBV transformed cell line (Auto APC) and by cell lines 9054 (EK) and 9061 (31227ABO), both of which expressed DR14 as the only DR molecule on their surface. The homozygous cell line gave higher responses, reflecting a higher level of expression of the relevant class II/peptide complexes due to the effect of a double dose of the genes encoding this DR molecule. No response was obtained when the peptide was presented by cell lines expressing HLA-DR3 (9018, LOO81785), which represents the other DR molecule expressed by the patients APC, nor by irrelevant HLA-DR molecules. The experiment was performed as described in FIG. 9, with the exception that no antibody blocking was performed. Results are expressed as in FIG. 8.

Figure 11:
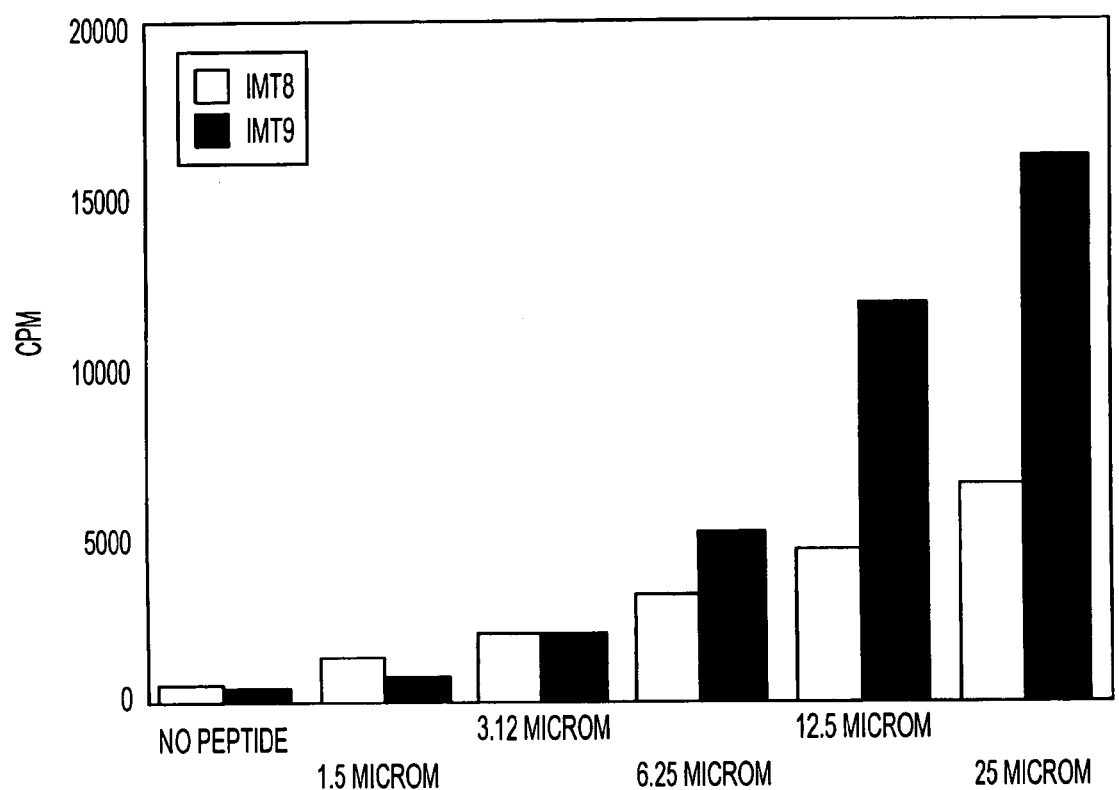

FIG. 11:

FIG. 11 describes the dose response curves obtained by pulsing the cell line 9054 with increasing concentrations of the peptide with seq. id. no. 17. Both IMT 8 and IMT9 demonstrate a dose dependent increase in the proliferative response to the peptide. Results were performed as described in FIGS. 9 and 10 with the peptide concentrations indicated on the Figure (FIG. 11). Results are expressed as in FIG. 8.

Figure 12:
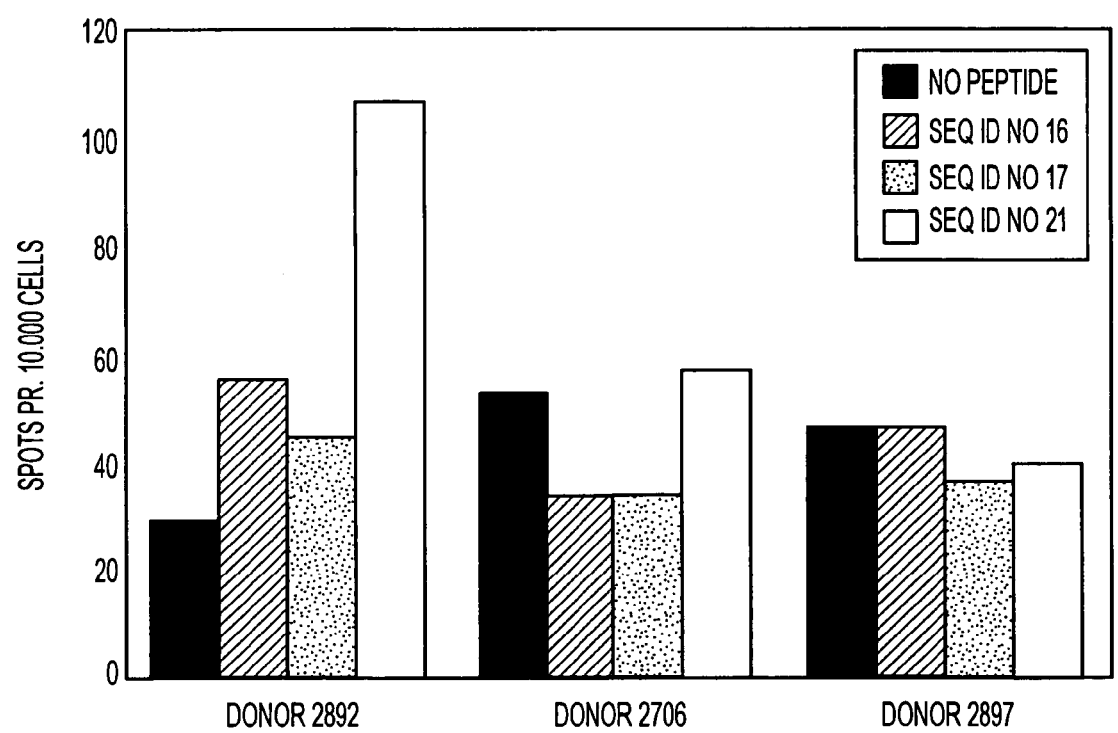

FIG. 12:

FIG. 12 describes the reactivity of a cell line generated by in vitro stimulation of T cells isolated from peripheral blood from a healthy blood donor (Donor 2892) by weekly stimulation with irradiated autologous dendritic cells pulsed with the peptides with sequence identity numbers 16, 17 and 21. A specific response above background values was obtained when the T cells were co-incubated with autologous dendritic cells pulsed with the peptide with seq. id. no. 21. No activity could be detected in the culture after the first and second in vitro stimulation. These data demonstrate that the T cell repertoire of normal individuals contain a few precursor cells that have the capacity to recognise this frameshift peptide derived from a mutation in TGFβRII that does not occur in normal people. In two other blood donors (#2706 and #2896), the level of precursor cells with the relevant specificity was too low to be detected. The results are expressed as spots per $10^4$ T cells tested in a conventional IFNg ELISPOT assay. This assay enumerates the number of cells present in a mixture of cells that are capable of specifically reacting with a defined antigen. Briefly $10^7$ T cells (non adherent cells) were stimulated weekly with 2–5×$10^6$ irradiated peptide pulsed autologous dendritic cells (DC) as APC. The DC were generated from the adherent cell population by culture for one week in recombinant human GM-CSF and IL-4 according to standard protocols as described in the literature. After peptide pulsing overnight at 15 µg/ml of peptide, full maturation of the DC was obtained by culture with recombinant TNFα. ELISPOT was performed according to standard published protocols using $10^4$ cultured T cells per well in duplicate and $10^4$ peptide pulsed or unpulsed DC as APC. The results are expressed as mean number of spots per $10^4$ T cells.

Figure 13:
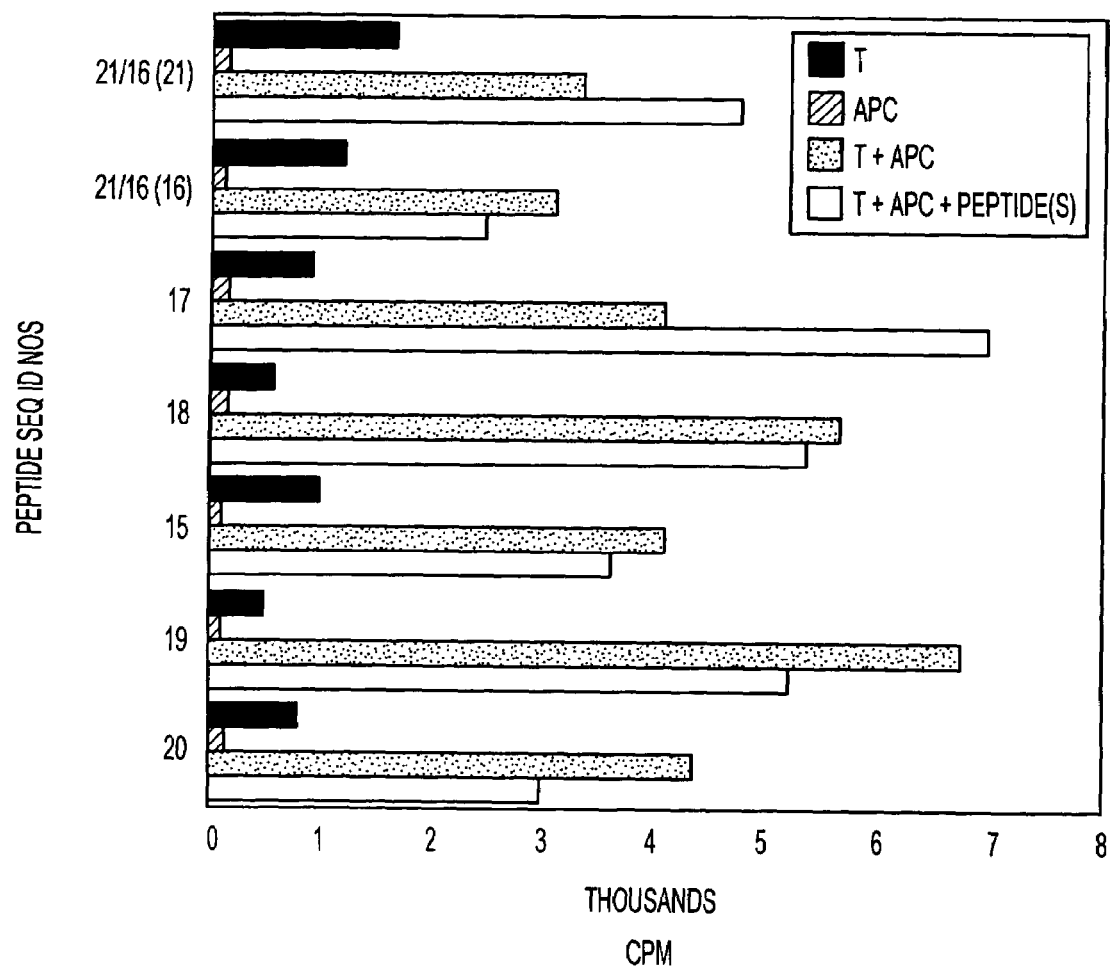

FIG. 13:

FIG. 13 shows the results of in vitro stimulation of T cells from a healthy blood donor (Donor 322) with peptides with sequence identity number 15–21. In vitro culture was performed as described in FIG. 12. A proliferative response above background values was seen when the T cell culture primed with a mixture of the peptides with seq. id. no. 16 and 21 was stimulated with peptide 21 and the culture primed with the peptide with seq. id. no. 17 was stimulated with the same peptide. These results demonstrate that normal blood donors have small numbers of circulating T cells specific for these frameshift peptides, and that it is possible to expand these cells in culture by stimulation with frameshift peptides. These results also confirmed the results shown in FIGS. 8–11, demonstrating that the peptide with seq. id. no. 17 is immunogenic in humans, and indicate that the peptide with seq. id. no. 21 may also be used as a cancer vaccine in humans. The results are expressed as described in FIG. 8.

Figure 14:
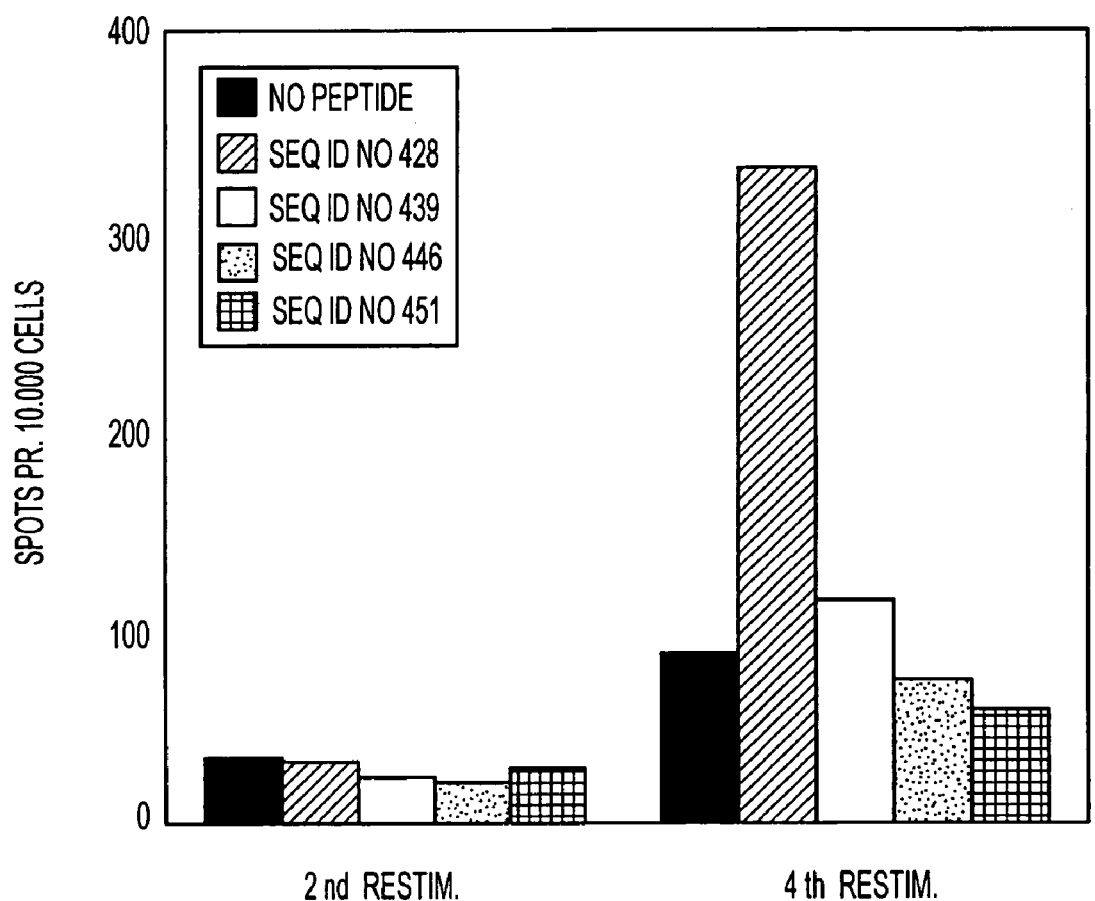

FIG. 14:

The results shown in FIG. 14 demonstrate that CD8+ T cells specific for HLA class I epitopes can be generated from T cells present in the T cell repertoire of a healthy blood donor (donor 905). No reactivity above background was seen with any of the peptides after the second round of in vitro restimulation. After the fourth restimulation, the frequency of T cells specific for the peptide with seq. id. no. 428 had increased from undetectable levels to approximately 2.5% of the cells. These results demonstrate that CTL precursors of the CD8+ phenotype are present in the unprimed T cell repertoire of healthy blood donors. Such T cells may be expanded in vitro by specific stimulation with the peptide with seq. id. no. 428. This forms the basis for using this peptide as a cancer vaccine to elicit cytotoxic T cells specific for framshift peptides in cancer patient having such mutations. T cells were generated by weekly restimulation of T cells isolated from peripheral blood and stimulated with peptide pulsed autologous DC as described in FIG. 12, with the exception that Il-7 and Il-2 was added during culture according to standard procedures for generating cytotoxic T cells (CTL) of the CD8 phenotype. The peptides used were peptides with sequence identity number 428, 439, 446 and 451. Cells were tested in ELISPOT assay as described in FIG. 12. The results are expressed as described in FIG. 12.

The peptide with seq. id. no. 17 was selected and designed to contain binding motifs for both several HLA class I and HLA class II molecules. These peptides thus contains epitopes both for CD4+ and CD8+ T cells, and was predicted to elicit both CD4 and CD8 T cell responses in cancer patient provided processing of the aberrant TGFβRII protein naturally occurring in cancer cells would take place and result in an overlapping peptide. This has now been proven for CD4 T cells by the results in FIGS. 8–11. These results have the following implication:

1) The results in FIG. 8 prove that the mutated form of TGFβRII Receptor which occurs in a high proportion of cancer patients with defects in their mismatch repair known. The results in FIG. 8 demonstrate that one component of the T cells constituting the population of tumour infiltrating lymphocytes in this patients tumour is specific 3) It follows from this observation that processing of the non-functional form of the TGFβRII Receptor that is formed by the common frameshift mutation is processed. This taken up by a professional APC or both.

4) The results in FIG. 8 also indicate that the peptide with seq. id. no. 17 is capable of binding to an HLA class II That this is the case is demonstrated by the results of the experiment shown in FIG. 9. Here it is shown that the specific response against the peptide with seq. id. no. 17 is homozygous Epstein Barr virus (EBV) transformed B Cell Lines (BCL) covering the relevant HLA class II molecules present on the patients own APC, we were able to identify the class II molecule responsible for presentation of the tions taken from the same tumour biopsy, where we could show that activated CD4+ T cells were abundant in the proximity of tumour cells that had been induced to express responses are dose dependent.

5) Since these T cell clones were obtained by cloning T cells isolated from a tumour biopsy, another implication of 6) Since the peptide with seq. id. no. 17 is a tumour specific antigen, and since frameshift mutations giving rise to this peptide or peptides with overlapping sequences are or patients at high risk for developing cancer. Such T cell responses may potentially influence the growth of an existing tumour or prohibit regrowth of tumour after surgery and developing a cancer where this precise mismatch repair mutation will occur.

Synthesis appropriate side chain protection were used. The Fmoc-amino acids were activated for coupling as pentafluorophe-nyl esters or by using either TBTU or diisopropyl carbodi-protection was performed by 95% TFA containing appropriate scavengers. The peptides were purified and analysed by reversed phase (C18) HPLC. The identity of the peptides were synthesised by this method.

Several other well known methods can be applied by a person skilled in the art to synthesise the peptides.

In this Example, the BAX gene is used to illustrate the principle.

In each of the steps listed below, the 1st line is the gene

Step One:
   Normal BAX.

GTG . . .
P   V   . . .

ATG GGG GGG *AGG* CAC CCG AGC TGG CCC TGG ACC
$_G^C$ $_M$  G   G   G   T   R   A   G   P   G   P   G

Step Three:

$_M^{CC\ GGT}$  G   G   T   R   A   G   P   G   P   G

...T CGG GGA CGA ACT GGA CAG *TAA*
S   Q   A   H   R   G   R   T   G   Q   stop

Step Four:
   1G inserted in gene sequence.

ATG GGG GGG *GGA* GGC ACC CGA GCT GGC CCT GGA
$_G^{CC}$ $_M$  G   G   G   T   R   A   G   P   G   P

GGT GCC TCA GGA TGC GTC CAC CAA GAA GCT
$_G^{AG\ CGA}$  A   S   G   C   V   H   Q   E   A   E   R

Step Five:
  2G inserted in gene sequence

```
          M   G   G   R   H   P   S   W   P   W   T
      CGG TGC CTC AGG ATG CGT CCA CCA AGA AGC TGA
       R   C   L   R   M   R   P   P   R   S  stop
```

In each of the steps listed below, the 1st line is the gene sequence and 2nd line is amino acid sequence.

In the steps 2–5, the outlined sequences represent the

GAA AAA AAA AAG CCT GGT GAG ACT TTC TTC ATG TGT

Step Two:
  1A deleted from gene sequence.

$G_E^{TT}$ K K S L V R L S S C V
CCT GTA GCT CTG ATG AGT GCA ATG ACA ACA TCA $T_S^{GT}$ Q K N I T P A I L T C
T G C TAG 2A deleted from gene sequence.

Step Four:
  1A inserted in gene sequence.

Step Five:
  2A inserted in gene sequence.

```
    TCT TCT CAG AAG AAT ATA ACA CCA GCA ATC CTG
```
$A_S^{CT}$ S Q K N I T P A I L T

TGC TAG
     C   C  stop

Thus the peptides of the invention may be used in a method for the treatment of cancers with cancer cells harbouring genes with frameshift mutations, which treatment comprises administering at least one peptide of the present invention in vivo or ex vivo to a human patient in need of such treatment.

In another embodiment the peptides of the invention may be used to vaccinate a human being disposed for cancers with cancer cells harbouring genes with frameshift mutations, by administering at least one peptide of the present invention to said human being.

It is further considered to be an advantage to administer to a human individual a mixture of the peptides of this invention, whereby each of the peptides of the invention can bind to different types of HLA class I and/or class II molecules of the individual.

It is further anticipated that the power of an anticancer vaccine or peptide drug as disclosed in the above mentioned PCT/NO92/00032 application, can be greatly enhanced if the peptides of the present invention were included. Thus in another embodiment of the present invention peptides of the present invention are administered together with, either simultaneously or in optional sequence, with the peptides disclosed in PCT/NO92/00032.

It is considered that the peptides may be administered together, either simultaneously or separately, with compounds such as cytokines and/or growth factors, i.e. interleukin-2 (IL-2), interleukin-12 (IL-12), granulocyte macrophage colony stimulating factor (GM-CSF), Flt-3 ligand or the like in order to strengthen the immune response as known in the art.

The peptides according to the present invention can be used in a vaccine or a therapeutical composition either alone or in combination with other materials, such as for instance standard adjuvants or in the form of a lipopeptide conjugate which as known in the art can induce high-affinity cytotoxic T lymphocytes, (K. Deres, Nature, Vol. 342, (November 1989)).

The peptides according to the present invention may be useful to include in either a peptide or recombinant fragment based vaccine.

The peptides according to the present invention can be included in pharmaceutical compositions or in vaccines together with usual additives, diluents, stabilisers or the like as known in the art.

According to this invention, a pharmaceutical composition or vaccine may include the peptides alone or in combination with at least one pharmaceutically acceptable carrier or diluent.

Further a vaccine or therapeutical composition can comprise a selection of peptides which are fragments of the mutant proteins arising from insertion or deletion of bases in a repeat sequence of the gene.

Further a vaccine composition can comprise at least one

Further a vaccine composition can comprise at least one peptide selected for one cancer, which vaccine would be administered to a person belonging to a high risk group for example as a mixture of peptides giving rise to T cell immunity against various common cancers connected with frameshift mutation genes.

each other to form larger polypeptides or even cyclic polypeptides.

A cancer therapy according to the present invention may which the patient is afflicted.

Further, the frameshift mutant peptides of this invention may be administered to a patient by various routes including but not limited to subcutaneous, intramuscular, intradermal The peptides may be administered at single or multiple injection sites to a patient in a therapeutically or prophylactically effective amount.

The peptides of this invention may be administered only

The peptides of this invention can be administered in an amount in the range of 1 microgram (1 μg) to 1 gram (1 g) to an average human patient or individual to be vaccinated.

The invention further encompasses DNA sequences which encodes a frameshift mutation peptide.

The invention additionally encompasses isolated DNA prophylaxis of cancers associated with frameshift mutations in the genes.

The peptides according to this invention may be adminbe delivered together with cytokines, such as IL-2, and/or other co-stimulatory molecules. The cytokines and/or co-stimulatory molecules may themselves be delivered in the These can take the form of hexameric motifs containing methylated CpG, according to the formula: 5'-purine-purine-CG-pyrimidine-pyrimidine-3'. Our DNA vaccines may therefore incorporate these or other ISS in the DNA encodtages of DNA vaccination is provided by Tighe et al (1998, *Immunology Today*, 19 (2), 89–97).

In one embodiment, the DNA sequence encoding the

Normal BAX.
AT<u>G GGG GGG G</u>AG GCA CCC GAG CTG GCC CTG GAC CCG
GTG

C<sup>G G</sup>

T G C   C T C   A G G   A T G   C G T   C C A   C C A   A G A   A G C   <u>TGA</u>1

G C C   T C A   G G A   T G C   G T C   C A C   C A A   G A A   G C T   G A G
C<sup>G A   G T G</sup>

T C T   C A A   G C G   C A T   C G G   G G A   C G A   A C T   G G A   C A G   TAA
C<sup>C C</sup>

G G T   G C C   T C A   G G A   T G C   G T C   C A C   C A A   G A A   G C T
C<sup>A G   C G A</sup>

2G inserted in BAX gene sequence.
ATG GGG GGG GGG <u>AGG</u> CAC CCG AGC TGG CCC TGG ACC
CGG TGC CTC AGG ATG CGT CCA CCA AGA AGC TGA Normal TGFβRII gene.

1A deleted from TGFβRII gene sequence.
G<u>AA AAA AAA A</u>G C   C T G   G T G   A G A   C T T   T C T   T C A   T G T
G<sup>T T</sup>

T<sup>G T</sup>

T G C   <u>TAG</u>

G<u>AA AAA AAA AAA</u>   G C C   T G G   <u>TGA</u>

2A inserted in TGFβRII gene sequence.
GAA AAA AAA AAA ACC CTC CTC ACA CTT TCT TCA TCT
GTT CCT GTA GCT CTG ATG AGT GCA ATG ACA
A<sup>CA T C A</sup>

T C T   T C T   C A G   A A G   A A T   A T A   A C A   C C A   G C A   A T C   C T G
A<sup>C T</sup>

T G T   T G C   <u>TAG</u>

The invention further encompasses vectors and plasmids comprising a DNA sequence encoding a frameshift mutant peptide. The vectors include, but are not limited to *E. Coli* plasmid, a *Listeria* vector and recombinant viral vectors. Recombinant viral vectors include, but are not limited to orthopox virus, canary virus, capripox virus, suipox virus, vaccinia, baculovirus, human adenovirus, SV40, bovine papilloma virus and the like comprising the DNA sequence encoding a frameshift mutant peptide.

It is considered that an anticancer treatment or prophylaxis may be achieved also through the administration of an effective amount of a recombinant virus vector or plasmid comprising at least one insertion site containing a DNA sequence encoding a frameshift mutant peptide to a patient, whereby the patient's antigen presenting cells are turned into host cells for the vector/plasmid and presentation of HLA/ frameshift mutation peptide complex is achieved.

A person skilled in the art will find other possible use combinations with the peptides of this invention, and these are meant to be encompassed by the present claim.

The peptides according to this invention may be produced by conventional processes as known in the art, such as chemical peptide synthesis, recombinant DNA technology or protease cleavage of a protein or peptide encoded by a frameshift mutated gene. One method for chemical synthesis is elucidated in the description below.

In order for a cancer vaccine and methods for specific cancer therapy based on specific T cell immunity to be effective, three conditions must be met:
1. The peptides used must correspond, either in their full length or after processing by antigen presenting cells, to the processed mutant protein fragment as presented by a HLA Class I and/or class II molecule on the cancer cell or other antigen presenting cells,
2. The peptides used must be bound to a HLA Class I and/or Class II molecule in an immunogenic form, and
3. T-cells capable of recognising and responding to the HLA/peptide complex must be present in the circulation of the human being.

It has been established that all these conditions are met for some representative peptides according to the present invention. The peptides according to the present invention give rise to specific T cell immune responses in vitro. It has been established that the peptides according to this invention correspond to processed mutant protein fragments. This is exemplified with peptides corresponding to fragments of transformed mutant BAX and TGFβRII peptides.

Through the present invention the following advantages are achieved:

- It offers a possibility to treat patients suffering from cancers arising from frame-shift mutations in their genes, most of which cancers known at present do not have any good treatment alternatives.
- It offers a possibility to vaccinate prophylaxtically humans carrying genetic dispositions or belonging to other high risk groups.
- It offers a possibility to prepare a combination treatment for a specific cancer, such as for instance colorectal or pancreatic cancers, wherein the cancer commonly is associated with either a frameshift mutation or a point mutation in the genes.
- Since described frameshift mutations occurs in a large variety of cancers it will be possible to use this peptides in combination with established vaccines and future vaccines to obtain a multiple targetting treatment.
- Likewise patients suffering from cancers associated with multiple frameshift mutations in genes can be treated more efficiently through a combination treatment.

SEQUENCE LISTING

```
<160> NUMBER OF SEQ ID NOS: 459

<210> SEQ ID NO 1
<211> LENGTH: 18
<212> TYPE: PRT
<213> ORGANISM: Homo sapiens

<400> SEQUENCE: 1

Arg His Pro Ser Trp Pro Trp Thr Arg Cys Leu Arg Met Arg Pro Pro
1               5                   10                  15

Arg Ser

<210> SEQ ID NO 2
<211> LENGTH: 31
<212> TYPE: PRT
<213> ORGANISM: Homo sapiens

<400> SEQUENCE: 2

Gly Thr Arg Ala Gly Pro Gly Pro Gly Ala Ser Gly Cys Val His Gln
1               5                   10                  15

Glu Ala Glu Arg Val Ser Gln Ala His Arg Gly Arg Thr Gly Gln
            20                  25                  30

<210> SEQ ID NO 3
<211> LENGTH: 32
<212> TYPE: PRT
<213> ORGANISM: Homo sapiens
```

-continued

```
<400> SEQUENCE: 3

Gly Gly Thr Arg Ala Gly Pro Gly Pro Gly Ala Ser Gly Cys Val His
1               5                   10                  15

Gln Glu Ala Glu Arg Val Ser Gln Ala His Arg Gly Arg Thr Gly Gln
            20                  25                  30

<210> SEQ ID NO 4
<211> LENGTH: 19
<212> TYPE: PRT
<213> ORGANISM: Homo sapiens

<400> SEQUENCE: 4

Gly Arg His Pro Ser Trp Pro Trp Thr Arg Cys Leu Arg Met Arg Pro
1               5                   10                  15

Pro Arg Ser

<210> SEQ ID NO 5
<211> LENGTH: 28
<212> TYPE: PRT
<213> ORGANISM: Homo sapiens

<400> SEQUENCE: 5

Ile Gln Asp Arg Ala Gly Arg Met Gly Gly Arg His Pro Ser Trp Pro
1               5                   10                  15

Trp Thr Arg Cys Leu Arg Met Arg Pro Pro Arg Ser
            20                  25

<210> SEQ ID NO 6
<211> LENGTH: 19
<212> TYPE: PRT
<213> ORGANISM: Homo sapiens

<400> SEQUENCE: 6

Ile Gln Asp Arg Ala Gly Arg Met Gly Gly Arg His Pro Ser Trp
1               5                   10                  15

Pro Trp Thr

<210> SEQ ID NO 7
<211> LENGTH: 42
<212> TYPE: PRT
<213> ORGANISM: Homo sapiens

<400> SEQUENCE: 7

Ile Gln Asp Arg Ala Gly Arg Met Gly Gly Gly Thr Arg Ala Gly
1               5                   10                  15

Pro Gly Pro Gly Ala Ser Gly Cys Val His Gln Glu Ala Glu Arg Val
            20                  25                  30

Ser Gln Ala His Arg Gly Arg Thr Gly Gln
        35                  40

<210> SEQ ID NO 8
<211> LENGTH: 19
<212> TYPE: PRT
<213> ORGANISM: Homo sapiens

<400> SEQUENCE: 8

Ile Gln Asp Arg Ala Gly Arg Met Gly Gly Gly Thr Arg Ala Gly Pro
1               5                   10                  15

Gly Pro Gly
```

```
<210> SEQ ID NO 9
<211> LENGTH: 22
<212> TYPE: PRT
<213> ORGANISM: Homo sapiens

<400> SEQUENCE: 9

Ile Gln Asp Arg Ala Gly Arg Met Gly Gly Arg His Pro Ser Trp Pro
1               5                   10                  15

Trp Thr Arg Cys Leu Arg
            20

<210> SEQ ID NO 10
<211> LENGTH: 22
<212> TYPE: PRT
<213> ORGANISM: Homo sapiens

<400> SEQUENCE: 10

Ala Ser Gly Cys Val His Gln Glu Ala Glu Arg Val Ser Gln Ala His
1               5                   10                  15

Arg Gly Arg Thr Gly Gln
            20

<210> SEQ ID NO 11
<211> LENGTH: 22
<212> TYPE: PRT
<213> ORGANISM: Homo sapiens

<400> SEQUENCE: 11

Gly Gly Thr Arg Ala Gly Pro Gly Pro Gly Ala Ser Gly Cys Val His
1               5                   10                  15

Gln Glu Ala Glu Arg Val
            20

<210> SEQ ID NO 12
<211> LENGTH: 22
<212> TYPE: PRT
<213> ORGANISM: Homo sapiens

<400> SEQUENCE: 12

Ile Gln Asp Arg Ala Gly Arg Met Gly Gly Gly Gly Thr Arg Ala Gly
1               5                   10                  15

Pro Gly Pro Gly Ala Ser
            20

<210> SEQ ID NO 13
<211> LENGTH: 34
<212> TYPE: PRT
<213> ORGANISM: Homo sapiens

<400> SEQUENCE: 13

Ser Leu Val Arg Leu Ser Ser Cys Val Pro Val Ala Leu Met Ser Ala
1               5                   10                  15

Met Thr Thr Ser Ser Ser Gln Lys Asn Ile Thr Pro Ala Ile Leu Thr
            20                  25                  30

Cys Cys

<210> SEQ ID NO 14
<211> LENGTH: 44
<212> TYPE: PRT
<213> ORGANISM: Homo sapiens
```

-continued

```
<400> SEQUENCE: 14

Ser Pro Lys Cys Ile Met Lys Glu Lys Lys Ser Leu Val Arg Leu Ser
1               5                   10                  15

Ser Cys Val Pro Val Ala Leu Met Ser Ala Met Thr Thr Ser Ser Ser
            20                  25                  30

Gln Lys Asn Ile Thr Pro Ala Ile Leu Thr Cys Cys
        35                  40

<210> SEQ ID NO 15
<211> LENGTH: 19
<212> TYPE: PRT
<213> ORGANISM: Homo sapiens

<400> SEQUENCE: 15

Pro Lys Cys Ile Met Lys Glu Lys Lys Ser Leu Val Arg Leu Ser
1               5                   10                  15

Ser Cys Val

<210> SEQ ID NO 16
<211> LENGTH: 23
<212> TYPE: PRT
<213> ORGANISM: Homo sapiens

<400> SEQUENCE: 16

Ala Leu Met Ser Ala Met Thr Thr Ser Ser Ser Gln Lys Asn Ile Thr
1               5                   10                  15

Pro Ala Ile Leu Thr Cys Cys
            20

<210> SEQ ID NO 17
<211> LENGTH: 23
<212> TYPE: PRT
<213> ORGANISM: Homo sapiens

<400> SEQUENCE: 17

Ser Leu Val Arg Leu Ser Ser Cys Val Pro Val Ala Leu Met Ser Ala
1               5                   10                  15

Met Thr Thr Ser Ser Ser Gln
            20

<210> SEQ ID NO 18
<211> LENGTH: 22
<212> TYPE: PRT
<213> ORGANISM: Homo sapiens

<400> SEQUENCE: 18

Ser Pro Lys Cys Ile Met Lys Glu Lys Lys Ser Leu Val Arg Leu Ser
1               5                   10                  15

Ser Cys Val Pro Val Ala
            20

<210> SEQ ID NO 19
<211> LENGTH: 12
<212> TYPE: PRT
<213> ORGANISM: Homo sapiens

<400> SEQUENCE: 19

Ser Pro Lys Cys Ile Met Lys Glu Lys Lys Ala Trp
1               5                   10
```

```
<210> SEQ ID NO 20
<211> LENGTH: 12
<212> TYPE: PRT
<213> ORGANISM: Homo sapiens

<400> SEQUENCE: 20

Pro Lys Cys Ile Met Lys Glu Lys Lys Ala Trp
1               5                   10

<210> SEQ ID NO 21
<211> LENGTH: 19
<212> TYPE: PRT
<213> ORGANISM: Homo sapiens

<400> SEQUENCE: 21

Ala Met Thr Thr Ser Ser Ser Gln Lys Asn Ile Thr Pro Ala Ile Leu
1               5                   10                  15

Thr Cys Cys

<210> SEQ ID NO 22
<211> LENGTH: 9
<212> TYPE: PRT
<213> ORGANISM: Homo sapiens

<400> SEQUENCE: 22

Thr Val Gly Arg Pro His Ile Ser Cys
1               5

<210> SEQ ID NO 23
<211> LENGTH: 10
<212> TYPE: PRT
<213> ORGANISM: Homo sapiens

<400> SEQUENCE: 23

Lys Thr Val Gly Arg Pro His Ile Ser Cys
1               5                   10

<210> SEQ ID NO 24
<211> LENGTH: 18
<212> TYPE: PRT
<213> ORGANISM: Homo sapiens

<400> SEQUENCE: 24

Lys Gln Trp Glu Asp Pro Thr Ser Pro Ala Asn Val Ile Ala Leu Leu
1               5                   10                  15

Gln Thr

<210> SEQ ID NO 25
<211> LENGTH: 17
<212> TYPE: PRT
<213> ORGANISM: Homo sapiens

<400> SEQUENCE: 25

Gln Trp Glu Asp Pro Thr Ser Pro Ala Asn Val Ile Ala Leu Leu Gln
1               5                   10                  15

Thr

<210> SEQ ID NO 26
<211> LENGTH: 19
<212> TYPE: PRT
<213> ORGANISM: Homo sapiens
```

```
<400> SEQUENCE: 26

Gln Lys Thr Ile Lys Ser Thr Arg Lys Lys Thr Val Gly Arg Pro His
1               5                   10                  15

Ile Ser Cys

<210> SEQ ID NO 27
<211> LENGTH: 20
<212> TYPE: PRT
<213> ORGANISM: Homo sapiens

<400> SEQUENCE: 27

Gln Lys Thr Ile Lys Ser Thr Arg Lys Lys Thr Val Gly Arg Pro
1               5                   10                  15

His Ile Ser Cys
            20

<210> SEQ ID NO 28
<211> LENGTH: 28
<212> TYPE: PRT
<213> ORGANISM: Homo sapiens

<400> SEQUENCE: 28

Gln Lys Thr Ile Lys Ser Thr Arg Lys Lys Gln Trp Glu Asp Pro
1               5                   10                  15

Thr Ser Pro Ala Asn Val Ile Ala Leu Leu Gln Thr
            20                  25

<210> SEQ ID NO 29
<211> LENGTH: 27
<212> TYPE: PRT
<213> ORGANISM: Homo sapiens

<400> SEQUENCE: 29

Gln Lys Thr Ile Lys Ser Thr Arg Lys Lys Gln Trp Glu Asp Pro Thr
1               5                   10                  15

Ser Pro Ala Asn Val Ile Ala Leu Leu Gln Thr
            20                  25

<210> SEQ ID NO 30
<211> LENGTH: 34
<212> TYPE: PRT
<213> ORGANISM: Homo sapiens

<400> SEQUENCE: 30

Ala Ala Asp Leu Gln Gln Gln Phe Val His Phe Leu Asp Cys Trp Asp
1               5                   10                  15

Val Ser Ser Ile Pro Phe Thr Leu His Leu Pro Gln Ala Gln Asp Ile
            20                  25                  30

Thr Thr

<210> SEQ ID NO 31
<211> LENGTH: 9
<212> TYPE: PRT
<213> ORGANISM: Homo sapiens

<400> SEQUENCE: 31

Gly Lys Asp Ala Lys Glu Lys Ser Ser
1               5
```

```
<210> SEQ ID NO 32
<211> LENGTH: 10
<212> TYPE: PRT
<213> ORGANISM: Homo sapiens

<400> SEQUENCE: 32

Gly Lys Asp Ala Lys Glu Lys Lys Ser Ser
1               5                   10

<210> SEQ ID NO 33
<211> LENGTH: 42
<212> TYPE: PRT
<213> ORGANISM: Homo sapiens

<400> SEQUENCE: 33

Gly Lys Asp Ala Lys Glu Lys Lys Ala Ala Asp Leu Gln Gln Gln Phe
1               5                   10                  15

Val His Phe Leu Asp Cys Trp Asp Val Ser Ser Ile Pro Phe Thr Leu
            20                  25                  30

His Leu Pro Gln Ala Gln Asp Ile Thr Thr
        35                  40

<210> SEQ ID NO 34
<211> LENGTH: 41
<212> TYPE: PRT
<213> ORGANISM: Homo sapiens

<400> SEQUENCE: 34

Gly Lys Asp Ala Lys Glu Lys Ala Ala Asp Leu Gln Gln Gln Phe Val
1               5                   10                  15

His Phe Leu Asp Cys Trp Asp Val Ser Ser Ile Pro Phe Thr Leu His
            20                  25                  30

Leu Pro Gln Ala Gln Asp Ile Thr Thr
        35                  40

<210> SEQ ID NO 35
<211> LENGTH: 16
<212> TYPE: PRT
<213> ORGANISM: Homo sapiens

<400> SEQUENCE: 35

Phe Ser Met Lys Gln Thr Leu Met Asn Val Lys Asn Leu Lys Thr Lys
1               5                   10                  15

<210> SEQ ID NO 36
<211> LENGTH: 17
<212> TYPE: PRT
<213> ORGANISM: Homo sapiens

<400> SEQUENCE: 36

Lys Phe Ser Met Lys Gln Thr Leu Met Asn Val Lys Asn Leu Lys Thr
1               5                   10                  15

Lys

<210> SEQ ID NO 37
<211> LENGTH: 25
<212> TYPE: PRT
<213> ORGANISM: Homo sapiens
```

-continued

```
<400> SEQUENCE: 37

Val Arg Thr Ser Lys Thr Arg Lys Lys Phe Ser Met Lys Gln Thr Leu
1               5                   10                  15
Met Asn Val Lys Asn Leu Lys Thr Lys
            20                  25

<210> SEQ ID NO 38
<211> LENGTH: 26
<212> TYPE: PRT
<213> ORGANISM: Homo sapiens

<400> SEQUENCE: 38

Val Arg Thr Ser Lys Thr Arg Lys Lys Phe Ser Met Lys Gln Thr
1               5                   10                  15
Leu Met Asn Val Lys Asn Leu Lys Thr Lys
            20                  25

<210> SEQ ID NO 39
<211> LENGTH: 12
<212> TYPE: PRT
<213> ORGANISM: Homo sapiens

<400> SEQUENCE: 39

Val Arg Thr Ser Lys Thr Arg Lys Lys Asn Phe Pro
1               5                   10

<210> SEQ ID NO 40
<211> LENGTH: 11
<212> TYPE: PRT
<213> ORGANISM: Homo sapiens

<400> SEQUENCE: 40

Val Arg Thr Ser Lys Thr Arg Lys Asn Phe Pro
1               5                   10

<210> SEQ ID NO 41
<211> LENGTH: 10
<212> TYPE: PRT
<213> ORGANISM: Homo sapiens

<400> SEQUENCE: 41

Ile Lys Lys Lys Leu Leu Gln Phe Gln Lys
1               5                   10

<210> SEQ ID NO 42
<211> LENGTH: 11
<212> TYPE: PRT
<213> ORGANISM: Homo sapiens

<400> SEQUENCE: 42

Lys Ile Lys Lys Lys Leu Leu Gln Phe Gln Lys
1               5                   10

<210> SEQ ID NO 43
<211> LENGTH: 17
<212> TYPE: PRT
<213> ORGANISM: Homo sapiens

<400> SEQUENCE: 43

Lys Ser Arg Arg Asn Tyr Phe Asn Phe Lys Asn Asn Cys Gln Ser Arg
1               5                   10                  15
Leu
```

<210> SEQ ID NO 44
<211> LENGTH: 16
<212> TYPE: PRT
<213> ORGANISM: Homo sapiens

<400> SEQUENCE: 44

Ser Arg Arg Asn Tyr Phe Asn Phe Lys Asn Asn Cys Gln Ser Arg Leu
1               5                   10                  15

<210> SEQ ID NO 45
<211> LENGTH: 18
<212> TYPE: PRT
<213> ORGANISM: Homo sapiens

<400> SEQUENCE: 45

Thr Asn Leu Arg Val Ile Gln Lys Ile Lys Lys Leu Leu Gln Phe
1               5                   10                  15

Gln Lys

<210> SEQ ID NO 46
<211> LENGTH: 19
<212> TYPE: PRT
<213> ORGANISM: Homo sapiens

<400> SEQUENCE: 46

Thr Asn Leu Arg Val Ile Gln Lys Lys Ile Lys Lys Lys Leu Leu Gln
1               5                   10                  15

Phe Gln Lys

<210> SEQ ID NO 47
<211> LENGTH: 25
<212> TYPE: PRT
<213> ORGANISM: Homo sapiens

<400> SEQUENCE: 47

Thr Asn Leu Arg Val Ile Gln Lys Lys Ser Arg Arg Asn Tyr Phe Asn
1               5                   10                  15

Phe Lys Asn Asn Cys Gln Ser Arg Leu
            20                  25

<210> SEQ ID NO 48
<211> LENGTH: 24
<212> TYPE: PRT
<213> ORGANISM: Homo sapiens

<400> SEQUENCE: 48

Thr Asn Leu Arg Val Ile Gln Lys Ser Arg Arg Asn Tyr Phe Asn Phe
1               5                   10                  15

Lys Asn Asn Cys Gln Ser Arg Leu
            20

<210> SEQ ID NO 49
<211> LENGTH: 5
<212> TYPE: PRT
<213> ORGANISM: Homo sapiens

<400> SEQUENCE: 49

Lys Ile Met Ile Thr
1               5

```
<210> SEQ ID NO 50
<211> LENGTH: 12
<212> TYPE: PRT
<213> ORGANISM: Homo sapiens

<400> SEQUENCE: 50

Asn Ile Asp Lys Ile Pro Glu Lys Ile Met Ile Thr
1               5                   10

<210> SEQ ID NO 51
<211> LENGTH: 13
<212> TYPE: PRT
<213> ORGANISM: Homo sapiens

<400> SEQUENCE: 51

Asn Ile Asp Lys Ile Pro Glu Lys Lys Ile Met Ile Thr
1               5                   10

<210> SEQ ID NO 52
<211> LENGTH: 5
<212> TYPE: PRT
<213> ORGANISM: Homo sapiens

<400> SEQUENCE: 52

Ile Ile Asn Ala Asn
1               5

<210> SEQ ID NO 53
<211> LENGTH: 6
<212> TYPE: PRT
<213> ORGANISM: Homo sapiens

<400> SEQUENCE: 53

Lys Ile Ile Asn Ala Asn
1               5

<210> SEQ ID NO 54
<211> LENGTH: 13
<212> TYPE: PRT
<213> ORGANISM: Homo sapiens

<400> SEQUENCE: 54

Asn Asp Lys Thr Val Ser Glu Lys Ile Ile Asn Ala Asn
1               5                   10

<210> SEQ ID NO 55
<211> LENGTH: 14
<212> TYPE: PRT
<213> ORGANISM: Homo sapiens

<400> SEQUENCE: 55

Asn Asp Lys Thr Val Ser Glu Lys Lys Ile Ile Asn Ala Asn
1               5                   10

<210> SEQ ID NO 56
<211> LENGTH: 14
<212> TYPE: PRT
<213> ORGANISM: Homo sapiens

<400> SEQUENCE: 56

Asn Gly Leu Glu Lys Glu Tyr Leu Met Val Asn Gln Lys Glu
1               5                   10
```

```
<210> SEQ ID NO 57
<211> LENGTH: 23
<212> TYPE: PRT
<213> ORGANISM: Homo sapiens

<400> SEQUENCE: 57

Ser Gln Thr Ser Leu Leu Glu Ala Lys Asn Gly Leu Glu Lys Glu Tyr
1               5                   10                  15

Leu Met Val Asn Gln Lys Glu
            20

<210> SEQ ID NO 58
<211> LENGTH: 24
<212> TYPE: PRT
<213> ORGANISM: Homo sapiens

<400> SEQUENCE: 58

Ser Gln Thr Ser Leu Leu Glu Ala Lys Lys Asn Gly Leu Glu Lys Glu
1               5                   10                  15

Tyr Leu Met Val Asn Gln Lys Glu
            20

<210> SEQ ID NO 59
<211> LENGTH: 12
<212> TYPE: PRT
<213> ORGANISM: Homo sapiens

<400> SEQUENCE: 59

Ser Gln Thr Ser Leu Leu Glu Ala Lys Lys Met Ala
1               5                   10

<210> SEQ ID NO 60
<211> LENGTH: 11
<212> TYPE: PRT
<213> ORGANISM: Homo sapiens

<400> SEQUENCE: 60

Ser Gln Thr Ser Leu Leu Glu Ala Lys Met Ala
1               5                   10

<210> SEQ ID NO 61
<211> LENGTH: 6
<212> TYPE: PRT
<213> ORGANISM: Homo sapiens

<400> SEQUENCE: 61

Thr Leu Val Phe Pro Lys
1               5

<210> SEQ ID NO 62
<211> LENGTH: 7
<212> TYPE: PRT
<213> ORGANISM: Homo sapiens

<400> SEQUENCE: 62

Lys Thr Leu Val Phe Pro Lys
1               5

<210> SEQ ID NO 63
<211> LENGTH: 14
<212> TYPE: PRT
<213> ORGANISM: Homo sapiens
```

```
<400> SEQUENCE: 63

Leu Lys Asn Val Glu Asp Gln Lys Thr Leu Val Phe Pro Lys
1               5                   10

<210> SEQ ID NO 64
<211> LENGTH: 15
<212> TYPE: PRT
<213> ORGANISM: Homo sapiens

<400> SEQUENCE: 64

Leu Lys Asn Val Glu Asp Gln Lys Lys Thr Leu Val Phe Pro Lys
1               5                   10                  15

<210> SEQ ID NO 65
<211> LENGTH: 10
<212> TYPE: PRT
<213> ORGANISM: Homo sapiens

<400> SEQUENCE: 65

Leu Lys Asn Val Glu Asp Gln Lys Lys His
1               5                   10

<210> SEQ ID NO 66
<211> LENGTH: 9
<212> TYPE: PRT
<213> ORGANISM: Homo sapiens

<400> SEQUENCE: 66

Leu Lys Asn Val Glu Asp Gln Lys His
1               5

<210> SEQ ID NO 67
<211> LENGTH: 6
<212> TYPE: PRT
<213> ORGANISM: Homo sapiens

<400> SEQUENCE: 67

Lys Lys Ile Gln Leu Tyr
1               5

<210> SEQ ID NO 68
<211> LENGTH: 7
<212> TYPE: PRT
<213> ORGANISM: Homo sapiens

<400> SEQUENCE: 68

Lys Lys Lys Ile Gln Leu Tyr
1               5

<210> SEQ ID NO 69
<211> LENGTH: 36
<212> TYPE: PRT
<213> ORGANISM: Homo sapiens

<400> SEQUENCE: 69

Arg Lys Arg Phe Ser Tyr Thr Glu Tyr Leu Ala Ser Ile Ile Arg Phe
1               5                   10                  15

Ile Phe Ser Val Asn Arg Arg Lys Glu Ile Gln Asn Leu Ser Ser Cys
            20                  25                  30

Asn Phe Lys Ile
        35
```

```
<210> SEQ ID NO 70
<211> LENGTH: 15
<212> TYPE: PRT
<213> ORGANISM: Homo sapiens

<400> SEQUENCE: 70

Leu Arg Ile Val Ser Tyr Ser Lys Lys Lys Ile Gln Leu Tyr
1               5                   10                  15

<210> SEQ ID NO 71
<211> LENGTH: 16
<212> TYPE: PRT
<213> ORGANISM: Homo sapiens

<400> SEQUENCE: 71

Leu Arg Ile Val Ser Tyr Ser Lys Lys Lys Lys Ile Gln Leu Tyr
1               5                   10                  15

<210> SEQ ID NO 72
<211> LENGTH: 45
<212> TYPE: PRT
<213> ORGANISM: Homo sapiens

<400> SEQUENCE: 72

Leu Arg Ile Val Ser Tyr Ser Lys Lys Arg Lys Arg Phe Ser Tyr Thr
1               5                   10                  15

Glu Tyr Leu Ala Ser Ile Ile Arg Phe Ile Phe Ser Val Asn Arg Arg
            20                  25                  30

Lys Glu Ile Gln Asn Leu Ser Ser Cys Asn Phe Lys Ile
        35                  40                  45

<210> SEQ ID NO 73
<211> LENGTH: 44
<212> TYPE: PRT
<213> ORGANISM: Homo sapiens

<400> SEQUENCE: 73

Leu Arg Ile Val Ser Tyr Ser Lys Arg Lys Arg Phe Ser Tyr Thr Glu
1               5                   10                  15

Tyr Leu Ala Ser Ile Ile Arg Phe Ile Phe Ser Val Asn Arg Arg Lys
            20                  25                  30

Glu Ile Gln Asn Leu Ser Ser Cys Asn Phe Lys Ile
        35                  40

<210> SEQ ID NO 74
<211> LENGTH: 18
<212> TYPE: PRT
<213> ORGANISM: Homo sapiens

<400> SEQUENCE: 74

Gln Asp Leu Pro Leu Ser Ser Ile Cys Gln Thr Ile Val Thr Ile Tyr
1               5                   10                  15

Trp Gln

<210> SEQ ID NO 75
<211> LENGTH: 19
<212> TYPE: PRT
<213> ORGANISM: Homo sapiens
```

```
<400> SEQUENCE: 75

Lys Gln Asp Leu Pro Leu Ser Ser Ile Cys Gln Thr Ile Val Thr Ile
1               5                   10                  15

Tyr Trp Gln

<210> SEQ ID NO 76
<211> LENGTH: 25
<212> TYPE: PRT
<213> ORGANISM: Homo sapiens

<400> SEQUENCE: 76

Asn Arg Thr Cys Pro Phe Arg Leu Phe Val Arg Met Leu Gln Phe
1               5                   10                  15

Thr Gly Asn Lys Val Leu Asp Arg Pro
            20                  25

<210> SEQ ID NO 77
<211> LENGTH: 27
<212> TYPE: PRT
<213> ORGANISM: Homo sapiens

<400> SEQUENCE: 77

Gly Phe Val Val Ser Val Val Lys Lys Gln Asp Leu Pro Leu Ser Ser
1               5                   10                  15

Ile Cys Gln Thr Ile Val Thr Ile Tyr Trp Gln
            20                  25

<210> SEQ ID NO 78
<211> LENGTH: 28
<212> TYPE: PRT
<213> ORGANISM: Homo sapiens

<400> SEQUENCE: 78

Gly Phe Val Val Ser Val Val Lys Lys Gln Asp Leu Pro Leu Ser
1               5                   10                  15

Ser Ile Cys Gln Thr Ile Val Thr Ile Tyr Trp Gln
            20                  25

<210> SEQ ID NO 79
<211> LENGTH: 34
<212> TYPE: PRT
<213> ORGANISM: Homo sapiens

<400> SEQUENCE: 79

Gly Phe Val Val Ser Val Val Lys Lys Asn Arg Thr Cys Pro Phe Arg
1               5                   10                  15

Leu Phe Val Arg Arg Met Leu Gln Phe Thr Gly Asn Lys Val Leu Asp
            20                  25                  30

Arg Pro

<210> SEQ ID NO 80
<211> LENGTH: 33
<212> TYPE: PRT
<213> ORGANISM: Homo sapiens

<400> SEQUENCE: 80

Gly Phe Val Val Ser Val Val Lys Asn Arg Thr Cys Pro Phe Arg Leu
1               5                   10                  15
```

-continued

Phe Val Arg Arg Met Leu Gln Phe Thr Gly Asn Lys Val Leu Asp Arg
                20                  25                  30
Pro

<210> SEQ ID NO 81
<211> LENGTH: 8
<212> TYPE: PRT
<213> ORGANISM: Homo sapiens

<400> SEQUENCE: 81

Tyr Arg Lys Thr Lys Asn Gln Asn
1               5

<210> SEQ ID NO 82
<211> LENGTH: 9
<212> TYPE: PRT
<213> ORGANISM: Homo sapiens

<400> SEQUENCE: 82

Lys Tyr Arg Lys Thr Lys Asn Gln Asn
1               5

<210> SEQ ID NO 83
<211> LENGTH: 10
<212> TYPE: PRT
<213> ORGANISM: Homo sapiens

<400> SEQUENCE: 83

Asn Thr Glu Arg Pro Lys Ile Arg Thr Asn
1               5                   10

<210> SEQ ID NO 84
<211> LENGTH: 17
<212> TYPE: PRT
<213> ORGANISM: Homo sapiens

<400> SEQUENCE: 84

Asp Glu Thr Phe Tyr Lys Gly Lys Lys Tyr Arg Lys Thr Lys Asn Gln
1               5                   10                  15

Asn

<210> SEQ ID NO 85
<211> LENGTH: 18
<212> TYPE: PRT
<213> ORGANISM: Homo sapiens

<400> SEQUENCE: 85

Asp Glu Thr Phe Tyr Lys Gly Lys Lys Lys Tyr Arg Lys Thr Lys Asn
1               5                   10                  15

Gln Asn

<210> SEQ ID NO 86
<211> LENGTH: 19
<212> TYPE: PRT
<213> ORGANISM: Homo sapiens

<400> SEQUENCE: 86

Asp Glu Thr Phe Tyr Lys Gly Lys Lys Asn Thr Glu Arg Pro Lys Ile
1               5                   10                  15

Arg Thr Asn

<210> SEQ ID NO 87
<211> LENGTH: 18
<212> TYPE: PRT
<213> ORGANISM: Homo sapiens

<400> SEQUENCE: 87

Asp Glu Thr Phe Tyr Lys Gly Lys Asn Thr Glu Arg Pro Lys Ile Arg
1               5                   10                  15
Thr Asn

<210> SEQ ID NO 88
<211> LENGTH: 28
<212> TYPE: PRT
<213> ORGANISM: Homo sapiens

<400> SEQUENCE: 88

Leu Ser Ile Asn Asn Tyr Arg Phe Gln Met Lys Phe Tyr Phe Arg Phe
1               5                   10                  15
Thr Ser His Gly Ser Pro Phe Thr Ser Ala Asn Phe
            20                  25

<210> SEQ ID NO 89
<211> LENGTH: 29
<212> TYPE: PRT
<213> ORGANISM: Homo sapiens

<400> SEQUENCE: 89

Lys Leu Ser Ile Asn Asn Tyr Arg Phe Gln Met Lys Phe Tyr Phe Arg
1               5                   10                  15
Phe Thr Ser His Gly Ser Pro Phe Thr Ser Ala Asn Phe
            20                  25

<210> SEQ ID NO 90
<211> LENGTH: 10
<212> TYPE: PRT
<213> ORGANISM: Homo sapiens

<400> SEQUENCE: 90

Asn Ser Val Ser Thr Thr Thr Gly Phe Arg
1               5                   10

<210> SEQ ID NO 91
<211> LENGTH: 37
<212> TYPE: PRT
<213> ORGANISM: Homo sapiens

<400> SEQUENCE: 91

Asn Ile Gln Leu Ala Ala Thr Lys Lys Leu Ser Ile Asn Asn Tyr Arg
1               5                   10                  15
Phe Gln Met Lys Phe Tyr Phe Arg Phe Thr Ser His Gly Ser Pro Phe
            20                  25                  30
Thr Ser Ala Asn Phe
        35

<210> SEQ ID NO 92
<211> LENGTH: 38
<212> TYPE: PRT
<213> ORGANISM: Homo sapiens

<400> SEQUENCE: 92

Asn Ile Gln Leu Ala Ala Thr Lys Lys Leu Ser Ile Asn Asn Tyr
1               5                   10                  15

```
Arg Phe Gln Met Lys Phe Tyr Phe Arg Phe Thr Ser His Gly Ser Pro
            20                  25                  30

Phe Thr Ser Ala Asn Phe
            35

<210> SEQ ID NO 93
<211> LENGTH: 19
<212> TYPE: PRT
<213> ORGANISM: Homo sapiens

<400> SEQUENCE: 93

Asn Ile Gln Leu Ala Ala Thr Lys Lys Asn Ser Val Ser Thr Thr Thr
1               5                   10                  15

Gly Phe Arg

<210> SEQ ID NO 94
<211> LENGTH: 18
<212> TYPE: PRT
<213> ORGANISM: Homo sapiens

<400> SEQUENCE: 94

Asn Ile Gln Leu Ala Ala Thr Lys Asn Ser Val Ser Thr Thr Thr Gly
1               5                   10                  15

Phe Arg

<210> SEQ ID NO 95
<211> LENGTH: 18
<212> TYPE: PRT
<213> ORGANISM: Homo sapiens

<400> SEQUENCE: 95

Met Glu His Val Ala Pro Gly Arg Met Ser Ala Ser Pro Gln Ser Pro
1               5                   10                  15

Thr Gln

<210> SEQ ID NO 96
<211> LENGTH: 19
<212> TYPE: PRT
<213> ORGANISM: Homo sapiens

<400> SEQUENCE: 96

Lys Met Glu His Val Ala Pro Gly Arg Met Ser Ala Ser Pro Gln Ser
1               5                   10                  15

Pro Thr Gln

<210> SEQ ID NO 97
<211> LENGTH: 59
<212> TYPE: PRT
<213> ORGANISM: Homo sapiens

<400> SEQUENCE: 97

Lys Trp Ser Thr Trp Leu Gln Ala Glu Cys Gln His Leu His Ser Pro
1               5                   10                  15

Gln Arg Ser Asp Lys Pro Gln Gln Ala Gly Leu Asp Gln His His
            20                  25                  30

Cys Phe Ala Leu Asp Ser Ser Pro Gly Pro Arg Pro Val Phe Leu Gln
            35                  40                  45

Leu Leu Gly Leu Met Gly Gln Gly Arg His Asp
        50                  55
```

```
<210> SEQ ID NO 98
<211> LENGTH: 58
<212> TYPE: PRT
<213> ORGANISM: Homo sapiens

<400> SEQUENCE: 98

Trp Ser Thr Trp Leu Gln Ala Glu Cys Gln His Leu His Ser Pro Gln
1               5                   10                  15

Arg Ser Asp Lys Pro Gln Gln Ala Gly Leu Asp Gln Gln His His Cys
            20                  25                  30

Phe Ala Leu Asp Ser Ser Pro Gly Pro Arg Pro Val Phe Leu Gln Leu
        35                  40                  45

Leu Gly Leu Met Gly Gln Gly Arg His Asp
    50                  55

<210> SEQ ID NO 99
<211> LENGTH: 26
<212> TYPE: PRT
<213> ORGANISM: Homo sapiens

<400> SEQUENCE: 99

Thr Phe Ser Val Trp Ala Glu Lys Met Glu His Val Ala Pro Gly Arg
1               5                   10                  15

Met Ser Ala Ser Pro Gln Ser Pro Thr Gln
            20                  25

<210> SEQ ID NO 100
<211> LENGTH: 27
<212> TYPE: PRT
<213> ORGANISM: Homo sapiens

<400> SEQUENCE: 100

Thr Phe Ser Val Trp Ala Glu Lys Lys Met Glu His Val Ala Pro Gly
1               5                   10                  15

Arg Met Ser Ala Ser Pro Gln Ser Pro Thr Gln
            20                  25

<210> SEQ ID NO 101
<211> LENGTH: 67
<212> TYPE: PRT
<213> ORGANISM: Homo sapiens

<400> SEQUENCE: 101

Thr Phe Ser Val Trp Ala Glu Lys Lys Trp Ser Thr Trp Leu Gln Ala
1               5                   10                  15

Glu Cys Gln His Leu His Ser Pro Gln Arg Ser Asp Lys Pro Gln Gln
            20                  25                  30

Ala Gly Leu Asp Gln Gln His His Cys Phe Ala Leu Asp Ser Ser Pro
        35                  40                  45

Gly Pro Arg Pro Val Phe Leu Gln Leu Leu Gly Leu Met Gly Gln Gly
    50                  55                  60

Arg His Asp
65

<210> SEQ ID NO 102
<211> LENGTH: 66
<212> TYPE: PRT
<213> ORGANISM: Homo sapiens
```

-continued

<400> SEQUENCE: 102

Thr Phe Ser Val Trp Ala Glu Lys Trp Ser Thr Trp Leu Gln Ala Glu
1               5                   10                  15

Cys Gln His Leu His Ser Pro Gln Arg Ser Asp Lys Pro Gln Gln Ala
            20                  25                  30

Gly Leu Asp Gln Gln His His Cys Phe Ala Leu Asp Ser Ser Pro Gly
        35                  40                  45

Pro Arg Pro Val Phe Leu Gln Leu Leu Gly Leu Met Gly Gln Gly Arg
    50                  55                  60

His Asp
65

<210> SEQ ID NO 103
<211> LENGTH: 18
<212> TYPE: PRT
<213> ORGANISM: Homo sapiens

<400> SEQUENCE: 103

His Lys Trp Leu Lys Phe Cys Leu Leu Arg Leu Val Lys Glu Ser Phe
1               5                   10                  15

His Glu

<210> SEQ ID NO 104
<211> LENGTH: 19
<212> TYPE: PRT
<213> ORGANISM: Homo sapiens

<400> SEQUENCE: 104

Lys His Lys Trp Leu Lys Phe Cys Leu Leu Arg Leu Val Lys Glu Ser
1               5                   10                  15

Phe His Glu

<210> SEQ ID NO 105
<211> LENGTH: 27
<212> TYPE: PRT
<213> ORGANISM: Homo sapiens

<400> SEQUENCE: 105

Lys Gly Gly Lys Ala Lys Gly Lys Lys His Lys Trp Leu Lys Phe Cys
1               5                   10                  15

Leu Leu Arg Leu Val Lys Glu Ser Phe His Glu
            20                  25

<210> SEQ ID NO 106
<211> LENGTH: 28
<212> TYPE: PRT
<213> ORGANISM: Homo sapiens

<400> SEQUENCE: 106

Lys Gly Gly Lys Ala Lys Gly Lys Lys Lys His Lys Trp Leu Lys Phe
1               5                   10                  15

Cys Leu Leu Arg Leu Val Lys Glu Ser Phe His Glu
            20                  25

<210> SEQ ID NO 107
<211> LENGTH: 13
<212> TYPE: PRT
<213> ORGANISM: Homo sapiens

<400> SEQUENCE: 107

Lys Gly Gly Lys Ala Lys Gly Lys Lys Asn Thr Asn Gly
1               5                   10

<210> SEQ ID NO 108
<211> LENGTH: 12
<212> TYPE: PRT
<213> ORGANISM: Homo sapiens

<400> SEQUENCE: 108

Lys Gly Gly Lys Ala Lys Gly Lys Asn Thr Asn Gly
1               5                   10

<210> SEQ ID NO 109
<211> LENGTH: 8
<212> TYPE: PRT
<213> ORGANISM: Homo sapiens

<400> SEQUENCE: 109

Val Asn Asn Phe Phe Lys Lys Leu
1               5

<210> SEQ ID NO 110
<211> LENGTH: 9
<212> TYPE: PRT
<213> ORGANISM: Homo sapiens

<400> SEQUENCE: 110

Lys Val Asn Asn Phe Phe Lys Lys Leu
1               5

<210> SEQ ID NO 111
<211> LENGTH: 16
<212> TYPE: PRT
<213> ORGANISM: Homo sapiens

<400> SEQUENCE: 111

Leu Ser Gln Gly Asn Val Lys Lys Val Asn Asn Phe Phe Lys Lys Leu
1               5                   10                  15

<210> SEQ ID NO 112
<211> LENGTH: 17
<212> TYPE: PRT
<213> ORGANISM: Homo sapiens

<400> SEQUENCE: 112

Leu Ser Gln Gly Asn Val Lys Lys Val Asn Asn Phe Phe Lys Lys
1               5                   10                  15

Leu

<210> SEQ ID NO 113
<211> LENGTH: 38
<212> TYPE: PRT
<213> ORGANISM: Homo sapiens

<400> SEQUENCE: 113

Gly Glu Lys Asn Asp Leu Gln Leu Phe Val Met Ser Asp Arg Arg Tyr
1               5                   10                  15

Lys Ile Tyr Trp Thr Val Ile Leu Asn Pro Cys Gly Asn Leu His
            20                  25                  30

Leu Lys Thr Thr Ser Leu
        35

```
<210> SEQ ID NO 114
<211> LENGTH: 39
<212> TYPE: PRT
<213> ORGANISM: Homo sapiens

<400> SEQUENCE: 114

Lys Gly Glu Lys Asn Asp Leu Gln Leu Phe Val Met Ser Asp Arg Arg
1               5                   10                  15

Tyr Lys Ile Tyr Trp Thr Val Ile Leu Leu Asn Pro Cys Gly Asn Leu
            20                  25                  30

His Leu Lys Thr Thr Ser Leu
        35

<210> SEQ ID NO 115
<211> LENGTH: 10
<212> TYPE: PRT
<213> ORGANISM: Homo sapiens

<400> SEQUENCE: 115

Lys Gly Lys Lys Met Ile Cys Ser Tyr Ser
1               5                   10

<210> SEQ ID NO 116
<211> LENGTH: 9
<212> TYPE: PRT
<213> ORGANISM: Homo sapiens

<400> SEQUENCE: 116

Gly Lys Lys Met Ile Cys Ser Tyr Ser
1               5

<210> SEQ ID NO 117
<211> LENGTH: 46
<212> TYPE: PRT
<213> ORGANISM: Homo sapiens

<400> SEQUENCE: 117

Ser Ser Lys Thr Phe Glu Lys Gly Glu Lys Asn Asp Leu Gln Leu
1               5                   10                  15

Phe Val Met Ser Asp Arg Arg Tyr Lys Ile Tyr Trp Thr Val Ile Leu
            20                  25                  30

Leu Asn Pro Cys Gly Asn Leu His Leu Lys Thr Thr Ser Leu
        35                  40                  45

<210> SEQ ID NO 118
<211> LENGTH: 47
<212> TYPE: PRT
<213> ORGANISM: Homo sapiens

<400> SEQUENCE: 118

Ser Ser Lys Thr Phe Glu Lys Lys Gly Glu Lys Asn Asp Leu Gln
1               5                   10                  15

Leu Phe Val Met Ser Asp Arg Arg Tyr Lys Ile Tyr Trp Thr Val Ile
            20                  25                  30

Leu Leu Asn Pro Cys Gly Asn Leu His Leu Lys Thr Thr Ser Leu
        35                  40                  45

<210> SEQ ID NO 119
<211> LENGTH: 18
<212> TYPE: PRT
<213> ORGANISM: Homo sapiens
```

```
<400> SEQUENCE: 119

Ser Ser Lys Thr Phe Glu Lys Lys Gly Lys Lys Met Ile Cys Ser
1               5                   10                  15

Tyr Ser

<210> SEQ ID NO 120
<211> LENGTH: 17
<212> TYPE: PRT
<213> ORGANISM: Homo sapiens

<400> SEQUENCE: 120

Ser Ser Lys Thr Phe Glu Lys Lys Gly Lys Lys Met Ile Cys Ser Tyr
1               5                   10                  15

Ser

<210> SEQ ID NO 121
<211> LENGTH: 17
<212> TYPE: PRT
<213> ORGANISM: Homo sapiens

<400> SEQUENCE: 121

Gln Arg Lys Pro Lys Arg Ala Asn Cys Val Ile Gln Arg Arg Ala Lys
1               5                   10                  15

Met

<210> SEQ ID NO 122
<211> LENGTH: 18
<212> TYPE: PRT
<213> ORGANISM: Homo sapiens

<400> SEQUENCE: 122

Lys Gln Arg Lys Pro Lys Arg Ala Asn Cys Val Ile Gln Arg Arg Ala
1               5                   10                  15

Lys Met

<210> SEQ ID NO 123
<211> LENGTH: 26
<212> TYPE: PRT
<213> ORGANISM: Homo sapiens

<400> SEQUENCE: 123

Asn Lys Glu Asn Gln Lys Glu Gln Thr Ala Leu Leu Tyr Arg Gly Gly
1               5                   10                  15

Gln Arg Cys Arg Cys Val Cys Leu Arg Phe
                20                  25

<210> SEQ ID NO 124
<211> LENGTH: 26
<212> TYPE: PRT
<213> ORGANISM: Homo sapiens

<400> SEQUENCE: 124

Pro Asp Tyr Gln Pro Pro Ala Lys Lys Gln Arg Lys Pro Lys Arg Ala
1               5                   10                  15

Asn Cys Val Ile Gln Arg Arg Ala Lys Met
                20                  25

<210> SEQ ID NO 125
<211> LENGTH: 27
<212> TYPE: PRT
<213> ORGANISM: Homo sapiens
```

```
<400> SEQUENCE: 125

Pro Asp Tyr Gln Pro Pro Ala Lys Lys Lys Gln Arg Lys Pro Lys Arg
1               5                   10                  15

Ala Asn Cys Val Ile Gln Arg Arg Ala Lys Met
            20                  25

<210> SEQ ID NO 126
<211> LENGTH: 35
<212> TYPE: PRT
<213> ORGANISM: Homo sapiens

<400> SEQUENCE: 126

Pro Asp Tyr Gln Pro Pro Ala Lys Lys Asn Lys Glu Asn Gln Lys Glu
1               5                   10                  15

Gln Thr Ala Leu Leu Tyr Arg Gly Gly Gln Arg Cys Arg Cys Val Cys
            20                  25                  30

Leu Arg Phe
        35

<210> SEQ ID NO 127
<211> LENGTH: 34
<212> TYPE: PRT
<213> ORGANISM: Homo sapiens

<400> SEQUENCE: 127

Pro Asp Tyr Gln Pro Pro Ala Lys Asn Lys Glu Asn Gln Lys Glu Gln
1               5                   10                  15

Thr Ala Leu Leu Tyr Arg Gly Gly Gln Arg Cys Arg Cys Val Cys Leu
            20                  25                  30

Arg Phe

<210> SEQ ID NO 128
<211> LENGTH: 7
<212> TYPE: PRT
<213> ORGANISM: Homo sapiens

<400> SEQUENCE: 128

Asn Leu Ser Ser Leu Leu Ile
1               5

<210> SEQ ID NO 129
<211> LENGTH: 5
<212> TYPE: PRT
<213> ORGANISM: Homo sapiens

<400> SEQUENCE: 129

Thr Cys Leu Pro Phe
1               5

<210> SEQ ID NO 130
<211> LENGTH: 15
<212> TYPE: PRT
<213> ORGANISM: Homo sapiens

<400> SEQUENCE: 130

Gln Pro Thr Phe Thr Leu Arg Lys Asn Leu Ser Ser Leu Leu Ile
1               5                   10                  15

<210> SEQ ID NO 131
<211> LENGTH: 16
<212> TYPE: PRT
<213> ORGANISM: Homo sapiens
```

<400> SEQUENCE: 131

Gln Pro Thr Phe Thr Leu Arg Lys Lys Asn Leu Ser Ser Leu Leu Ile
1               5                   10                  15

<210> SEQ ID NO 132
<211> LENGTH: 14
<212> TYPE: PRT
<213> ORGANISM: Homo sapiens

<400> SEQUENCE: 132

Gln Pro Thr Phe Thr Leu Arg Lys Lys Thr Cys Leu Pro Phe
1               5                   10

<210> SEQ ID NO 133
<211> LENGTH: 13
<212> TYPE: PRT
<213> ORGANISM: Homo sapiens

<400> SEQUENCE: 133

Gln Pro Thr Phe Thr Leu Arg Lys Thr Cys Leu Pro Phe
1               5                   10

<210> SEQ ID NO 134
<211> LENGTH: 31
<212> TYPE: PRT
<213> ORGANISM: Homo sapiens

<400> SEQUENCE: 134

Arg Ala Thr Phe Leu Leu Ser Leu Trp Glu Cys Ser Leu Pro Gln Ala
1               5                   10                  15

Arg Leu Cys Leu Ile Val Ser Arg Thr Gly Leu Leu Val Gln Ser
            20                  25                  30

<210> SEQ ID NO 135
<211> LENGTH: 19
<212> TYPE: PRT
<213> ORGANISM: Homo sapiens

<400> SEQUENCE: 135

Gly Gln His Phe Tyr Trp His Cys Gly Ser Ala Ala Cys His Arg Arg
1               5                   10                  15

Gly Cys Val

<210> SEQ ID NO 136
<211> LENGTH: 39
<212> TYPE: PRT
<213> ORGANISM: Homo sapiens

<400> SEQUENCE: 136

Lys Glu Asn Val Arg Asp Lys Lys Arg Ala Thr Phe Leu Leu Ser Leu
1               5                   10                  15

Trp Glu Cys Ser Leu Pro Gln Ala Arg Leu Cys Leu Ile Val Ser Arg
            20                  25                  30

Thr Gly Leu Leu Val Gln Ser
        35

<210> SEQ ID NO 137
<211> LENGTH: 40
<212> TYPE: PRT
<213> ORGANISM: Homo sapiens

```
<400> SEQUENCE: 137

Lys Glu Asn Val Arg Asp Lys Lys Arg Ala Thr Phe Leu Leu Ser
1               5                   10                  15

Leu Trp Glu Cys Ser Leu Pro Gln Ala Arg Leu Cys Leu Ile Val Ser
            20                  25                  30

Arg Thr Gly Leu Leu Val Gln Ser
        35                  40

<210> SEQ ID NO 138
<211> LENGTH: 28
<212> TYPE: PRT
<213> ORGANISM: Homo sapiens

<400> SEQUENCE: 138

Lys Glu Asn Val Arg Asp Lys Lys Gly Gln His Phe Tyr Trp His
1               5                   10                  15

Cys Gly Ser Ala Ala Cys His Arg Arg Gly Cys Val
            20                  25

<210> SEQ ID NO 139
<211> LENGTH: 27
<212> TYPE: PRT
<213> ORGANISM: Homo sapiens

<400> SEQUENCE: 139

Lys Glu Asn Val Arg Asp Lys Lys Gly Gln His Phe Tyr Trp His Cys
1               5                   10                  15

Gly Ser Ala Ala Cys His Arg Arg Gly Cys Val
            20                  25

<210> SEQ ID NO 140
<211> LENGTH: 39
<212> TYPE: PRT
<213> ORGANISM: Homo sapiens

<400> SEQUENCE: 140

Ile Thr His Thr Arg Trp Gly Ile Thr Thr Trp Asp Ser Trp Ser Val
1               5                   10                  15

Arg Met Lys Ala Asn Trp Ile Gln Ala Gln Gln Asn Lys Ser Leu Ile
            20                  25                  30

Leu Ser Pro Ser Phe Thr Lys
        35

<210> SEQ ID NO 141
<211> LENGTH: 40
<212> TYPE: PRT
<213> ORGANISM: Homo sapiens

<400> SEQUENCE: 141

Lys Ile Thr His Thr Arg Trp Gly Ile Thr Thr Trp Asp Ser Trp Ser
1               5                   10                  15

Val Arg Met Lys Ala Asn Trp Ile Gln Ala Gln Gln Asn Lys Ser Leu
            20                  25                  30

Ile Leu Ser Pro Ser Phe Thr Lys
        35                  40

<210> SEQ ID NO 142
<211> LENGTH: 16
<212> TYPE: PRT
<213> ORGANISM: Homo sapiens
```

```
<400> SEQUENCE: 142

Lys Leu Leu Thr Pro Gly Gly Glu Leu Pro His Gly Ile Leu Gly Gln
1               5                   10                  15

<210> SEQ ID NO 143
<211> LENGTH: 15
<212> TYPE: PRT
<213> ORGANISM: Homo sapiens

<400> SEQUENCE: 143

Leu Leu Thr Pro Gly Gly Glu Leu Pro His Gly Ile Leu Gly Gln
1               5                   10                  15

<210> SEQ ID NO 144
<211> LENGTH: 47
<212> TYPE: PRT
<213> ORGANISM: Homo sapiens

<400> SEQUENCE: 144

Pro Pro Val Cys Glu Leu Glu Lys Ile Thr His Thr Arg Trp Gly Ile
1               5                   10                  15

Thr Thr Trp Asp Ser Trp Ser Val Arg Met Lys Ala Asn Trp Ile Gln
            20                  25                  30

Ala Gln Gln Asn Lys Ser Leu Ile Leu Ser Pro Ser Phe Thr Lys
        35                  40                  45

<210> SEQ ID NO 145
<211> LENGTH: 48
<212> TYPE: PRT
<213> ORGANISM: Homo sapiens

<400> SEQUENCE: 145

Pro Pro Val Cys Glu Leu Glu Lys Lys Ile Thr His Thr Arg Trp Gly
1               5                   10                  15

Ile Thr Thr Trp Asp Ser Trp Ser Val Arg Met Lys Ala Asn Trp Ile
            20                  25                  30

Gln Ala Gln Gln Asn Lys Ser Leu Ile Leu Ser Pro Ser Phe Thr Lys
        35                  40                  45

<210> SEQ ID NO 146
<211> LENGTH: 24
<212> TYPE: PRT
<213> ORGANISM: Homo sapiens

<400> SEQUENCE: 146

Pro Pro Val Cys Glu Leu Glu Lys Lys Leu Leu Thr Pro Gly Gly Glu
1               5                   10                  15

Leu Pro His Gly Ile Leu Gly Gln
            20

<210> SEQ ID NO 147
<211> LENGTH: 23
<212> TYPE: PRT
<213> ORGANISM: Homo sapiens

<400> SEQUENCE: 147

Pro Pro Val Cys Glu Leu Glu Lys Leu Leu Thr Pro Gly Gly Glu Leu
1               5                   10                  15

Pro His Gly Ile Leu Gly Gln
            20
```

```
<210> SEQ ID NO 148
<211> LENGTH: 11
<212> TYPE: PRT
<213> ORGANISM: Homo sapiens

<400> SEQUENCE: 148

Ser Leu Lys Asp Glu Leu Glu Lys Met Lys Ile
1               5                   10

<210> SEQ ID NO 149
<211> LENGTH: 12
<212> TYPE: PRT
<213> ORGANISM: Homo sapiens

<400> SEQUENCE: 149

Ser Leu Lys Asp Glu Leu Glu Lys Lys Met Lys Ile
1               5                   10

<210> SEQ ID NO 150
<211> LENGTH: 12
<212> TYPE: PRT
<213> ORGANISM: Homo sapiens

<400> SEQUENCE: 150

Leu Gly Gln Ser Ser Pro Glu Lys Lys Asn Lys Asn
1               5                   10

<210> SEQ ID NO 151
<211> LENGTH: 11
<212> TYPE: PRT
<213> ORGANISM: Homo sapiens

<400> SEQUENCE: 151

Leu Gly Gln Ser Ser Pro Glu Lys Asn Lys Asn
1               5                   10

<210> SEQ ID NO 152
<211> LENGTH: 23
<212> TYPE: PRT
<213> ORGANISM: Homo sapiens

<400> SEQUENCE: 152

Arg Leu Arg Arg Ile Asn Gly Arg Gly Ser Gln Ile Arg Ser Arg Asn
1               5                   10                  15

Ala Phe Asn Arg Ser Glu Glu
            20

<210> SEQ ID NO 153
<211> LENGTH: 10
<212> TYPE: PRT
<213> ORGANISM: Homo sapiens

<400> SEQUENCE: 153

Glu Pro Lys Val Lys Glu Glu Lys Lys Thr
1               5                   10

<210> SEQ ID NO 154
<211> LENGTH: 11
<212> TYPE: PRT
<213> ORGANISM: Homo sapiens

<400> SEQUENCE: 154

Glu Pro Lys Val Lys Glu Glu Lys Lys Lys Thr
1               5                   10
```

<210> SEQ ID NO 155
<211> LENGTH: 32
<212> TYPE: PRT
<213> ORGANISM: Homo sapiens

<400> SEQUENCE: 155

Glu Pro Lys Val Lys Glu Glu Lys Arg Leu Arg Arg Ile Asn Gly
1               5                   10                  15

Arg Gly Ser Gln Ile Arg Ser Arg Asn Ala Phe Asn Arg Ser Glu Glu
            20                  25                  30

<210> SEQ ID NO 156
<211> LENGTH: 31
<212> TYPE: PRT
<213> ORGANISM: Homo sapiens

<400> SEQUENCE: 156

Glu Pro Lys Val Lys Glu Glu Lys Arg Leu Arg Arg Ile Asn Gly Arg
1               5                   10                  15

Gly Ser Gln Ile Arg Ser Arg Asn Ala Phe Asn Arg Ser Glu Glu
            20                  25                  30

<210> SEQ ID NO 157
<211> LENGTH: 14
<212> TYPE: PRT
<213> ORGANISM: Homo sapiens

<400> SEQUENCE: 157

Thr Phe Arg Tyr Lys Gly Lys Gln His Pro Phe Phe Ser Thr
1               5                   10

<210> SEQ ID NO 158
<211> LENGTH: 10
<212> TYPE: PRT
<213> ORGANISM: Homo sapiens

<400> SEQUENCE: 158

Gly Pro Asn Ala Pro Glu Glu Lys Asn His
1               5                   10

<210> SEQ ID NO 159
<211> LENGTH: 11
<212> TYPE: PRT
<213> ORGANISM: Homo sapiens

<400> SEQUENCE: 159

Gly Pro Asn Ala Pro Glu Glu Lys Lys Asn His
1               5                   10

<210> SEQ ID NO 160
<211> LENGTH: 23
<212> TYPE: PRT
<213> ORGANISM: Homo sapiens

<400> SEQUENCE: 160

Gly Pro Asn Ala Pro Glu Glu Lys Thr Phe Arg Tyr Lys Gly Lys
1               5                   10                  15

Gln His Pro Phe Phe Ser Thr
            20

<210> SEQ ID NO 161
<211> LENGTH: 22
<212> TYPE: PRT
<213> ORGANISM: Homo sapiens -continued

<400> SEQUENCE: 161

Gly Pro Asn Ala Pro Glu Glu Lys Thr Phe Arg Tyr Lys Gly Lys Gln
1               5                   10                  15

His Pro Phe Phe Ser Thr
            20

<210> SEQ ID NO 162
<211> LENGTH: 6
<212> TYPE: PRT
<213> ORGANISM: Homo sapiens

<400> SEQUENCE: 162

Met Gln Asn Thr Cys Val
1               5

<210> SEQ ID NO 163
<211> LENGTH: 7
<212> TYPE: PRT
<213> ORGANISM: Homo sapiens

<400> SEQUENCE: 163

Lys Met Gln Asn Thr Cys Val
1               5

<210> SEQ ID NO 164
<211> LENGTH: 9
<212> TYPE: PRT
<213> ORGANISM: Homo sapiens

<400> SEQUENCE: 164

Lys Cys Lys Ile Arg Val Phe Ser Lys
1               5

<210> SEQ ID NO 165
<211> LENGTH: 8
<212> TYPE: PRT
<213> ORGANISM: Homo sapiens

<400> SEQUENCE: 165

Cys Lys Ile Arg Val Phe Ser Lys
1               5

<210> SEQ ID NO 166
<211> LENGTH: 14
<212> TYPE: PRT
<213> ORGANISM: Homo sapiens

<400> SEQUENCE: 166

Phe Phe Lys Arg Thr Val Gln Lys Met Gln Asn Thr Cys Val
1               5                   10

<210> SEQ ID NO 167
<211> LENGTH: 15
<212> TYPE: PRT
<213> ORGANISM: Homo sapiens

<400> SEQUENCE: 167

Phe Phe Lys Arg Thr Val Gln Lys Lys Met Gln Asn Thr Cys Val
1               5                   10                  15

<210> SEQ ID NO 168
<211> LENGTH: 17
<212> TYPE: PRT
<213> ORGANISM: Homo sapiens

```
<400> SEQUENCE: 168

Phe Phe Lys Arg Thr Val Gln Lys Cys Lys Ile Arg Val Phe Ser
1               5                   10                  15
Lys

<210> SEQ ID NO 169
<211> LENGTH: 16
<212> TYPE: PRT
<213> ORGANISM: Homo sapiens

<400> SEQUENCE: 169

Phe Phe Lys Arg Thr Val Gln Lys Cys Lys Ile Arg Val Phe Ser Lys
1               5                   10                  15

<210> SEQ ID NO 170
<211> LENGTH: 7
<212> TYPE: PRT
<213> ORGANISM: Homo sapiens

<400> SEQUENCE: 170

Leu Pro His Tyr Leu Ala His
1               5

<210> SEQ ID NO 171
<211> LENGTH: 8
<212> TYPE: PRT
<213> ORGANISM: Homo sapiens

<400> SEQUENCE: 171

Cys Leu Ile Thr Trp Leu Thr Asn
1               5

<210> SEQ ID NO 172
<211> LENGTH: 17
<212> TYPE: PRT
<213> ORGANISM: Homo sapiens

<400> SEQUENCE: 172

Gly Ser Thr Thr Gly Leu Ser Ala Thr Pro Leu Pro His Tyr Leu Ala
1               5                   10                  15
His

<210> SEQ ID NO 173
<211> LENGTH: 18
<212> TYPE: PRT
<213> ORGANISM: Homo sapiens

<400> SEQUENCE: 173

Gly Ser Thr Thr Gly Leu Ser Ala Thr Pro Pro Leu Pro His Tyr Leu
1               5                   10                  15
Ala His

<210> SEQ ID NO 174
<211> LENGTH: 19
<212> TYPE: PRT
<213> ORGANISM: Homo sapiens

<400> SEQUENCE: 174

Gly Ser Thr Thr Gly Leu Ser Ala Thr Pro Pro Cys Leu Ile Thr Trp
1               5                   10                  15
Leu Thr Asn
```

```
<210> SEQ ID NO 175
<211> LENGTH: 18
<212> TYPE: PRT
<213> ORGANISM: Homo sapiens

<400> SEQUENCE: 175

Gly Ser Thr Thr Gly Leu Ser Ala Thr Pro Cys Leu Ile Thr Trp Leu
1               5                   10                  15
Thr Asn

<210> SEQ ID NO 176
<211> LENGTH: 9
<212> TYPE: PRT
<213> ORGANISM: Homo sapiens

<400> SEQUENCE: 176

Arg Phe Ala Asp Lys Pro Arg Pro Asn
1               5

<210> SEQ ID NO 177
<211> LENGTH: 20
<212> TYPE: PRT
<213> ORGANISM: Homo sapiens

<400> SEQUENCE: 177

Asp Leu Pro Thr Ser Pro Asp Gln Thr Arg Ser Gly Pro Val His Val
1               5                   10                  15
Ser Val Glu Pro
            20

<210> SEQ ID NO 178
<211> LENGTH: 19
<212> TYPE: PRT
<213> ORGANISM: Homo sapiens

<400> SEQUENCE: 178

Asp Ser Ala Ala Gly Cys Ser Gly Thr Pro Arg Phe Ala Asp Lys Pro
1               5                   10                  15
Arg Pro Asn

<210> SEQ ID NO 179
<211> LENGTH: 20
<212> TYPE: PRT
<213> ORGANISM: Homo sapiens

<400> SEQUENCE: 179

Asp Ser Ala Ala Gly Cys Ser Gly Thr Pro Pro Arg Phe Ala Asp Lys
1               5                   10                  15
Pro Arg Pro Asn
            20

<210> SEQ ID NO 180
<211> LENGTH: 31
<212> TYPE: PRT
<213> ORGANISM: Homo sapiens

<400> SEQUENCE: 180

Asp Ser Ala Ala Gly Cys Ser Gly Thr Pro Pro Asp Leu Pro Thr Ser
1               5                   10                  15
Pro Asp Gln Thr Arg Ser Gly Pro Val His Val Ser Val Glu Pro
            20                  25                  30
```

<210> SEQ ID NO 181
<211> LENGTH: 30
<212> TYPE: PRT
<213> ORGANISM: Homo sapiens

<400> SEQUENCE: 181

Asp Ser Ala Ala Gly Cys Ser Gly Thr Pro Asp Leu Pro Thr Ser Pro
1               5                   10                  15

Asp Gln Thr Arg Ser Gly Pro Val His Val Ser Val Glu Pro
            20                  25                  30

<210> SEQ ID NO 182
<211> LENGTH: 53
<212> TYPE: PRT
<213> ORGANISM: Homo sapiens

<400> SEQUENCE: 182

Ala His Pro Glu Thr Pro Ala Gln Asn Arg Leu Arg Ile Pro Cys Ser
1               5                   10                  15

Arg Arg Glu Val Arg Ser Arg Ala Cys Lys Pro Pro Gly Ala Gln Gly
            20                  25                  30

Ser Asp Glu Arg Arg Gly Lys Ala Ser Pro Gly Arg Asp Cys Asp Val
        35                  40                  45

Arg Thr Gly Arg Pro
    50

<210> SEQ ID NO 183
<211> LENGTH: 54
<212> TYPE: PRT
<213> ORGANISM: Homo sapiens

<400> SEQUENCE: 183

Pro Ala His Pro Glu Thr Pro Ala Gln Asn Arg Leu Arg Ile Pro Cys
1               5                   10                  15

Ser Arg Arg Glu Val Arg Ser Arg Ala Cys Lys Pro Pro Gly Ala Gln
            20                  25                  30

Gly Ser Asp Glu Arg Arg Gly Lys Ala Ser Pro Gly Arg Asp Cys Asp
        35                  40                  45

Val Arg Thr Gly Arg Pro
    50

<210> SEQ ID NO 184
<211> LENGTH: 20
<212> TYPE: PRT
<213> ORGANISM: Homo sapiens

<400> SEQUENCE: 184

Arg Pro Thr Arg Arg His Pro Arg Ile Ala Ser Gly Ser Pro Ala
1               5                   10                  15

Val Gly Gly Arg
            20

<210> SEQ ID NO 185
<211> LENGTH: 63
<212> TYPE: PRT
<213> ORGANISM: Homo sapiens

<400> SEQUENCE: 185

Val Ala Ile Arg Gly His Pro Arg Pro Ala His Pro Glu Thr Pro
1               5                   10                  15

```
Ala Gln Asn Arg Leu Arg Ile Pro Cys Ser Arg Arg Glu Val Arg Ser
            20                  25                  30

Arg Ala Cys Lys Pro Pro Gly Ala Gln Gly Ser Asp Glu Arg Arg Gly
        35                  40                  45

Lys Ala Ser Pro Gly Arg Asp Cys Asp Val Arg Thr Gly Arg Pro
    50                  55                  60

<210> SEQ ID NO 186
<211> LENGTH: 64
<212> TYPE: PRT
<213> ORGANISM: Homo sapiens

<400> SEQUENCE: 186

Val Ala Ile Arg Gly His Pro Arg Pro Pro Ala His Pro Glu Thr
1               5                   10                  15

Pro Ala Gln Asn Arg Leu Arg Ile Pro Cys Ser Arg Arg Glu Val Arg
            20                  25                  30

Ser Arg Ala Cys Lys Pro Pro Gly Ala Gln Gly Ser Asp Glu Arg Arg
        35                  40                  45

Gly Lys Ala Ser Pro Gly Arg Asp Cys Asp Val Arg Thr Gly Arg Pro
    50                  55                  60

<210> SEQ ID NO 187
<211> LENGTH: 30
<212> TYPE: PRT
<213> ORGANISM: Homo sapiens

<400> SEQUENCE: 187

Val Ala Ile Arg Gly His Pro Arg Pro Pro Arg Pro Thr Arg Arg His
1               5                   10                  15

Pro Arg Arg Ile Ala Ser Gly Ser Pro Ala Val Gly Gly Arg
            20                  25                  30

<210> SEQ ID NO 188
<211> LENGTH: 29
<212> TYPE: PRT
<213> ORGANISM: Homo sapiens

<400> SEQUENCE: 188

Val Ala Ile Arg Gly His Pro Arg Pro Arg Pro Thr Arg Arg His Pro
1               5                   10                  15

Arg Arg Ile Ala Ser Gly Ser Pro Ala Val Gly Gly Arg
            20                  25

<210> SEQ ID NO 189
<211> LENGTH: 85
<212> TYPE: PRT
<213> ORGANISM: Homo sapiens

<400> SEQUENCE: 189

Arg Gly Arg Thr Ser Gly Arg Ser Leu Ser Cys Cys Arg Arg Pro Arg
1               5                   10                  15

Cys Arg Pro Ala Val Ala Ser Arg Ser Thr Ala Pro Ser Pro Arg Ala
            20                  25                  30

Gly Ser Arg Arg Cys Cys Leu Arg Thr Ser Cys Gly Ala Ala Arg Pro
        35                  40                  45

Arg Arg Thr Arg Ser Ala Cys Gly Asp Trp Val Ala Ser Pro Pro Thr
    50                  55                  60
```

Arg Ser Ser Arg Thr Ala Cys Gly Ala Ala Ser Pro Pro Ala Arg
65                  70                  75                  80

Ser Trp Ser Ala Pro
                85

<210> SEQ ID NO 190
<211> LENGTH: 8
<212> TYPE: PRT
<213> ORGANISM: Homo sapiens

<400> SEQUENCE: 190

Gly Gly Gly His Leu Glu Glu Val
1               5

<210> SEQ ID NO 191
<211> LENGTH: 94
<212> TYPE: PRT
<213> ORGANISM: Homo sapiens

<400> SEQUENCE: 191

Tyr Phe Gly Gly Pro Asp Ser Thr Pro Arg Gly Arg Thr Ser Gly Arg
1               5                   10                  15

Ser Leu Ser Cys Cys Arg Arg Pro Arg Cys Arg Pro Ala Val Ala Ser
            20                  25                  30

Arg Ser Thr Ala Pro Ser Pro Arg Ala Gly Ser Arg Arg Cys Cys Leu
        35                  40                  45

Arg Thr Ser Cys Gly Ala Ala Arg Pro Arg Arg Thr Arg Ser Ala Cys
    50                  55                  60

Gly Asp Trp Val Ala Ser Pro Pro Thr Arg Ser Ser Ser Arg Thr Ala
65                  70                  75                  80

Cys Gly Ala Ala Ser Pro Pro Ala Arg Ser Trp Ser Ala Pro
                85                  90

<210> SEQ ID NO 192
<211> LENGTH: 95
<212> TYPE: PRT
<213> ORGANISM: Homo sapiens

<400> SEQUENCE: 192

Tyr Phe Gly Gly Pro Asp Ser Thr Pro Pro Arg Gly Arg Thr Ser Gly
1               5                   10                  15

Arg Ser Leu Ser Cys Cys Arg Arg Pro Arg Cys Arg Pro Ala Val Ala
                20                  25                  30

Ser Arg Ser Thr Ala Pro Ser Pro Arg Ala Gly Ser Arg Arg Cys Cys
            35                  40                  45

Leu Arg Thr Ser Cys Gly Ala Ala Arg Pro Arg Arg Thr Arg Ser Ala
        50                  55                  60

Cys Gly Asp Trp Val Ala Ser Pro Pro Thr Arg Ser Ser Ser Arg Thr
65                  70                  75                  80

Ala Cys Gly Ala Ala Ser Pro Pro Ala Arg Ser Trp Ser Ala Pro
                85                  90                  95

<210> SEQ ID NO 193
<211> LENGTH: 18
<212> TYPE: PRT
<213> ORGANISM: Homo sapiens

```
<400> SEQUENCE: 193

Tyr Phe Gly Gly Pro Asp Ser Thr Pro Gly Gly Gly His Leu Glu
1               5                   10                  15

Glu Val

<210> SEQ ID NO 194
<211> LENGTH: 17
<212> TYPE: PRT
<213> ORGANISM: Homo sapiens

<400> SEQUENCE: 194

Tyr Phe Gly Gly Pro Asp Ser Thr Pro Gly Gly Gly His Leu Glu Glu
1               5                   10                  15

Val

<210> SEQ ID NO 195
<211> LENGTH: 6
<212> TYPE: PRT
<213> ORGANISM: Homo sapiens

<400> SEQUENCE: 195

His Arg Val Ala Asp Pro
1               5

<210> SEQ ID NO 196
<211> LENGTH: 13
<212> TYPE: PRT
<213> ORGANISM: Homo sapiens

<400> SEQUENCE: 196

Leu Ser Gln Ser Ser Glu Leu Asp Pro Pro Ser Ser Arg
1               5                   10

<210> SEQ ID NO 197
<211> LENGTH: 14
<212> TYPE: PRT
<213> ORGANISM: Homo sapiens

<400> SEQUENCE: 197

Leu Ser Gln Ser Ser Glu Leu Asp Pro Pro Pro Ser Ser Arg
1               5                   10

<210> SEQ ID NO 198
<211> LENGTH: 16
<212> TYPE: PRT
<213> ORGANISM: Homo sapiens

<400> SEQUENCE: 198

Leu Ser Gln Ser Ser Glu Leu Asp Pro Pro His Arg Val Ala Asp Pro
1               5                   10                  15

<210> SEQ ID NO 199
<211> LENGTH: 15
<212> TYPE: PRT
<213> ORGANISM: Homo sapiens

<400> SEQUENCE: 199

Leu Ser Gln Ser Ser Glu Leu Asp Pro His Arg Val Ala Asp Pro
1               5                   10                  15
```

<210> SEQ ID NO 200
<211> LENGTH: 11
<212> TYPE: PRT
<213> ORGANISM: Homo sapiens

<400> SEQUENCE: 200

Val Ile Leu Leu Pro Glu Asp Thr Pro Pro Ser
1               5                   10

<210> SEQ ID NO 201
<211> LENGTH: 12
<212> TYPE: PRT
<213> ORGANISM: Homo sapiens

<400> SEQUENCE: 201

Val Ile Leu Leu Pro Glu Asp Thr Pro Pro Pro Ser
1               5                   10

<210> SEQ ID NO 202
<211> LENGTH: 14
<212> TYPE: PRT
<213> ORGANISM: Homo sapiens

<400> SEQUENCE: 202

Val Ile Leu Leu Pro Glu Asp Thr Pro Pro Leu Leu Arg Ala
1               5                   10

<210> SEQ ID NO 203
<211> LENGTH: 13
<212> TYPE: PRT
<213> ORGANISM: Homo sapiens

<400> SEQUENCE: 203

Val Ile Leu Leu Pro Glu Leu Asp Pro Leu Leu Arg Ala
1               5                   10

<210> SEQ ID NO 204
<211> LENGTH: 5
<212> TYPE: PRT
<213> ORGANISM: Homo sapiens

<400> SEQUENCE: 204

Pro Ser Pro Leu Pro
1               5

<210> SEQ ID NO 205
<211> LENGTH: 25
<212> TYPE: PRT
<213> ORGANISM: Homo sapiens

<400> SEQUENCE: 205

Pro Leu Leu Phe His Arg Pro Cys Ser Pro Ser Pro Ala Leu Gly Ala
1               5                   10                  15
Thr Val Leu Ala Val Tyr Arg Tyr Glu
            20                  25

<210> SEQ ID NO 206
<211> LENGTH: 24
<212> TYPE: PRT
<213> ORGANISM: Homo sapiens

<400> SEQUENCE: 206

Leu Leu Phe His Arg Pro Cys Ser Pro Ser Pro Ala Leu Gly Ala Thr
1               5                   10                  15
Val Leu Ala Val Tyr Arg Tyr Glu
            20

<210> SEQ ID NO 207
<211> LENGTH: 13
<212> TYPE: PRT
<213> ORGANISM: Homo sapiens

<400> SEQUENCE: 207

Ala Pro Arg Pro Pro Leu Gly Pro Pro Ser Pro Leu Pro
1               5                   10

<210> SEQ ID NO 208
<211> LENGTH: 14
<212> TYPE: PRT
<213> ORGANISM: Homo sapiens

<400> SEQUENCE: 208

Ala Pro Arg Pro Pro Leu Gly Pro Pro Pro Ser Pro Leu Pro
1               5                   10

<210> SEQ ID NO 209
<211> LENGTH: 34
<212> TYPE: PRT
<213> ORGANISM: Homo sapiens

<400> SEQUENCE: 209

Ala Pro Arg Pro Pro Leu Gly Pro Pro Leu Leu Phe His Arg Pro
1               5                   10                  15
Cys Ser Pro Ser Pro Ala Leu Gly Ala Thr Val Leu Ala Val Tyr Arg
            20                  25                  30
Tyr Glu

<210> SEQ ID NO 210
<211> LENGTH: 33
<212> TYPE: PRT
<213> ORGANISM: Homo sapiens

<400> SEQUENCE: 210

Ala Pro Arg Pro Pro Leu Gly Pro Pro Leu Leu Phe His Arg Pro Cys
1               5                   10                  15
Ser Pro Ser Pro Ala Leu Gly Ala Thr Val Leu Ala Val Tyr Arg Tyr
            20                  25                  30
Glu

<210> SEQ ID NO 211
<211> LENGTH: 28
<212> TYPE: PRT
<213> ORGANISM: Homo sapiens

<400> SEQUENCE: 211

Thr Gln Val Leu Pro Gln Gly Cys Ser Leu Ser Leu Leu His Thr Thr
1               5                   10                  15
Phe Pro His Arg Gln Val Pro His Ile Leu Asp Trp
            20                  25

-continued

<210> SEQ ID NO 212
<211> LENGTH: 29
<212> TYPE: PRT
<213> ORGANISM: Homo sapiens

<400> SEQUENCE: 212

Pro Thr Gln Val Leu Pro Gln Gly Cys Ser Leu Ser Leu Leu His Thr
1               5                   10                  15

Thr Phe Pro His Arg Gln Val Pro His Ile Leu Asp Trp
            20                  25

<210> SEQ ID NO 213
<211> LENGTH: 54
<212> TYPE: PRT
<213> ORGANISM: Homo sapiens

<400> SEQUENCE: 213

Pro Leu Gln Ser Phe Pro Lys Asp Ala Ala Ser Ala Phe Ser Thr Pro
1               5                   10                  15

Arg Phe Pro Thr Asp Lys Phe Pro Thr Ser Trp Thr Gly Ser Cys Pro
            20                  25                  30

Gly Gln Pro His Gly Thr Arg Ala Phe Cys Gln Pro Gly Pro Glu Phe
        35                  40                  45

Asn Ala Phe Ser Ala Cys
    50

<210> SEQ ID NO 214
<211> LENGTH: 53
<212> TYPE: PRT
<213> ORGANISM: Homo sapiens

<400> SEQUENCE: 214

Leu Gln Ser Phe Pro Lys Asp Ala Ala Ser Ala Phe Ser Thr Pro Arg
1               5                   10                  15

Phe Pro Thr Asp Lys Phe Pro Thr Ser Trp Thr Gly Ser Cys Pro Gly
            20                  25                  30

Gln Pro His Gly Thr Arg Ala Phe Cys Gln Pro Gly Pro Glu Phe Asn
        35                  40                  45

Ala Phe Ser Ala Cys
    50

<210> SEQ ID NO 215
<211> LENGTH: 38
<212> TYPE: PRT
<213> ORGANISM: Homo sapiens

<400> SEQUENCE: 215

Pro Ser Pro Arg Pro Gln Ser Gln Pro Pro Thr Gln Val Leu Pro Gln
1               5                   10                  15

Gly Cys Ser Leu Ser Leu Leu His Thr Thr Phe Pro His Arg Gln Val
            20                  25                  30

Pro His Ile Leu Asp Trp
        35

<210> SEQ ID NO 216
<211> LENGTH: 39
<212> TYPE: PRT
<213> ORGANISM: Homo sapiens -continued

```
<400> SEQUENCE: 216

Pro Ser Pro Arg Pro Gln Ser Gln Pro Pro Thr Gln Val Leu Pro
1               5                   10                  15

Gln Gly Cys Ser Leu Ser Leu Leu His Thr Thr Phe Pro His Arg Gln
            20                  25                  30

Val Pro His Ile Leu Asp Trp
        35

<210> SEQ ID NO 217
<211> LENGTH: 64
<212> TYPE: PRT
<213> ORGANISM: Homo sapiens

<400> SEQUENCE: 217

Pro Ser Pro Arg Pro Gln Ser Gln Pro Pro Leu Gln Ser Phe Pro
1               5                   10                  15

Lys Asp Ala Ala Ser Ala Phe Ser Thr Pro Arg Phe Pro Thr Asp Lys
            20                  25                  30

Phe Pro Thr Ser Trp Thr Gly Ser Cys Pro Gly Gln Pro His Gly Thr
        35                  40                  45

Arg Ala Phe Cys Gln Pro Gly Pro Glu Phe Asn Ala Phe Ser Ala Cys
    50                  55                  60

<210> SEQ ID NO 218
<211> LENGTH: 63
<212> TYPE: PRT
<213> ORGANISM: Homo sapiens

<400> SEQUENCE: 218

Pro Ser Pro Arg Pro Gln Ser Gln Pro Pro Leu Gln Ser Phe Pro Lys
1               5                   10                  15

Asp Ala Ala Ser Ala Phe Ser Thr Pro Arg Phe Pro Thr Asp Lys Phe
            20                  25                  30

Pro Thr Ser Trp Thr Gly Ser Cys Pro Gly Gln Pro His Gly Thr Arg
        35                  40                  45

Ala Phe Cys Gln Pro Gly Pro Glu Phe Asn Ala Phe Ser Ala Cys
    50                  55                  60

<210> SEQ ID NO 219
<211> LENGTH: 30
<212> TYPE: PRT
<213> ORGANISM: Homo sapiens

<400> SEQUENCE: 219

Thr Ala Trp Pro Gly Arg Arg Arg Phe Thr Thr Pro Glu Pro Tyr Cys
1               5                   10                  15

Leu Cys Thr Pro Leu Gly Pro Trp Ala Pro Arg Phe Leu Trp
            20                  25                  30

<210> SEQ ID NO 220
<211> LENGTH: 31
<212> TYPE: PRT
<213> ORGANISM: Homo sapiens

<400> SEQUENCE: 220

Pro Thr Ala Trp Pro Gly Arg Arg Arg Phe Thr Thr Pro Glu Pro Tyr
1               5                   10                  15

Cys Leu Cys Thr Pro Leu Gly Pro Trp Ala Pro Arg Phe Leu Trp
            20                  25                  30
```

<210> SEQ ID NO 221
<211> LENGTH: 50
<212> TYPE: PRT
<213> ORGANISM: Homo sapiens

<400> SEQUENCE: 221

```
Pro Arg Pro Gly Pro Ala Gly Gly Ala Leu Leu Pro Arg Ser Leu Thr
1               5                   10                  15
Ala Phe Val Pro His Ser Gly His Gly Leu Pro Val Ser Ser Gly Glu
            20                  25                  30
Pro Ala Tyr Thr Pro Ile Pro His Asp Val Pro His Gly Thr Pro Pro
        35                  40                  45
Phe Cys
    50
```

<210> SEQ ID NO 222
<211> LENGTH: 49
<212> TYPE: PRT
<213> ORGANISM: Homo sapiens

<400> SEQUENCE: 222

```
Arg Pro Gly Pro Ala Gly Gly Ala Leu Leu Pro Arg Ser Leu Thr Ala
1               5                   10                  15
Phe Val Pro His Ser Gly His Gly Leu Pro Val Ser Ser Gly Glu Pro
            20                  25                  30
Ala Tyr Thr Pro Ile Pro His Asp Val Pro His Gly Thr Pro Pro Phe
        35                  40                  45
Cys
```

<210> SEQ ID NO 223
<211> LENGTH: 39
<212> TYPE: PRT
<213> ORGANISM: Homo sapiens

<400> SEQUENCE: 223

```
Asp Leu Pro Ala Val Pro Gly Pro Pro Thr Ala Trp Pro Gly Arg Arg
1               5                   10                  15
Arg Phe Thr Thr Pro Glu Pro Tyr Cys Leu Cys Thr Pro Leu Gly Pro
            20                  25                  30
Trp Ala Pro Arg Phe Leu Trp
        35
```

<210> SEQ ID NO 224
<211> LENGTH: 40
<212> TYPE: PRT
<213> ORGANISM: Homo sapiens

<400> SEQUENCE: 224

```
Asp Leu Pro Ala Val Pro Gly Pro Pro Thr Ala Trp Pro Gly Arg
1               5                   10                  15
Arg Arg Phe Thr Thr Pro Glu Pro Tyr Cys Leu Cys Thr Pro Leu Gly
            20                  25                  30
Pro Trp Ala Pro Arg Phe Leu Trp
        35                  40
```

<210> SEQ ID NO 225
<211> LENGTH: 59
<212> TYPE: PRT
<213> ORGANISM: Homo sapiens -continued

```
<400> SEQUENCE: 225

Asp Leu Pro Ala Val Pro Gly Pro Pro Arg Pro Gly Pro Ala Gly
1               5                   10                  15

Gly Ala Leu Leu Pro Arg Ser Leu Thr Ala Phe Val Pro His Ser Gly
                20                  25                  30

His Gly Leu Pro Val Ser Ser Gly Glu Pro Ala Tyr Thr Pro Ile Pro
            35                  40                  45

His Asp Val Pro His Gly Thr Pro Pro Phe Cys
    50                  55

<210> SEQ ID NO 226
<211> LENGTH: 58
<212> TYPE: PRT
<213> ORGANISM: Homo sapiens

<400> SEQUENCE: 226

Asp Leu Pro Ala Val Pro Gly Pro Pro Arg Pro Gly Pro Ala Gly Gly
1               5                   10                  15

Ala Leu Leu Pro Arg Ser Leu Thr Ala Phe Val Pro His Ser Gly His
                20                  25                  30

Gly Leu Pro Val Ser Ser Gly Glu Pro Ala Tyr Thr Pro Ile Pro His
            35                  40                  45

Asp Val Pro His Gly Thr Pro Pro Phe Cys
    50                  55

<210> SEQ ID NO 227
<211> LENGTH: 8
<212> TYPE: PRT
<213> ORGANISM: Homo sapiens

<400> SEQUENCE: 227

Gln Trp Gly Leu Ser Trp Met Ser
1               5

<210> SEQ ID NO 228
<211> LENGTH: 14
<212> TYPE: PRT
<213> ORGANISM: Homo sapiens

<400> SEQUENCE: 228

Asn Gly Asp Cys His Gly Cys Pro Glu Gly Arg Gln Ser Leu
1               5                   10

<210> SEQ ID NO 229
<211> LENGTH: 17
<212> TYPE: PRT
<213> ORGANISM: Homo sapiens

<400> SEQUENCE: 229

Phe Thr Met Asp Arg Val Leu Thr Pro Gln Trp Gly Leu Ser Trp Met
1               5                   10                  15

Ser

<210> SEQ ID NO 230
<211> LENGTH: 18
<212> TYPE: PRT
<213> ORGANISM: Homo sapiens
```

```
<400> SEQUENCE: 230

Phe Thr Met Asp Arg Val Leu Thr Pro Pro Gln Trp Gly Leu Ser Trp
1               5                   10                  15

Met Ser

<210> SEQ ID NO 231
<211> LENGTH: 24
<212> TYPE: PRT
<213> ORGANISM: Homo sapiens

<400> SEQUENCE: 231

Phe Thr Met Asp Arg Val Leu Thr Pro Pro Asn Gly Asp Cys His Gly
1               5                   10                  15

Cys Pro Glu Gly Arg Gln Ser Leu
            20

<210> SEQ ID NO 232
<211> LENGTH: 23
<212> TYPE: PRT
<213> ORGANISM: Homo sapiens

<400> SEQUENCE: 232

Phe Thr Met Asp Arg Val Leu Thr Pro Asn Gly Asp Cys His Gly Cys
1               5                   10                  15

Pro Glu Gly Arg Gln Ser Leu
            20

<210> SEQ ID NO 233
<211> LENGTH: 115
<212> TYPE: PRT
<213> ORGANISM: Homo sapiens

<400> SEQUENCE: 233

His His Pro Ala Arg Gln Cys Pro His Cys Ile Met His Leu Gln Thr
1               5                   10                  15

Gln Leu Ile His Arg Asn Leu Thr Gly Pro Ser Gln Leu Thr Ser Leu
            20                  25                  30

His Arg Ser Pro Tyr Gln Ile Ala Ala Thr Pro Trp Thr Thr Asp Phe
        35                  40                  45

Ala Ala Ser Phe Phe Leu Asn Pro Val Thr Pro Phe Leu Leu Cys Arg
    50                  55                  60

Arg Cys Gln Gly Lys Asp Val Leu Cys Thr Asn Ala Arg Cys Leu Ser
65                  70                  75                  80

Gln Thr Ser Pro Ser His His Lys Ala Leu Ser Arg Thr Thr Thr Gln
                85                  90                  95

Cys Met Asn Thr Thr Pro Trp Leu Ala Val Arg Pro Ala Lys Ala Phe
            100                 105                 110

Pro Leu Leu
        115

<210> SEQ ID NO 234
<211> LENGTH: 116
<212> TYPE: PRT
<213> ORGANISM: Homo sapiens

<400> SEQUENCE: 234

Pro His His Pro Ala Arg Gln Cys Pro His Cys Ile Met His Leu Gln
1               5                   10                  15
```

```
Thr Gln Leu Ile His Arg Asn Leu Thr Gly Pro Ser Gln Leu Thr Ser
            20                  25                  30

Leu His Arg Ser Pro Tyr Gln Ile Ala Ala Thr Pro Trp Thr Thr Asp
        35                  40                  45

Phe Ala Ala Ser Phe Phe Leu Asn Pro Val Thr Pro Phe Leu Leu Cys
    50                  55                  60

Arg Arg Cys Gln Gly Lys Asp Val Leu Cys Thr Asn Ala Arg Cys Leu
65                  70                  75                  80

Ser Gln Thr Ser Pro Ser His His Lys Ala Leu Ser Arg Thr Thr Thr
                85                  90                  95

Gln Cys Met Asn Thr Thr Pro Trp Leu Ala Val Arg Pro Ala Lys Ala
            100                 105                 110

Phe Pro Leu Leu
        115

<210> SEQ ID NO 235
<211> LENGTH: 23
<212> TYPE: PRT
<213> ORGANISM: Homo sapiens

<400> SEQUENCE: 235

His Thr Ile Gln His Ala Ser Val Pro Thr Ala Ser Cys Ile Ser Lys
1               5                   10                  15

Leu Asn Ser Tyr Thr Glu Asn
            20

<210> SEQ ID NO 236
<211> LENGTH: 126
<212> TYPE: PRT
<213> ORGANISM: Homo sapiens

<400> SEQUENCE: 236

Pro Gln Val Gly Met Arg Pro Ser Asn Pro Pro His His Pro Ala Arg
1               5                   10                  15

Gln Cys Pro His Cys Ile Met His Leu Gln Thr Gln Leu Ile His Arg
            20                  25                  30

Asn Leu Thr Gly Pro Ser Gln Leu Thr Ser Leu His Arg Ser Pro Tyr
        35                  40                  45

Gln Ile Ala Ala Thr Pro Trp Thr Thr Asp Phe Ala Ala Ser Phe Phe
    50                  55                  60

Leu Asn Pro Val Thr Pro Phe Leu Leu Cys Arg Arg Cys Gln Gly Lys
65                  70                  75                  80

Asp Val Leu Cys Thr Asn Ala Arg Cys Leu Ser Gln Thr Ser Pro Ser
                85                  90                  95

His His Lys Ala Leu Ser Arg Thr Thr Thr Gln Cys Met Asn Thr Thr
            100                 105                 110

Pro Trp Leu Ala Val Arg Pro Ala Lys Ala Phe Pro Leu Leu
        115                 120                 125

<210> SEQ ID NO 237
<211> LENGTH: 127
<212> TYPE: PRT
<213> ORGANISM: Homo sapiens

<400> SEQUENCE: 237

Pro Gln Val Gly Met Arg Pro Ser Asn Pro Pro His His Pro Ala
1               5                   10                  15
```

-continued

```
Arg Gln Cys Pro His Cys Ile Met His Leu Gln Thr Gln Leu Ile His
         20                  25                  30

Arg Asn Leu Thr Gly Pro Ser Gln Leu Thr Ser Leu His Arg Ser Pro
     35                  40                  45

Tyr Gln Ile Ala Ala Thr Pro Trp Thr Thr Asp Phe Ala Ala Ser Phe
 50                  55                  60

Phe Leu Asn Pro Val Thr Pro Phe Leu Leu Cys Arg Arg Cys Gln Gly
65                   70                  75                  80

Lys Asp Val Leu Cys Thr Asn Ala Arg Cys Leu Ser Gln Thr Ser Pro
                 85                  90                  95

Ser His His Lys Ala Leu Ser Arg Thr Thr Gln Cys Met Asn Thr
                100                 105                 110

Thr Pro Trp Leu Ala Val Arg Pro Ala Lys Ala Phe Pro Leu Leu
        115                 120                 125
```

<210> SEQ ID NO 238
<211> LENGTH: 34
<212> TYPE: PRT
<213> ORGANISM: Homo sapiens

<400> SEQUENCE: 238

```
Pro Gln Val Gly Met Arg Pro Ser Asn Pro His Thr Ile Gln His
1               5                   10                  15

Ala Ser Val Pro Thr Ala Ser Cys Ile Ser Lys Leu Asn Ser Tyr Thr
                 20                  25                  30

Glu Asn
```

<210> SEQ ID NO 239
<211> LENGTH: 33
<212> TYPE: PRT
<213> ORGANISM: Homo sapiens

<400> SEQUENCE: 239

```
Pro Gln Val Gly Met Arg Pro Ser Asn Pro His Thr Ile Gln His Ala
1               5                   10                  15

Ser Val Pro Thr Ala Ser Cys Ile Ser Lys Leu Asn Ser Tyr Thr Glu
                 20                  25                  30

Asn
```

<210> SEQ ID NO 240
<211> LENGTH: 51
<212> TYPE: PRT
<213> ORGANISM: Homo sapiens

<400> SEQUENCE: 240

```
Trp Ala Ala Arg Ser Trp Cys Glu Arg Arg Ala Ala Val Ala Pro
1               5                   10                  15

Leu Ala Pro Trp Ala Trp Gly Cys Pro Ala Gly Cys Thr Pro Pro Val
                 20                  25                  30

Ala Ala Arg Ala Cys Ala Ala Thr Arg Pro Glu Gly Trp Arg Ser Pro
        35                  40                  45

Cys Thr His
     50
```

<210> SEQ ID NO 241
<211> LENGTH: 52
<212> TYPE: PRT
<213> ORGANISM: Homo sapiens

```
<400> SEQUENCE: 241

Pro Trp Ala Ala Arg Ser Trp Cys Glu Arg Ala Ala Val Ala
1               5                   10                  15

Pro Leu Ala Pro Trp Ala Trp Gly Cys Pro Ala Gly Cys Thr Pro Pro
            20                  25                  30

Val Ala Ala Arg Ala Cys Ala Ala Thr Arg Pro Glu Gly Trp Arg Ser
        35                  40                  45

Pro Cys Thr His
    50

<210> SEQ ID NO 242
<211> LENGTH: 74
<212> TYPE: PRT
<213> ORGANISM: Homo sapiens

<400> SEQUENCE: 242

Arg Gly Leu Arg Gly Ala Gly Ala Arg Gly Gly Leu Arg Leu Arg
1               5                   10                  15

His Leu Arg Pro Gly Leu Gly Asp Ala Leu Arg Gly Val His Pro Pro
            20                  25                  30

Leu Arg Leu Gly Pro Ala Leu Leu Pro Ala Pro Arg Gly Gly Glu Ala
        35                  40                  45

Pro Ala His Thr Asp Ala Arg Ala Arg Arg Val His Gly Ala Gly Gly
    50                  55                  60

Asp Arg Gly His Pro Gly Pro Ala Ala Leu
65                  70

<210> SEQ ID NO 243
<211> LENGTH: 61
<212> TYPE: PRT
<213> ORGANISM: Homo sapiens

<400> SEQUENCE: 243

Glu Glu Lys Leu Ala Arg Cys Arg Pro Pro Trp Ala Ala Arg Ser Trp
1               5                   10                  15

Cys Glu Arg Arg Ala Ala Ala Val Ala Pro Leu Ala Pro Trp Ala Trp
            20                  25                  30

Gly Cys Pro Ala Gly Cys Thr Pro Pro Val Ala Ala Arg Ala Cys Ala
        35                  40                  45

Ala Thr Arg Pro Glu Gly Trp Arg Ser Pro Cys Thr His
    50                  55                  60

<210> SEQ ID NO 244
<211> LENGTH: 62
<212> TYPE: PRT
<213> ORGANISM: Homo sapiens

<400> SEQUENCE: 244

Glu Glu Lys Leu Ala Arg Cys Arg Pro Pro Trp Ala Ala Arg Ser
1               5                   10                  15

Trp Cys Glu Arg Arg Ala Ala Ala Val Ala Pro Leu Ala Pro Trp Ala
            20                  25                  30

Trp Gly Cys Pro Ala Gly Cys Thr Pro Pro Val Ala Ala Arg Ala Cys
        35                  40                  45

Ala Ala Thr Arg Pro Glu Gly Trp Arg Ser Pro Cys Thr His
    50                  55                  60
```

-continued

<210> SEQ ID NO 245
<211> LENGTH: 84
<212> TYPE: PRT
<213> ORGANISM: Homo sapiens

<400> SEQUENCE: 245

Glu Glu Lys Leu Ala Arg Cys Arg Pro Pro Arg Gly Leu Arg Gly Ala
1               5                   10                  15

Gly Ala Arg Gly Gly Leu Arg Leu Leu Arg His Leu Arg Pro Gly Leu
            20                  25                  30

Gly Asp Ala Leu Arg Gly Val His Pro Pro Leu Arg Leu Gly Pro Ala
        35                  40                  45

Leu Leu Pro Ala Pro Arg Gly Gly Glu Ala Pro Ala His Thr Asp Ala
    50                  55                  60

Arg Ala Arg Arg Val His Gly Ala Gly Gly Asp Arg Gly His Pro Gly
65                  70                  75                  80

Pro Ala Ala Leu

<210> SEQ ID NO 246
<211> LENGTH: 83
<212> TYPE: PRT
<213> ORGANISM: Homo sapiens

<400> SEQUENCE: 246

Glu Glu Lys Leu Ala Arg Cys Arg Pro Arg Gly Leu Arg Gly Ala Gly
1               5                   10                  15

Ala Arg Gly Gly Leu Arg Leu Leu Arg His Leu Arg Pro Gly Leu Gly
            20                  25                  30

Asp Ala Leu Arg Gly Val His Pro Pro Leu Arg Leu Gly Pro Ala Leu
        35                  40                  45

Leu Pro Ala Pro Arg Gly Gly Glu Ala Pro Ala His Thr Asp Ala Arg
    50                  55                  60

Ala Arg Arg Val His Gly Ala Gly Gly Asp Arg Gly His Pro Gly Pro
65                  70                  75                  80

Ala Ala Leu

<210> SEQ ID NO 247
<211> LENGTH: 163
<212> TYPE: PRT
<213> ORGANISM: Homo sapiens

<400> SEQUENCE: 247

Gln Pro Pro Val Ser Pro Arg Pro Arg Pro Gly Arg Pro Arg Ala
1               5                   10                  15

Pro Pro Pro Pro Gln Pro Met Val Ser Pro Arg Arg Arg Thr Thr Gly
            20                  25                  30

Pro Pro Trp Arg Pro Pro Leu Gln Ser Thr Met Ser Pro Pro
        35                  40                  45

Gln Ala Leu His Gln Ala Gln Leu Leu Leu Trp Cys Thr Thr Ala Pro
    50                  55                  60

Leu Pro Gly Leu Pro Gln Pro Gln Pro Ala Arg Ala Leu His Ser Gln
65                  70                  75                  80

Phe Pro Ala Thr Thr Leu Ile Leu Leu Pro Pro Leu Pro Ala Ile Ala
                85                  90                  95

Pro Arg Leu Met Pro Val Ala Leu Thr Ile Ala Arg Tyr Leu Leu Ser
                100                 105                 110

```
Pro Pro Pro Ile Thr Ala Leu Leu Pro Ser Cys Leu Leu Gly Ser Leu
        115                 120                 125

Ser Phe Ser Cys Leu Phe Thr Phe Gln Thr Ser Ser Leu Ile Pro Leu
    130                 135                 140

Trp Lys Ile Pro Ala Pro Thr Thr Lys Ser Cys Arg Glu Thr Phe
145                 150                 155                 160

Leu Lys Trp

<210> SEQ ID NO 248
<211> LENGTH: 85
<212> TYPE: PRT
<213> ORGANISM: Homo sapiens

<400> SEQUENCE: 248

Ser Pro Gly Cys His Leu Gly Pro Gly Asp Gln Ala Ala Pro Gly Leu
1               5                   10                  15

His Arg Pro Pro Ser Pro Trp Cys His Leu Gly Ala Gly Gln Gln Ala
            20                  25                  30

Arg Leu Gly Val His Arg Pro Ser Pro Gln Cys His Leu Gly Leu
        35                  40                  45

Arg Leu Cys Ile Arg Leu Ser Phe Tyr Ser Gly Ala Gln Arg His Leu
    50                  55                  60

Cys Gln Gly Tyr His Asn Pro Ser Gln Gln Glu His Ser Ile Leu Asn
65                  70                  75                  80

Ser Gln Pro Pro Leu
                85

<210> SEQ ID NO 249
<211> LENGTH: 172
<212> TYPE: PRT
<213> ORGANISM: Homo sapiens

<400> SEQUENCE: 249

Lys Pro Ala Pro Gly Ser Thr Ala Pro Gln Pro Val Ser Pro Arg
1               5                   10                  15

Pro Arg Arg Pro Gly Arg Pro Arg Ala Pro Pro Pro Gln Pro Met
            20                  25                  30

Val Ser Pro Arg Arg Thr Thr Gly Pro Pro Trp Arg Pro Pro Pro
        35                  40                  45

Leu Gln Ser Thr Met Ser Pro Pro Gln Ala Leu His Gln Ala Gln
    50                  55                  60

Leu Leu Leu Trp Cys Thr Thr Ala Pro Leu Pro Gly Leu Pro Gln Pro
65                  70                  75                  80

Gln Pro Ala Arg Ala Leu His Ser Gln Phe Pro Ala Thr Thr Leu Ile
            85                  90                  95

Leu Leu Pro Pro Leu Pro Ala Ile Ala Pro Arg Leu Met Pro Val Ala
                100                 105                 110

Leu Thr Ile Ala Arg Tyr Leu Leu Ser Pro Pro Ile Thr Ala Leu
        115                 120                 125

Leu Pro Ser Cys Leu Leu Gly Ser Leu Ser Phe Ser Cys Leu Phe Thr
    130                 135                 140

Phe Gln Thr Ser Ser Leu Ile Pro Leu Trp Lys Ile Pro Ala Pro Thr
145                 150                 155                 160

Thr Thr Lys Ser Cys Arg Glu Thr Phe Leu Lys Trp
                165                 170
```

```
<210> SEQ ID NO 250
<211> LENGTH: 173
<212> TYPE: PRT
<213> ORGANISM: Homo sapiens

<400> SEQUENCE: 250

Lys Pro Ala Pro Gly Ser Thr Ala Pro Pro Gln Pro Val Ser Pro
1               5                   10                  15

Arg Pro Arg Arg Pro Gly Arg Pro Arg Ala Pro Pro Pro Gln Pro
            20                  25                  30

Met Val Ser Pro Arg Arg Thr Thr Gly Pro Pro Trp Arg Pro Pro
        35                  40                  45

Pro Leu Gln Ser Thr Met Ser Pro Pro Gln Ala Leu His Gln Ala
    50                  55                  60

Gln Leu Leu Leu Trp Cys Thr Thr Ala Pro Leu Pro Gly Leu Pro Gln
65                  70                  75                  80

Pro Gln Pro Ala Arg Ala Leu His Ser Gln Phe Pro Ala Thr Thr Leu
                85                  90                  95

Ile Leu Leu Pro Pro Leu Pro Ala Ile Ala Pro Arg Leu Met Pro Val
                100                 105                 110

Ala Leu Thr Ile Ala Arg Tyr Leu Leu Ser Pro Pro Ile Thr Ala
            115                 120                 125

Leu Leu Pro Ser Cys Leu Leu Gly Ser Leu Ser Phe Ser Cys Leu Phe
    130                 135                 140

Thr Phe Gln Thr Ser Ser Leu Ile Pro Leu Trp Lys Ile Pro Ala Pro
145                 150                 155                 160

Thr Thr Thr Lys Ser Cys Arg Glu Thr Phe Leu Lys Trp
                165                 170

<210> SEQ ID NO 251
<211> LENGTH: 95
<212> TYPE: PRT
<213> ORGANISM: Homo sapiens

<400> SEQUENCE: 251

Lys Pro Ala Pro Gly Ser Thr Ala Pro Pro Ser Pro Gly Cys His Leu
1               5                   10                  15

Gly Pro Gly Asp Gln Ala Ala Pro Gly Leu His Arg Pro Pro Ser Pro
            20                  25                  30

Trp Cys His Leu Gly Ala Gly Gln Gln Ala Arg Leu Gly Val His Arg
        35                  40                  45

Pro Ser Ser Pro Gln Cys His Leu Gly Leu Arg Leu Cys Ile Arg Leu
    50                  55                  60

Ser Phe Tyr Ser Gly Ala Gln Arg His Leu Cys Gln Gly Tyr His Asn
65                  70                  75                  80

Pro Ser Gln Gln Glu His Ser Ile Leu Asn Ser Gln Pro Pro Leu
                85                  90                  95

<210> SEQ ID NO 252
<211> LENGTH: 94
<212> TYPE: PRT
<213> ORGANISM: Homo sapiens

<400> SEQUENCE: 252

Lys Pro Ala Pro Gly Ser Thr Ala Pro Ser Pro Gly Cys His Leu Gly
1               5                   10                  15

Pro Gly Asp Gln Ala Ala Pro Gly Leu His Arg Pro Pro Ser Pro Trp
            20                  25                  30
```

-continued

Cys His Leu Gly Ala Gly Gln Gln Ala Arg Leu Gly Val His Arg Pro
         35                  40                  45

Ser Ser Pro Gln Cys His Leu Gly Leu Arg Leu Cys Ile Arg Leu Ser
 50                  55                  60

Phe Tyr Ser Gly Ala Gln Arg His Leu Cys Gln Gly Tyr His Asn Pro
65                  70                  75                  80

Ser Gln Gln Glu His Ser Ile Leu Asn Ser Gln Pro Pro Leu
                 85                  90

<210> SEQ ID NO 253
<211> LENGTH: 143
<212> TYPE: PRT
<213> ORGANISM: Homo sapiens

<400> SEQUENCE: 253

Gln Pro Met Val Ser Pro Arg Arg Thr Thr Gly Pro Pro Trp Arg
1               5                   10                  15

Pro Pro Pro Leu Gln Ser Thr Met Ser Pro Pro Gln Ala Leu His
                 20                  25                  30

Gln Ala Gln Leu Leu Leu Trp Cys Thr Thr Ala Pro Leu Pro Gly Leu
         35                  40                  45

Pro Gln Pro Gln Pro Ala Arg Ala Leu His Ser Gln Phe Pro Ala Thr
 50                  55                  60

Thr Leu Ile Leu Leu Pro Pro Leu Pro Ala Ile Ala Pro Arg Leu Met
65                  70                  75                  80

Pro Val Ala Leu Thr Ile Ala Arg Tyr Leu Leu Ser Pro Pro Ile
                 85                  90                  95

Thr Ala Leu Leu Pro Ser Cys Leu Leu Gly Ser Leu Ser Phe Ser Cys
             100                 105                 110

Leu Phe Thr Phe Gln Thr Ser Ser Leu Ile Pro Leu Trp Lys Ile Pro
         115                 120                 125

Ala Pro Thr Thr Thr Lys Ser Cys Arg Glu Thr Phe Leu Lys Trp
     130                 135                 140

<210> SEQ ID NO 254
<211> LENGTH: 65
<212> TYPE: PRT
<213> ORGANISM: Homo sapiens

<400> SEQUENCE: 254

Ser Pro Trp Cys His Leu Gly Ala Gly Gln Gln Ala Arg Leu Gly Val
1               5                   10                  15

His Arg Pro Ser Ser Pro Gln Cys His Leu Gly Leu Arg Leu Cys Ile
                 20                  25                  30

Arg Leu Ser Phe Tyr Ser Gly Ala Gln Arg His Leu Cys Gln Gly Tyr
         35                  40                  45

His Asn Pro Ser Gln Gln Glu His Ser Ile Leu Asn Ser Gln Pro Pro
 50                  55                  60

Leu
65

<210> SEQ ID NO 255
<211> LENGTH: 18
<212> TYPE: PRT
<213> ORGANISM: Homo sapiens

<400> SEQUENCE: 255

Arg Pro Pro Pro Gly Ser Thr Ala Pro Gln Pro Met Val Ser Pro Arg
1               5                   10                  15

Arg Arg

<210> SEQ ID NO 256
<211> LENGTH: 19
<212> TYPE: PRT
<213> ORGANISM: Homo sapiens

<400> SEQUENCE: 256

Arg Pro Pro Pro Gly Ser Thr Ala Pro Gln Pro Met Val Ser Pro
1               5                   10                  15

Arg Arg Arg

<210> SEQ ID NO 257
<211> LENGTH: 18
<212> TYPE: PRT
<213> ORGANISM: Homo sapiens

<400> SEQUENCE: 257

Arg Pro Pro Pro Gly Ser Thr Ala Pro Pro Ser Pro Trp Cys His Leu
1               5                   10                  15

Gly Ala

<210> SEQ ID NO 258
<211> LENGTH: 17
<212> TYPE: PRT
<213> ORGANISM: Homo sapiens

<400> SEQUENCE: 258

Arg Pro Pro Pro Gly Ser Thr Ala Pro Ser Pro Trp Cys His Leu Gly
1               5                   10                  15

Ala

<210> SEQ ID NO 259
<211> LENGTH: 14
<212> TYPE: PRT
<213> ORGANISM: Homo sapiens

<400> SEQUENCE: 259

Arg Pro Arg Ala Pro Pro Pro Ser Pro Trp Cys His Leu
1               5                   10

<210> SEQ ID NO 260
<211> LENGTH: 13
<212> TYPE: PRT
<213> ORGANISM: Homo sapiens

<400> SEQUENCE: 260

Arg Pro Arg Ala Pro Pro Pro Ser Pro Trp Cys
1               5                   10

<210> SEQ ID NO 261
<211> LENGTH: 16
<212> TYPE: PRT
<213> ORGANISM: Homo sapiens

<400> SEQUENCE: 261

Arg Pro Arg Ala Pro Pro Pro Ala His Gly Val Thr Ser Ala Pro
1               5                   10                  15

<210> SEQ ID NO 262
<211> LENGTH: 13
<212> TYPE: PRT
<213> ORGANISM: Homo sapiens

<400> SEQUENCE: 262

Arg Pro Arg Ala Pro Pro Pro Pro Ala His Gly Val
1               5                   10

<210> SEQ ID NO 263
<211> LENGTH: 14
<212> TYPE: PRT
<213> ORGANISM: Homo sapiens

<400> SEQUENCE: 263

Ala Pro Gly Leu His Arg Pro Pro Gln Pro Met Val Ser Pro
1               5                   10

<210> SEQ ID NO 264
<211> LENGTH: 15
<212> TYPE: PRT
<213> ORGANISM: Homo sapiens

<400> SEQUENCE: 264

Ala Ala Pro Gly Leu His Arg Pro Gln Pro Met Val Ser Pro Arg
1               5                   10                  15

<210> SEQ ID NO 265
<211> LENGTH: 13
<212> TYPE: PRT
<213> ORGANISM: Homo sapiens

<400> SEQUENCE: 265

Pro Gly Leu His Arg Pro Pro Ala His Gly Val Thr
1               5                   10

<210> SEQ ID NO 266
<211> LENGTH: 14
<212> TYPE: PRT
<213> ORGANISM: Homo sapiens

<400> SEQUENCE: 266

Ala Pro Gly Leu His Arg Pro Pro Ala His Gly Val Thr Ser
1               5                   10

<210> SEQ ID NO 267
<211> LENGTH: 21
<212> TYPE: PRT
<213> ORGANISM: Homo sapiens

<400> SEQUENCE: 267

Val Asp Arg Pro Gln His Thr Glu Trp Leu Ser Trp Ser Asn Leu Tyr
1               5                   10                  15

Arg Ile Arg His Gln
            20

<210> SEQ ID NO 268
<211> LENGTH: 10
<212> TYPE: PRT
<213> ORGANISM: Homo sapiens

<400> SEQUENCE: 268

His Tyr Leu Cys Thr Asp Val Ala Pro Arg
1               5                   10

```
<210> SEQ ID NO 269
<211> LENGTH: 11
<212> TYPE: PRT
<213> ORGANISM: Homo sapiens

<400> SEQUENCE: 269

His Tyr Leu Cys Thr Asp Val Ala Pro Pro Arg
1               5                   10

<210> SEQ ID NO 270
<211> LENGTH: 31
<212> TYPE: PRT
<213> ORGANISM: Homo sapiens

<400> SEQUENCE: 270

His Tyr Leu Cys Thr Asp Val Ala Pro Val Asp Arg Pro Gln His
1               5                   10                  15

Thr Glu Trp Leu Ser Trp Ser Asn Leu Tyr Arg Ile Arg His Gln
            20                  25                  30

<210> SEQ ID NO 271
<211> LENGTH: 30
<212> TYPE: PRT
<213> ORGANISM: Homo sapiens

<400> SEQUENCE: 271

His Tyr Leu Cys Thr Asp Val Ala Pro Val Asp Arg Pro Gln His Thr
1               5                   10                  15

Glu Trp Leu Ser Trp Ser Asn Leu Tyr Arg Ile Arg His Gln
        20                  25                  30

<210> SEQ ID NO 272
<211> LENGTH: 108
<212> TYPE: PRT
<213> ORGANISM: Homo sapiens

<400> SEQUENCE: 272

Ser Ala Tyr Leu Ser Pro Leu Gly Thr Thr Trp Leu Arg Thr Cys Ala
1               5                   10                  15

Cys Arg Leu Pro Arg Pro Ala Ala Ser Cys Leu Cys Thr Thr Pro Ser
            20                  25                  30

Leu Leu Trp Pro Arg Arg Thr Cys Pro Ala Gly Ser Pro Arg Ala Thr
        35                  40                  45

Ser Ser Pro Trp Arg Met Pro Ala Pro Lys Ser Cys Cys Thr Thr Gly
    50                  55                  60

Leu Ala Phe Thr Ser Pro Ile Gly Leu Gly Trp Arg Ser Ala Thr Ala
65                  70                  75                  80

Ser Gly Tyr Ala Arg Ile Trp Pro Val Leu Ser Leu Thr Cys Gln Ser
                85                  90                  95

Trp Ser Thr Ser Leu Pro Ser Thr Ala Val Thr Trp
            100                 105

<210> SEQ ID NO 273
<211> LENGTH: 109
<212> TYPE: PRT
<213> ORGANISM: Homo sapiens

<400> SEQUENCE: 273

Pro Ser Ala Tyr Leu Ser Pro Leu Gly Thr Thr Trp Leu Arg Thr Cys
1               5                   10                  15
```

-continued

Ala Cys Arg Leu Pro Arg Pro Ala Ala Ser Cys Leu Cys Thr Thr Pro
                20                  25                  30

Ser Leu Leu Trp Pro Arg Arg Thr Cys Pro Ala Gly Ser Pro Arg Ala
         35                  40                  45

Thr Ser Ser Pro Trp Arg Met Pro Ala Pro Lys Ser Cys Cys Thr Thr
     50                  55                  60

Gly Leu Ala Phe Thr Ser Pro Ile Gly Leu Gly Trp Arg Ser Ala Thr
 65                  70                  75                  80

Ala Ser Gly Tyr Ala Arg Ile Trp Pro Val Leu Ser Leu Thr Cys Gln
                 85                  90                  95

Ser Trp Ser Thr Ser Leu Pro Ser Thr Ala Val Thr Trp
            100                 105

<210> SEQ ID NO 274
<211> LENGTH: 12
<212> TYPE: PRT
<213> ORGANISM: Homo sapiens

<400> SEQUENCE: 274

Pro Ala Pro Ile Phe Leu Leu Trp Gly Pro Leu Gly
1               5                   10

<210> SEQ ID NO 275
<211> LENGTH: 11
<212> TYPE: PRT
<213> ORGANISM: Homo sapiens

<400> SEQUENCE: 275

Ala Pro Ile Phe Leu Leu Trp Gly Pro Leu Gly
1               5                   10

<210> SEQ ID NO 276
<211> LENGTH: 117
<212> TYPE: PRT
<213> ORGANISM: Homo sapiens

<400> SEQUENCE: 276

Leu Pro Ala Arg Ala Pro Gly Pro Pro Ser Ala Tyr Leu Ser Pro Leu
1               5                   10                  15

Gly Thr Thr Trp Leu Arg Thr Cys Ala Cys Arg Leu Pro Arg Pro Ala
                20                  25                  30

Ala Ser Cys Leu Cys Thr Thr Pro Ser Leu Leu Trp Pro Arg Arg Thr
         35                  40                  45

Cys Pro Ala Gly Ser Pro Arg Ala Thr Ser Ser Pro Trp Arg Met Pro
     50                  55                  60

Ala Pro Lys Ser Cys Cys Thr Thr Gly Leu Ala Phe Thr Ser Pro Ile
 65                  70                  75                  80

Gly Leu Gly Trp Arg Ser Ala Thr Ala Ser Gly Tyr Ala Arg Ile Trp
                 85                  90                  95

Pro Val Leu Ser Leu Thr Cys Gln Ser Trp Ser Thr Ser Leu Pro Ser
            100                 105                 110

Thr Ala Val Thr Trp
            115

<210> SEQ ID NO 277
<211> LENGTH: 118
<212> TYPE: PRT
<213> ORGANISM: Homo sapiens -continued

```
<400> SEQUENCE: 277

Leu Pro Ala Arg Ala Pro Gly Pro Pro Ser Ala Tyr Leu Ser Pro
1               5                   10                  15

Leu Gly Thr Thr Trp Leu Arg Thr Cys Ala Cys Arg Leu Pro Arg Pro
            20                  25                  30

Ala Ala Ser Cys Leu Cys Thr Thr Pro Ser Leu Leu Trp Pro Arg Arg
        35                  40                  45

Thr Cys Pro Ala Gly Ser Pro Arg Ala Thr Ser Ser Pro Trp Arg Met
    50                  55                  60

Pro Ala Pro Lys Ser Cys Cys Thr Thr Gly Leu Ala Phe Thr Ser Pro
65                  70                  75                  80

Ile Gly Leu Gly Trp Arg Ser Ala Thr Ala Ser Gly Tyr Ala Arg Ile
                85                  90                  95

Trp Pro Val Leu Ser Leu Thr Cys Gln Ser Trp Ser Thr Ser Leu Pro
            100                 105                 110

Ser Thr Ala Val Thr Trp
        115

<210> SEQ ID NO 278
<211> LENGTH: 21
<212> TYPE: PRT
<213> ORGANISM: Homo sapiens

<400> SEQUENCE: 278

Leu Pro Ala Arg Ala Pro Gly Pro Pro Ala Pro Ile Phe Leu Leu
1               5                   10                  15

Trp Gly Pro Leu Gly
            20

<210> SEQ ID NO 279
<211> LENGTH: 20
<212> TYPE: PRT
<213> ORGANISM: Homo sapiens

<400> SEQUENCE: 279

Leu Pro Ala Arg Ala Pro Gly Pro Pro Ala Pro Ile Phe Leu Leu Trp
1               5                   10                  15

Gly Pro Leu Gly
            20

<210> SEQ ID NO 280
<211> LENGTH: 14
<212> TYPE: PRT
<213> ORGANISM: Homo sapiens

<400> SEQUENCE: 280

Asp Leu Glu His His Gly Gly Val Thr Arg His Arg His Arg
1               5                   10

<210> SEQ ID NO 281
<211> LENGTH: 11
<212> TYPE: PRT
<213> ORGANISM: Homo sapiens

<400> SEQUENCE: 281

Leu Val Ser Asp Tyr Ser Met Thr Pro Arg Pro
1               5                   10
```

```
<210> SEQ ID NO 282
<211> LENGTH: 12
<212> TYPE: PRT
<213> ORGANISM: Homo sapiens

<400> SEQUENCE: 282

Leu Val Ser Asp Tyr Ser Met Thr Pro Pro Arg Pro
1               5                   10

<210> SEQ ID NO 283
<211> LENGTH: 24
<212> TYPE: PRT
<213> ORGANISM: Homo sapiens

<400> SEQUENCE: 283

Leu Val Ser Asp Tyr Ser Met Thr Pro Asp Leu Glu His His Gly
1               5                   10                  15

Gly Val Thr Arg His Arg His Arg
            20

<210> SEQ ID NO 284
<211> LENGTH: 23
<212> TYPE: PRT
<213> ORGANISM: Homo sapiens

<400> SEQUENCE: 284

Leu Val Ser Asp Tyr Ser Met Thr Pro Asp Leu Glu His His Gly Gly
1               5                   10                  15

Val Thr Arg His Arg His Arg
            20

<210> SEQ ID NO 285
<211> LENGTH: 51
<212> TYPE: PRT
<213> ORGANISM: Homo sapiens

<400> SEQUENCE: 285

Phe His His Ile Ala Thr Asp Val Gly Pro Phe Val Arg Ile Gly Phe
1               5                   10                  15

Leu Lys Ile Lys Gly Lys Ile Lys Gly Lys Ser Leu Arg Lys Pro Asn
            20                  25                  30

Trp Lys Thr Gln His Lys Leu Lys Arg Ala Leu Met Phe Leu Ile Val
        35                  40                  45

Lys Lys Leu
    50

<210> SEQ ID NO 286
<211> LENGTH: 52
<212> TYPE: PRT
<213> ORGANISM: Homo sapiens

<400> SEQUENCE: 286

Pro Phe His His Ile Ala Thr Asp Val Gly Pro Phe Val Arg Ile Gly
1               5                   10                  15

Phe Leu Lys Ile Lys Gly Lys Ile Lys Gly Lys Ser Leu Arg Lys Pro
            20                  25                  30

Asn Trp Lys Thr Gln His Lys Leu Lys Arg Ala Leu Met Phe Leu Ile
        35                  40                  45

Val Lys Lys Leu
    50
```

<210> SEQ ID NO 287
<211> LENGTH: 12
<212> TYPE: PRT
<213> ORGANISM: Homo sapiens

<400> SEQUENCE: 287

Pro Ser Ile Thr Leu Gln Gln Met Leu Ala Pro Ser
1               5                   10

<210> SEQ ID NO 288
<211> LENGTH: 11
<212> TYPE: PRT
<213> ORGANISM: Homo sapiens

<400> SEQUENCE: 288

Ser Ile Thr Leu Gln Gln Met Leu Ala Pro Ser
1               5                   10

<210> SEQ ID NO 289
<211> LENGTH: 60
<212> TYPE: PRT
<213> ORGANISM: Homo sapiens

<400> SEQUENCE: 289

Thr Ser Cys Asn Glu Met Asn Pro Pro Phe His His Ile Ala Thr Asp
1               5                   10                  15

Val Gly Pro Phe Val Arg Ile Gly Phe Leu Lys Ile Lys Gly Lys Ile
            20                  25                  30

Lys Gly Lys Ser Leu Arg Lys Pro Asn Trp Lys Thr Gln His Lys Leu
        35                  40                  45

Lys Arg Ala Leu Met Phe Leu Ile Val Lys Lys Leu
    50                  55                  60

<210> SEQ ID NO 290
<211> LENGTH: 61
<212> TYPE: PRT
<213> ORGANISM: Homo sapiens

<400> SEQUENCE: 290

Thr Ser Cys Asn Glu Met Asn Pro Pro Phe His His Ile Ala Thr
1               5                   10                  15

Asp Val Gly Pro Phe Val Arg Ile Gly Phe Leu Lys Ile Lys Gly Lys
            20                  25                  30

Ile Lys Gly Lys Ser Leu Arg Lys Pro Asn Trp Lys Thr Gln His Lys
        35                  40                  45

Leu Lys Arg Ala Leu Met Phe Leu Ile Val Lys Lys Leu
    50                  55                  60

<210> SEQ ID NO 291
<211> LENGTH: 20
<212> TYPE: PRT
<213> ORGANISM: Homo sapiens

<400> SEQUENCE: 291

Thr Ser Cys Asn Glu Met Asn Pro Pro Ser Ile Thr Leu Gln Gln Met
1               5                   10                  15

Leu Ala Pro Ser
            20

```
<210> SEQ ID NO 292
<211> LENGTH: 21
<212> TYPE: PRT
<213> ORGANISM: Homo sapiens

<400> SEQUENCE: 292

Thr Ser Cys Asn Glu Met Asn Pro Pro Ser Ile Thr Leu Gln Gln
1               5                   10                  15

Met Leu Ala Pro Ser
            20

<210> SEQ ID NO 293
<211> LENGTH: 10
<212> TYPE: PRT
<213> ORGANISM: Homo sapiens

<400> SEQUENCE: 293

Leu Glu Met Ile Leu Phe Leu Met Thr Phe
1               5                   10

<210> SEQ ID NO 294
<211> LENGTH: 18
<212> TYPE: PRT
<213> ORGANISM: Homo sapiens

<400> SEQUENCE: 294

His Pro Cys Ile Thr Lys Thr Phe Leu Glu Met Ile Leu Phe Leu Met
1               5                   10                  15

Thr Phe

<210> SEQ ID NO 295
<211> LENGTH: 19
<212> TYPE: PRT
<213> ORGANISM: Homo sapiens

<400> SEQUENCE: 295

His Pro Cys Ile Thr Lys Thr Phe Phe Leu Glu Met Ile Leu Phe Leu
1               5                   10                  15

Met Thr Phe

<210> SEQ ID NO 296
<211> LENGTH: 11
<212> TYPE: PRT
<213> ORGANISM: Homo sapiens

<400> SEQUENCE: 296

His Pro Cys Ile Thr Lys Thr Phe Phe Trp Arg
1               5                   10

<210> SEQ ID NO 297
<211> LENGTH: 10
<212> TYPE: PRT
<213> ORGANISM: Homo sapiens

<400> SEQUENCE: 297

His Pro Cys Ile Thr Lys Thr Phe Trp Arg
1               5                   10

<210> SEQ ID NO 298
<211> LENGTH: 22
<212> TYPE: PRT
<213> ORGANISM: Homo sapiens
```

```
<400> SEQUENCE: 298

Leu Met Phe Glu His Ser Gln Met Arg Leu Asn Ser Lys Asn Ala His
1               5                   10                  15

Leu Pro Ile Ile Ser Phe
            20

<210> SEQ ID NO 299
<211> LENGTH: 30
<212> TYPE: PRT
<213> ORGANISM: Homo sapiens

<400> SEQUENCE: 299

Glu Tyr Gly Ser Ile Ile Ala Phe Leu Met Phe Glu His Ser Gln Met
1               5                   10                  15

Arg Leu Asn Ser Lys Asn Ala His Leu Pro Ile Ile Ser Phe
            20                  25                  30

<210> SEQ ID NO 300
<211> LENGTH: 31
<212> TYPE: PRT
<213> ORGANISM: Homo sapiens

<400> SEQUENCE: 300

Glu Tyr Gly Ser Ile Ile Ala Phe Phe Leu Met Phe Glu His Ser Gln
1               5                   10                  15

Met Arg Leu Asn Ser Lys Asn Ala His Leu Pro Ile Ile Ser Phe
            20                  25                  30

<210> SEQ ID NO 301
<211> LENGTH: 15
<212> TYPE: PRT
<213> ORGANISM: Homo sapiens

<400> SEQUENCE: 301

His Leu Asn Lys Gly Arg Arg Leu Gly Asp Lys Ile Arg Ala Thr
1               5                   10                  15

<210> SEQ ID NO 302
<211> LENGTH: 16
<212> TYPE: PRT
<213> ORGANISM: Homo sapiens

<400> SEQUENCE: 302

Phe His Leu Asn Lys Gly Arg Arg Leu Gly Asp Lys Ile Arg Ala Thr
1               5                   10                  15

<210> SEQ ID NO 303
<211> LENGTH: 23
<212> TYPE: PRT
<213> ORGANISM: Homo sapiens

<400> SEQUENCE: 303

Val Thr Ser Gly Thr Pro Phe Phe His Leu Asn Lys Gly Arg Arg Leu
1               5                   10                  15

Gly Asp Lys Ile Arg Ala Thr
            20

<210> SEQ ID NO 304
<211> LENGTH: 24
<212> TYPE: PRT
<213> ORGANISM: Homo sapiens
```

```
<400> SEQUENCE: 304

Val Thr Ser Gly Thr Pro Phe Phe His Leu Asn Lys Gly Arg Arg
1               5                   10                  15

Leu Gly Asp Lys Ile Arg Ala Thr
            20

<210> SEQ ID NO 305
<211> LENGTH: 10
<212> TYPE: PRT
<213> ORGANISM: Homo sapiens

<400> SEQUENCE: 305

Val Thr Ser Gly Thr Pro Phe Phe Phe Ile
1               5                   10

<210> SEQ ID NO 306
<211> LENGTH: 9
<212> TYPE: PRT
<213> ORGANISM: Homo sapiens

<400> SEQUENCE: 306

Val Thr Ser Gly Thr Pro Phe Phe Ile
1               5

<210> SEQ ID NO 307
<211> LENGTH: 10
<212> TYPE: PRT
<213> ORGANISM: Homo sapiens

<400> SEQUENCE: 307

Cys Glu Ile Glu Arg Ile His Phe Phe Phe
1               5                   10

<210> SEQ ID NO 308
<211> LENGTH: 11
<212> TYPE: PRT
<213> ORGANISM: Homo sapiens

<400> SEQUENCE: 308

Cys Glu Ile Glu Arg Ile His Phe Phe Ser Lys
1               5                   10

<210> SEQ ID NO 309
<211> LENGTH: 10
<212> TYPE: PRT
<213> ORGANISM: Homo sapiens

<400> SEQUENCE: 309

Cys Glu Ile Glu Arg Ile His Phe Ser Lys
1               5                   10

<210> SEQ ID NO 310
<211> LENGTH: 8
<212> TYPE: PRT
<213> ORGANISM: Homo sapiens

<400> SEQUENCE: 310

Phe Arg Tyr Ile Ser Lys Ser Ile
1               5

<210> SEQ ID NO 311
<211> LENGTH: 7
<212> TYPE: PRT
<213> ORGANISM: Homo sapiens
```

<400> SEQUENCE: 311

Arg Tyr Ile Ser Lys Ser Ile
1               5

<210> SEQ ID NO 312
<211> LENGTH: 16
<212> TYPE: PRT
<213> ORGANISM: Homo sapiens

<400> SEQUENCE: 312

Phe Lys Lys Tyr Glu Pro Ile Phe Phe Arg Tyr Ile Ser Lys Ser Ile
1               5                  10                  15

<210> SEQ ID NO 313
<211> LENGTH: 15
<212> TYPE: PRT
<213> ORGANISM: Homo sapiens

<400> SEQUENCE: 313

Phe Lys Lys Tyr Glu Pro Ile Phe Arg Tyr Ile Ser Lys Ser Ile
1               5                  10                  15

<210> SEQ ID NO 314
<211> LENGTH: 56
<212> TYPE: PRT
<213> ORGANISM: Homo sapiens

<400> SEQUENCE: 314

Phe Pro Asp Ser Asp Gln Pro Gly Pro Leu Tyr Pro Leu Asp Pro Ser
1               5                  10                  15

Cys Leu Ile Ser Ser Ala Ser Asn Pro Gln Glu Leu Ser Asp Cys His
            20                  25                  30

Tyr Ile His Leu Ala Phe Gly Phe Ser Asn Trp Arg Ser Cys Pro Val
        35                  40                  45

Leu Pro Gly His Cys Gly Val Gln
    50                  55

<210> SEQ ID NO 315
<211> LENGTH: 55
<212> TYPE: PRT
<213> ORGANISM: Homo sapiens

<400> SEQUENCE: 315

Pro Asp Ser Asp Gln Pro Gly Pro Leu Tyr Pro Leu Asp Pro Ser Cys
1               5                  10                  15

Leu Ile Ser Ser Ala Ser Asn Pro Gln Glu Leu Ser Asp Cys His Tyr
            20                  25                  30

Ile His Leu Ala Phe Gly Phe Ser Asn Trp Arg Ser Cys Pro Val Leu
        35                  40                  45

Pro Gly His Cys Gly Val Gln
    50                  55

<210> SEQ ID NO 316
<211> LENGTH: 9
<212> TYPE: PRT
<213> ORGANISM: Homo sapiens

<400> SEQUENCE: 316

Leu Asn Met Phe Ala Ser Val Phe Ser
1               5

```
<210> SEQ ID NO 317
<211> LENGTH: 10
<212> TYPE: PRT
<213> ORGANISM: Homo sapiens

<400> SEQUENCE: 317

Leu Asn Met Phe Ala Ser Val Phe Phe Ser
1               5                   10

<210> SEQ ID NO 318
<211> LENGTH: 64
<212> TYPE: PRT
<213> ORGANISM: Homo sapiens

<400> SEQUENCE: 318

Leu Asn Met Phe Ala Ser Val Phe Phe Pro Asp Ser Asp Gln Pro Gly
1               5                   10                  15

Pro Leu Tyr Pro Leu Asp Pro Ser Cys Leu Ile Ser Ser Ala Ser Asn
            20                  25                  30

Pro Gln Glu Leu Ser Asp Cys His Tyr Ile His Leu Ala Phe Gly Phe
        35                  40                  45

Ser Asn Trp Arg Ser Cys Pro Val Leu Pro Gly His Cys Gly Val Gln
    50                  55                  60

<210> SEQ ID NO 319
<211> LENGTH: 63
<212> TYPE: PRT
<213> ORGANISM: Homo sapiens

<400> SEQUENCE: 319

Leu Asn Met Phe Ala Ser Val Phe Pro Asp Ser Asp Gln Pro Gly Pro
1               5                   10                  15

Leu Tyr Pro Leu Asp Pro Ser Cys Leu Ile Ser Ser Ala Ser Asn Pro
            20                  25                  30

Gln Glu Leu Ser Asp Cys His Tyr Ile His Leu Ala Phe Gly Phe Ser
        35                  40                  45

Asn Trp Arg Ser Cys Pro Val Leu Pro Gly His Cys Gly Val Gln
    50                  55                  60

<210> SEQ ID NO 320
<211> LENGTH: 63
<212> TYPE: PRT
<213> ORGANISM: Homo sapiens

<400> SEQUENCE: 320

Ala Met Glu Glu Thr Val Val Ala Val Ala Thr Val Glu Thr Glu
1               5                   10                  15

Val Glu Ala Met Glu Glu Thr Gly Val Val Ala Ala Met Glu Glu Thr
            20                  25                  30

Glu Val Gly Ala Thr Glu Glu Thr Glu Val Ala Met Glu Ala Lys Trp
        35                  40                  45

Glu Glu Glu Thr Thr Thr Glu Met Ile Ser Ala Thr Asp His Thr
    50                  55                  60

<210> SEQ ID NO 321
<211> LENGTH: 55
<212> TYPE: PRT
<213> ORGANISM: Homo sapiens
```

```
<400> SEQUENCE: 321

Leu Trp Val Arg Pro Trp Leu Trp Glu Trp Leu Arg Trp Arg Pro Lys
1               5                   10                  15

Trp Arg Leu Trp Arg Arg Gln Glu Trp Trp Arg Leu Trp Arg Arg Pro
            20                  25                  30

Arg Trp Gly Leu Arg Arg Pro Arg Trp Leu Trp Arg Glu Asn Gly
        35                  40                  45

Arg Lys Lys Arg Leu Gln Lys
    50              55

<210> SEQ ID NO 322
<211> LENGTH: 71
<212> TYPE: PRT
<213> ORGANISM: Homo sapiens

<400> SEQUENCE: 322

Tyr Gly Gly Asp Arg Ser Arg Gly Ala Met Glu Glu Thr Val Val Val
1               5                   10                  15

Ala Val Ala Thr Val Glu Thr Glu Val Glu Ala Met Glu Glu Thr Gly
            20                  25                  30

Val Val Ala Ala Met Glu Glu Thr Glu Val Gly Ala Thr Glu Glu Thr
        35                  40                  45

Glu Val Ala Met Glu Ala Lys Trp Glu Glu Glu Thr Thr Thr Glu Met
    50                  55                  60

Ile Ser Ala Thr Asp His Thr
65                  70

<210> SEQ ID NO 323
<211> LENGTH: 72
<212> TYPE: PRT
<213> ORGANISM: Homo sapiens

<400> SEQUENCE: 323

Tyr Gly Gly Asp Arg Ser Arg Gly Gly Ala Met Glu Glu Thr Val Val
1               5                   10                  15

Val Ala Val Ala Thr Val Glu Thr Glu Val Glu Ala Met Glu Glu Thr
            20                  25                  30

Gly Val Val Ala Ala Met Glu Glu Thr Glu Val Gly Ala Thr Glu Glu
        35                  40                  45

Thr Glu Val Ala Met Glu Ala Lys Trp Glu Glu Glu Thr Thr Thr Glu
    50                  55                  60

Met Ile Ser Ala Thr Asp His Thr
65                  70

<210> SEQ ID NO 324
<211> LENGTH: 64
<212> TYPE: PRT
<213> ORGANISM: Homo sapiens

<400> SEQUENCE: 324

Tyr Gly Gly Asp Arg Ser Arg Gly Gly Leu Trp Val Arg Pro Trp Leu
1               5                   10                  15

Trp Glu Trp Leu Arg Trp Glu Pro Lys Trp Arg Leu Trp Arg Arg Gln
            20                  25                  30

Glu Trp Trp Arg Leu Trp Arg Arg Pro Arg Trp Gly Leu Arg Arg Arg
        35                  40                  45

Pro Arg Trp Leu Trp Arg Glu Asn Gly Arg Lys Lys Arg Leu Gln Lys
    50                  55                  60
```

-continued

<210> SEQ ID NO 325
<211> LENGTH: 63
<212> TYPE: PRT
<213> ORGANISM: Homo sapiens

<400> SEQUENCE: 325

Tyr Gly Gly Asp Arg Ser Arg Gly Leu Trp Val Arg Pro Trp Leu Trp
1               5                   10                  15

Glu Trp Leu Arg Trp Glu Pro Lys Trp Arg Leu Trp Arg Arg Gln Glu
            20                  25                  30

Trp Trp Arg Leu Trp Arg Arg Pro Arg Trp Gly Leu Arg Arg Arg Pro
        35                  40                  45

Arg Trp Leu Trp Arg Glu Asn Gly Arg Lys Lys Arg Leu Gln Lys
    50                  55                  60

<210> SEQ ID NO 326
<211> LENGTH: 9
<212> TYPE: PRT
<213> ORGANISM: Homo sapiens

<400> SEQUENCE: 326

Glu Phe Gly Gly Gly Arg Arg Gln Lys
1               5

<210> SEQ ID NO 327
<211> LENGTH: 8
<212> TYPE: PRT
<213> ORGANISM: Homo sapiens

<400> SEQUENCE: 327

Glu Phe Gly Gly Arg Arg Gln Lys
1               5

<210> SEQ ID NO 328
<211> LENGTH: 15
<212> TYPE: PRT
<213> ORGANISM: Homo sapiens

<400> SEQUENCE: 328

Arg Arg Ala Lys Gly Gly Gly Ala Gly Ala Ser Asn Pro Arg Gln
1               5                   10                  15

<210> SEQ ID NO 329
<211> LENGTH: 16
<212> TYPE: PRT
<213> ORGANISM: Homo sapiens

<400> SEQUENCE: 329

Gly Arg Arg Ala Lys Gly Gly Gly Ala Gly Ala Ser Asn Pro Arg Gln
1               5                   10                  15

<210> SEQ ID NO 330
<211> LENGTH: 21
<212> TYPE: PRT
<213> ORGANISM: Homo sapiens

<400> SEQUENCE: 330

Asp Val Gly Leu Arg Glu Gly Ala Leu Glu Leu Pro Thr Arg Gly Asn
1               5                   10                  15

Lys Arg Asn Val Ala
            20

```
<210> SEQ ID NO 331
<211> LENGTH: 24
<212> TYPE: PRT
<213> ORGANISM: Homo sapiens

<400> SEQUENCE: 331

Met Arg Gly Gly Gly Val Gly Gly Arg Arg Ala Lys Gly Gly
1               5                   10                  15

Ala Gly Ala Ser Asn Pro Arg Gln
            20

<210> SEQ ID NO 332
<211> LENGTH: 25
<212> TYPE: PRT
<213> ORGANISM: Homo sapiens

<400> SEQUENCE: 332

Met Arg Gly Gly Gly Val Gly Gly Arg Arg Ala Lys Gly Gly
1               5                   10                  15

Gly Ala Gly Ala Ser Asn Pro Arg Gln
            20                  25

<210> SEQ ID NO 333
<211> LENGTH: 30
<212> TYPE: PRT
<213> ORGANISM: Homo sapiens

<400> SEQUENCE: 333

Met Arg Gly Gly Gly Gly Val Gly Gly Asp Val Gly Leu Arg Glu Gly
1               5                   10                  15

Ala Leu Glu Leu Pro Thr Arg Gly Asn Lys Arg Asn Val Ala
            20                  25                  30

<210> SEQ ID NO 334
<211> LENGTH: 29
<212> TYPE: PRT
<213> ORGANISM: Homo sapiens

<400> SEQUENCE: 334

Met Arg Gly Gly Gly Gly Val Gly Asp Val Gly Leu Arg Glu Gly Ala
1               5                   10                  15

Leu Glu Leu Pro Thr Arg Gly Asn Lys Arg Asn Val Ala
            20                  25

<210> SEQ ID NO 335
<211> LENGTH: 25
<212> TYPE: PRT
<213> ORGANISM: Homo sapiens

<400> SEQUENCE: 335

Val Trp Gln Leu Ala Gly Pro Met Leu Ala Gly Trp Arg Ser Leu Gly
1               5                   10                  15

Ser Trp Phe Cys Arg Met Tyr Gly Ile
            20                  25

<210> SEQ ID NO 336
<211> LENGTH: 46
<212> TYPE: PRT
<213> ORGANISM: Homo sapiens
```

```
<400> SEQUENCE: 336

Cys Gly Ser Trp Pro Ala Leu Cys Trp Arg Ala Gly Gly Val Trp Ala
1               5                   10                  15

Val Gly Ser Ala Gly Cys Met Glu Tyr Asp Pro Glu Ala Leu Pro Ala
            20                  25                  30

Ala Trp Gly Pro Ala Ala Ala Thr Val His Pro Arg Arg
        35                  40                  45

<210> SEQ ID NO 337
<211> LENGTH: 33
<212> TYPE: PRT
<213> ORGANISM: Homo sapiens

<400> SEQUENCE: 337

Arg Arg Tyr Pro Cys Glu Trp Gly Val Trp Gln Leu Ala Gly Pro Met
1               5                   10                  15

Leu Ala Gly Trp Arg Ser Leu Gly Ser Trp Phe Cys Arg Met Tyr Gly
            20                  25                  30

Ile

<210> SEQ ID NO 338
<211> LENGTH: 34
<212> TYPE: PRT
<213> ORGANISM: Homo sapiens

<400> SEQUENCE: 338

Arg Arg Tyr Pro Cys Glu Trp Gly Gly Val Trp Gln Leu Ala Gly Pro
1               5                   10                  15

Met Leu Ala Gly Trp Arg Ser Leu Gly Ser Trp Phe Cys Arg Met Tyr
            20                  25                  30

Gly Ile

<210> SEQ ID NO 339
<211> LENGTH: 55
<212> TYPE: PRT
<213> ORGANISM: Homo sapiens

<400> SEQUENCE: 339

Arg Arg Tyr Pro Cys Glu Trp Gly Gly Cys Gly Ser Trp Pro Ala Leu
1               5                   10                  15

Cys Trp Arg Ala Gly Gly Val Trp Ala Val Gly Ser Ala Gly Cys Met
            20                  25                  30

Glu Tyr Asp Pro Glu Ala Leu Pro Ala Ala Trp Gly Pro Ala Ala Ala
            35                  40                  45

Ala Thr Val His Pro Arg Arg
        50                  55

<210> SEQ ID NO 340
<211> LENGTH: 54
<212> TYPE: PRT
<213> ORGANISM: Homo sapiens

<400> SEQUENCE: 340

Arg Arg Tyr Pro Cys Glu Trp Gly Cys Gly Ser Trp Pro Ala Leu Cys
1               5                   10                  15

Trp Arg Ala Gly Gly Val Trp Ala Val Gly Ser Ala Gly Cys Met Glu
            20                  25                  30
```

-continued

```
Tyr Asp Pro Glu Ala Leu Pro Ala Trp Gly Pro Ala Ala Ala Ala
        35                  40                  45
Thr Val His Pro Arg Arg
 50

<210> SEQ ID NO 341
<211> LENGTH: 43
<212> TYPE: PRT
<213> ORGANISM: Homo sapiens

<400> SEQUENCE: 341

Leu Trp Leu Trp Ala Gly Trp Thr Val Trp Trp Ser Cys Gly Pro Gly
 1               5                  10                  15
Glu Lys Gly His Gly Trp Pro Ser Leu Pro Thr Met Ala Leu Leu Leu
            20                  25                  30
Leu Arg Phe Ser Cys Met Arg Val Ala Ser Tyr
        35                  40

<210> SEQ ID NO 342
<211> LENGTH: 44
<212> TYPE: PRT
<213> ORGANISM: Homo sapiens

<400> SEQUENCE: 342

Gly Leu Trp Leu Trp Ala Gly Trp Thr Val Trp Trp Ser Cys Gly Pro
 1               5                  10                  15
Gly Glu Lys Gly His Gly Trp Pro Ser Leu Pro Thr Met Ala Leu Leu
            20                  25                  30
Leu Leu Arg Phe Ser Cys Met Arg Val Ala Ser Tyr
        35                  40

<210> SEQ ID NO 343
<211> LENGTH: 84
<212> TYPE: PRT
<213> ORGANISM: Homo sapiens

<400> SEQUENCE: 343

Gly Cys Gly Cys Gly Pro Ala Gly Gln Tyr Gly Gly Ala Val Gly Leu
 1               5                  10                  15
Ala Arg Arg Gly Thr Ala Gly Cys Leu Pro Cys Pro Pro Trp Leu Cys
            20                  25                  30
Cys Cys Cys Ala Phe Pro Ala Cys Gly Leu Pro Gly Thr Asp Gly Trp
        35                  40                  45
Arg Gly Trp Gln Gly Ser Gly Cys Val Arg Val Ser Gly Ser Ala Pro
 50                  55                  60
Trp Ala Pro Gly Phe Pro Phe Ser Pro Pro Cys Pro Leu Cys Gly Thr
65                  70                  75                  80
Gln Pro Arg Trp

<210> SEQ ID NO 344
<211> LENGTH: 83
<212> TYPE: PRT
<213> ORGANISM: Homo sapiens

<400> SEQUENCE: 344

Cys Gly Cys Gly Pro Ala Gly Gln Tyr Gly Gly Ala Val Gly Leu Ala
 1               5                  10                  15
Arg Arg Gly Thr Ala Gly Cys Leu Pro Cys Pro Pro Trp Leu Cys Cys
            20                  25                  30
```

```
Cys Cys Ala Phe Pro Ala Cys Gly Leu Pro Gly Thr Asp Gly Trp Arg
        35                  40                  45

Gly Trp Gln Gly Ser Gly Cys Val Arg Val Ser Gly Ser Ala Pro Trp
    50                  55                  60

Ala Pro Gly Phe Pro Phe Ser Pro Pro Cys Pro Leu Cys Gly Thr Gln
65                  70                  75                  80

Pro Arg Trp

<210> SEQ ID NO 345
<211> LENGTH: 51
<212> TYPE: PRT
<213> ORGANISM: Homo sapiens

<400> SEQUENCE: 345

Leu Ala Phe Asn Val Pro Gly Gly Leu Trp Leu Trp Ala Gly Trp Thr
1               5                   10                  15

Val Trp Trp Ser Cys Gly Pro Gly Glu Lys Gly His Gly Trp Pro Ser
            20                  25                  30

Leu Pro Thr Met Ala Leu Leu Leu Arg Phe Ser Cys Met Arg Val
        35                  40                  45

Ala Ser Tyr
    50

<210> SEQ ID NO 346
<211> LENGTH: 52
<212> TYPE: PRT
<213> ORGANISM: Homo sapiens

<400> SEQUENCE: 346

Leu Ala Phe Asn Val Pro Gly Gly Gly Leu Trp Leu Trp Ala Gly Trp
1               5                   10                  15

Thr Val Trp Trp Ser Cys Gly Pro Gly Glu Lys Gly His Gly Trp Pro
            20                  25                  30

Ser Leu Pro Thr Met Ala Leu Leu Leu Arg Phe Ser Cys Met Arg
        35                  40                  45

Val Ala Ser Tyr
    50

<210> SEQ ID NO 347
<211> LENGTH: 92
<212> TYPE: PRT
<213> ORGANISM: Homo sapiens

<400> SEQUENCE: 347

Leu Ala Phe Asn Val Pro Gly Gly Gly Cys Gly Cys Gly Pro Ala Gly
1               5                   10                  15

Gln Tyr Gly Gly Ala Val Gly Leu Ala Arg Arg Gly Thr Ala Gly Cys
            20                  25                  30

Leu Pro Cys Pro Pro Trp Leu Cys Cys Cys Ala Phe Pro Ala Cys
        35                  40                  45

Gly Leu Pro Gly Thr Asp Gly Trp Arg Gly Trp Gln Gly Ser Gly Cys
    50                  55                  60

Val Arg Val Ser Gly Ser Ala Pro Trp Ala Pro Gly Phe Pro Phe Ser
65                  70                  75                  80

Pro Pro Cys Pro Leu Cys Gly Thr Gln Pro Arg Trp
            85                  90
```

-continued

<210> SEQ ID NO 348
<211> LENGTH: 91
<212> TYPE: PRT
<213> ORGANISM: Homo sapiens

<400> SEQUENCE: 348

Leu Ala Phe Asn Val Pro Gly Gly Cys Gly Cys Gly Pro Ala Gly Gln
1               5                   10                  15

Tyr Gly Gly Ala Val Gly Leu Ala Arg Arg Gly Thr Ala Gly Cys Leu
            20                  25                  30

Pro Cys Pro Pro Trp Leu Cys Cys Cys Ala Phe Pro Ala Cys Gly
        35                  40                  45

Leu Pro Gly Thr Asp Gly Trp Arg Gly Trp Gln Gly Ser Gly Cys Val
    50                  55                  60

Arg Val Ser Gly Ser Ala Pro Trp Ala Pro Gly Phe Pro Phe Ser Pro
65                  70                  75                  80

Pro Cys Pro Leu Cys Gly Thr Gln Pro Arg Trp
                85                  90

<210> SEQ ID NO 349
<211> LENGTH: 17
<212> TYPE: PRT
<213> ORGANISM: Homo sapiens

<400> SEQUENCE: 349

Pro Pro Met Pro Met Pro Gly Gln Arg Glu Ala Pro Gly Arg Gln Glu
1               5                   10                  15

Ala

<210> SEQ ID NO 350
<211> LENGTH: 18
<212> TYPE: PRT
<213> ORGANISM: Homo sapiens

<400> SEQUENCE: 350

Gly Pro Pro Met Pro Met Pro Gly Gln Arg Glu Ala Pro Gly Arg Gln
1               5                   10                  15

Glu Ala

<210> SEQ ID NO 351
<211> LENGTH: 24
<212> TYPE: PRT
<213> ORGANISM: Homo sapiens

<400> SEQUENCE: 351

Gly His Gln Cys Gln Cys Gln Gly Lys Gly Arg His Arg Ala Asp Arg
1               5                   10                  15

Arg Pro Asp Thr Ala Gln Glu Glu
            20

<210> SEQ ID NO 352
<211> LENGTH: 23
<212> TYPE: PRT
<213> ORGANISM: Homo sapiens

<400> SEQUENCE: 352

His Gln Cys Gln Cys Gln Gly Lys Gly Arg His Arg Ala Asp Arg Arg
1               5                   10                  15

Pro Asp Thr Ala Gln Glu Glu
            20

```
<210> SEQ ID NO 353
<211> LENGTH: 25
<212> TYPE: PRT
<213> ORGANISM: Homo sapiens

<400> SEQUENCE: 353

Gly Gly His Ser Tyr Gly Gly Gly Pro Pro Met Pro Met Pro Gly Gln
1               5                   10                  15

Arg Glu Ala Pro Gly Arg Gln Glu Ala
            20                  25

<210> SEQ ID NO 354
<211> LENGTH: 26
<212> TYPE: PRT
<213> ORGANISM: Homo sapiens

<400> SEQUENCE: 354

Gly Gly His Ser Tyr Gly Gly Gly Gly Pro Pro Met Pro Met Pro Gly
1               5                   10                  15

Gln Arg Glu Ala Pro Gly Arg Gln Glu Ala
            20                  25

<210> SEQ ID NO 355
<211> LENGTH: 32
<212> TYPE: PRT
<213> ORGANISM: Homo sapiens

<400> SEQUENCE: 355

Gly Gly His Ser Tyr Gly Gly Gly Gly His Gln Cys Gln Cys Gln Gly
1               5                   10                  15

Lys Gly Arg His Arg Ala Asp Arg Arg Pro Asp Thr Ala Gln Glu Glu
            20                  25                  30

<210> SEQ ID NO 356
<211> LENGTH: 31
<212> TYPE: PRT
<213> ORGANISM: Homo sapiens

<400> SEQUENCE: 356

Gly Gly His Ser Tyr Gly Gly Gly His Gln Cys Gln Cys Gln Gly Lys
1               5                   10                  15

Gly Arg His Arg Ala Asp Arg Arg Pro Asp Thr Ala Gln Glu Glu
            20                  25                  30

<210> SEQ ID NO 357
<211> LENGTH: 10
<212> TYPE: PRT
<213> ORGANISM: Homo sapiens

<400> SEQUENCE: 357

Ala Pro Cys Pro Gln Ser Ser Gly Gly Gly
1               5                   10

<210> SEQ ID NO 358
<211> LENGTH: 17
<212> TYPE: PRT
<213> ORGANISM: Homo sapiens

<400> SEQUENCE: 358

Leu Pro Ala Pro Ser Gln Ala Ala Ala Asp Glu Leu Asp Arg Arg Pro
1               5                   10                  15

Gly
```

```
<210> SEQ ID NO 359
<211> LENGTH: 18
<212> TYPE: PRT
<213> ORGANISM: Homo sapiens

<400> SEQUENCE: 359

Thr Lys Val Arg Leu Ile Arg Gly Ala Pro Cys Pro Gln Ser Ser Gly
1               5                   10                  15

Gly Gly

<210> SEQ ID NO 360
<211> LENGTH: 19
<212> TYPE: PRT
<213> ORGANISM: Homo sapiens

<400> SEQUENCE: 360

Thr Lys Val Arg Leu Ile Arg Gly Gly Ala Pro Cys Pro Gln Ser Ser
1               5                   10                  15

Gly Gly Gly

<210> SEQ ID NO 361
<211> LENGTH: 26
<212> TYPE: PRT
<213> ORGANISM: Homo sapiens

<400> SEQUENCE: 361

Thr Lys Val Arg Leu Ile Arg Gly Gly Leu Pro Ala Pro Ser Gln Ala
1               5                   10                  15

Ala Ala Asp Glu Leu Asp Arg Arg Pro Gly
            20                  25

<210> SEQ ID NO 362
<211> LENGTH: 25
<212> TYPE: PRT
<213> ORGANISM: Homo sapiens

<400> SEQUENCE: 362

Thr Lys Val Arg Leu Ile Arg Gly Leu Pro Ala Pro Ser Gln Ala Ala
1               5                   10                  15

Ala Asp Glu Leu Asp Arg Arg Pro Gly
            20                  25

<210> SEQ ID NO 363
<211> LENGTH: 45
<212> TYPE: PRT
<213> ORGANISM: Homo sapiens

<400> SEQUENCE: 363

Cys Ser Leu Ala Lys Asp Gly Ser Thr Glu Asp Thr Val Ser Ser Leu
1               5                   10                  15

Cys Gly Glu Glu Asp Thr Glu Asp Glu Leu Glu Ala Ala Ala Ser
            20                  25                  30

His Leu Asn Lys Asp Leu Tyr Arg Glu Leu Leu Gly Gly
            35                  40                  45

<210> SEQ ID NO 364
<211> LENGTH: 46
<212> TYPE: PRT
<213> ORGANISM: Homo sapiens
```

```
-continued

<400> SEQUENCE: 364

Gly Cys Ser Leu Ala Lys Asp Gly Ser Thr Glu Asp Thr Val Ser Ser
1               5                   10                  15

Leu Cys Gly Glu Glu Asp Thr Glu Asp Glu Glu Leu Glu Ala Ala Ala
            20                  25                  30

Ser His Leu Asn Lys Asp Leu Tyr Arg Glu Leu Leu Gly Gly
        35                  40                  45

<210> SEQ ID NO 365
<211> LENGTH: 21
<212> TYPE: PRT
<213> ORGANISM: Homo sapiens

<400> SEQUENCE: 365

Ala Ala Ala Trp Gln Lys Met Ala Pro Pro Arg Thr Pro Arg Pro Ala
1               5                   10                  15

Cys Val Ala Arg Arg
            20

<210> SEQ ID NO 366
<211> LENGTH: 54
<212> TYPE: PRT
<213> ORGANISM: Homo sapiens

<400> SEQUENCE: 366

Glu Asn Ser Arg Pro Lys Arg Gly Gly Cys Ser Leu Ala Lys Asp Gly
1               5                   10                  15

Ser Thr Glu Asp Thr Val Ser Ser Leu Cys Gly Glu Glu Asp Thr Glu
            20                  25                  30

Asp Glu Glu Leu Glu Ala Ala Ala Ser His Leu Asn Lys Asp Leu Tyr
        35                  40                  45

Arg Glu Leu Leu Gly Gly
    50

<210> SEQ ID NO 367
<211> LENGTH: 55
<212> TYPE: PRT
<213> ORGANISM: Homo sapiens

<400> SEQUENCE: 367

Glu Asn Ser Arg Pro Lys Arg Gly Gly Gly Cys Ser Leu Ala Lys Asp
1               5                   10                  15

Gly Ser Thr Glu Asp Thr Val Ser Ser Leu Cys Gly Glu Glu Asp Thr
            20                  25                  30

Glu Asp Glu Glu Leu Glu Ala Ala Ala Ser His Leu Asn Lys Asp Leu
        35                  40                  45

Tyr Arg Glu Leu Leu Gly Gly
    50                  55

<210> SEQ ID NO 368
<211> LENGTH: 30
<212> TYPE: PRT
<213> ORGANISM: Homo sapiens

<400> SEQUENCE: 368

Glu Asn Ser Arg Pro Lys Arg Gly Gly Ala Ala Ala Trp Gln Lys Met
1               5                   10                  15

Ala Pro Pro Arg Thr Pro Arg Pro Ala Cys Val Ala Arg Arg
            20                  25                  30
```

```
<210> SEQ ID NO 369
<211> LENGTH: 29
<212> TYPE: PRT
<213> ORGANISM: Homo sapiens

<400> SEQUENCE: 369

Glu Asn Ser Arg Pro Lys Arg Gly Ala Ala Trp Gln Lys Met Ala
1               5                   10                  15

Pro Pro Arg Thr Pro Arg Pro Ala Cys Val Ala Arg Arg
            20                  25

<210> SEQ ID NO 370
<211> LENGTH: 10
<212> TYPE: PRT
<213> ORGANISM: Homo sapiens

<400> SEQUENCE: 370

His Cys Val Leu Ala Ala Ser Gly Ala Ser
1               5                   10

<210> SEQ ID NO 371
<211> LENGTH: 11
<212> TYPE: PRT
<213> ORGANISM: Homo sapiens

<400> SEQUENCE: 371

Gly His Cys Val Leu Ala Ala Ser Gly Ala Ser
1               5                   10

<210> SEQ ID NO 372
<211> LENGTH: 28
<212> TYPE: PRT
<213> ORGANISM: Homo sapiens

<400> SEQUENCE: 372

Gly Thr Ala Ser Ser Arg Pro Leu Gly Leu Pro Lys Pro His Leu His
1               5                   10                  15

Arg Pro Val Pro Ile Arg His Pro Ser Cys Pro Lys
            20                  25

<210> SEQ ID NO 373
<211> LENGTH: 27
<212> TYPE: PRT
<213> ORGANISM: Homo sapiens

<400> SEQUENCE: 373

Thr Ala Ser Ser Arg Pro Leu Gly Leu Pro Lys Pro His Leu His Arg
1               5                   10                  15

Pro Val Pro Ile Arg His Pro Ser Cys Pro Lys
            20                  25

<210> SEQ ID NO 374
<211> LENGTH: 18
<212> TYPE: PRT
<213> ORGANISM: Homo sapiens

<400> SEQUENCE: 374

Ala Gly Thr Leu Gln Leu Gly Gly His Cys Val Leu Ala Ala Ser Gly
1               5                   10                  15

Ala Ser
```

<210> SEQ ID NO 375
<211> LENGTH: 19
<212> TYPE: PRT
<213> ORGANISM: Homo sapiens

<400> SEQUENCE: 375

Ala Gly Thr Leu Gln Leu Gly Gly Gly His Cys Val Leu Ala Ala Ser
1               5                   10                  15

Gly Ala Ser

<210> SEQ ID NO 376
<211> LENGTH: 35
<212> TYPE: PRT
<213> ORGANISM: Homo sapiens

<400> SEQUENCE: 376

Ala Gly Thr Leu Gln Leu Gly Gly Thr Ala Ser Ser Arg Pro Leu Gly
1               5                   10                  15

Leu Pro Lys Pro His Leu His Arg Pro Val Pro Ile Arg His Pro Ser
            20                  25                  30

Cys Pro Lys
        35

<210> SEQ ID NO 377
<211> LENGTH: 36
<212> TYPE: PRT
<213> ORGANISM: Homo sapiens

<400> SEQUENCE: 377

Ala Gly Thr Leu Gln Leu Gly Gly Gly Thr Ala Ser Ser Arg Pro Leu
1               5                   10                  15

Gly Leu Pro Lys Pro His Leu His Arg Pro Val Pro Ile Arg His Pro
            20                  25                  30

Ser Cys Pro Lys
        35

<210> SEQ ID NO 378
<211> LENGTH: 9
<212> TYPE: PRT
<213> ORGANISM: Homo sapiens

<400> SEQUENCE: 378

Arg Arg Thr Pro Ser Thr Glu Lys Arg
1               5

<210> SEQ ID NO 379
<211> LENGTH: 10
<212> TYPE: PRT
<213> ORGANISM: Homo sapiens

<400> SEQUENCE: 379

Arg Arg Thr Pro Ser Thr Glu Lys Lys Arg
1               5                   10

<210> SEQ ID NO 380
<211> LENGTH: 14
<212> TYPE: PRT
<213> ORGANISM: Homo sapiens

<400> SEQUENCE: 380

Arg Arg Thr Pro Ser Thr Glu Lys Lys Gly Arg Ser Glu Cys
1               5                   10

<210> SEQ ID NO 381
<211> LENGTH: 13
<212> TYPE: PRT
<213> ORGANISM: Homo sapiens

<400> SEQUENCE: 381

Arg Arg Thr Pro Ser Thr Glu Lys Gly Arg Ser Glu Cys
1               5                   10

<210> SEQ ID NO 382
<211> LENGTH: 46
<212> TYPE: PRT
<213> ORGANISM: Homo sapiens

<400> SEQUENCE: 382

Ser Thr Thr Lys Cys Gln Ser Gly Thr Ala Glu Thr Tyr Asn Ser Trp
1               5                   10                  15

Lys Val Lys Asn Leu Gln Leu Glu Pro Arg Arg Val Thr Ser Gln Met
            20                  25                  30

Asn Arg Gln Val Lys Asp Met Thr Ala Ile Leu Ser Gln Ser
        35                  40                  45

<210> SEQ ID NO 383
<211> LENGTH: 17
<212> TYPE: PRT
<213> ORGANISM: Homo sapiens

<400> SEQUENCE: 383

Val Gln Pro Asn Ala Ser Gln Ala Gln Lys Pro Thr Thr His Gly
1               5                   10                  15

Arg

<210> SEQ ID NO 384
<211> LENGTH: 54
<212> TYPE: PRT
<213> ORGANISM: Homo sapiens

<400> SEQUENCE: 384

Ser Ser Glu Glu Ile Lys Lys Lys Ser Thr Thr Lys Cys Gln Ser Gly
1               5                   10                  15

Thr Ala Glu Thr Tyr Asn Ser Trp Lys Val Lys Asn Leu Gln Leu Glu
            20                  25                  30

Pro Arg Arg Val Thr Ser Gln Met Asn Arg Gln Val Lys Asp Met Thr
        35                  40                  45

Ala Ile Leu Ser Gln Ser
    50

<210> SEQ ID NO 385
<211> LENGTH: 55
<212> TYPE: PRT
<213> ORGANISM: Homo sapiens

<400> SEQUENCE: 385

Ser Ser Glu Glu Ile Lys Lys Lys Ser Thr Thr Lys Cys Gln Ser
1               5                   10                  15

Gly Thr Ala Glu Thr Tyr Asn Ser Trp Lys Val Lys Asn Leu Gln Leu
            20                  25                  30

Glu Pro Arg Arg Val Thr Ser Gln Met Asn Arg Gln Val Lys Asp Met
        35                  40                  45

Thr Ala Ile Leu Ser Gln Ser
    50              55

<210> SEQ ID NO 386
<211> LENGTH: 26
<212> TYPE: PRT
<213> ORGANISM: Homo sapiens

<400> SEQUENCE: 386

Ser Ser Glu Glu Ile Lys Lys Lys Val Gln Pro Asn Ala Ser Gln
1               5                   10                  15

Ala Gln Gln Lys Pro Thr Thr His Gly Arg
            20                  25

<210> SEQ ID NO 387
<211> LENGTH: 25
<212> TYPE: PRT
<213> ORGANISM: Homo sapiens

<400> SEQUENCE: 387

Ser Ser Glu Glu Ile Lys Lys Val Gln Pro Asn Ala Ser Gln Ala
1               5                   10                  15

Gln Gln Lys Pro Thr Thr His Gly Arg
            20                  25

<210> SEQ ID NO 388
<211> LENGTH: 9
<212> TYPE: PRT
<213> ORGANISM: Homo sapiens

<400> SEQUENCE: 388

Asn Arg Gly Trp Val Gly Ala Gly Glu
1               5

<210> SEQ ID NO 389
<211> LENGTH: 4
<212> TYPE: PRT
<213> ORGANISM: Homo sapiens

<400> SEQUENCE: 389

Ile Glu Ala Gly
1

<210> SEQ ID NO 390
<211> LENGTH: 17
<212> TYPE: PRT
<213> ORGANISM: Homo sapiens

<400> SEQUENCE: 390

Val His Asn Tyr Cys Asn Met Lys Asn Arg Gly Trp Val Gly Ala Gly
1               5                   10                  15

Glu

<210> SEQ ID NO 391
<211> LENGTH: 18
<212> TYPE: PRT
<213> ORGANISM: Homo sapiens

<400> SEQUENCE: 391

Val His Asn Tyr Cys Asn Met Lys Lys Asn Arg Gly Trp Val Gly Ala
1               5                   10                  15

Gly Glu

<210> SEQ ID NO 392
<211> LENGTH: 13
<212> TYPE: PRT
<213> ORGANISM: Homo sapiens

<400> SEQUENCE: 392

Val His Asn Tyr Cys Asn Met Lys Lys Ile Glu Ala Gly
1               5                   10

<210> SEQ ID NO 393
<211> LENGTH: 12
<212> TYPE: PRT
<213> ORGANISM: Homo sapiens

<400> SEQUENCE: 393

Val His Asn Tyr Cys Asn Met Lys Ile Glu Ala Gly
1               5                   10

<210> SEQ ID NO 394
<211> LENGTH: 25
<212> TYPE: PRT
<213> ORGANISM: Homo sapiens

<400> SEQUENCE: 394

Gln Leu Arg Cys Trp Asn Thr Trp Ala Lys Met Phe Phe Met Val Phe
1               5                   10                  15

Leu Ile Ile Trp Gln Asn Thr Met Phe
            20                  25

<210> SEQ ID NO 395
<211> LENGTH: 33
<212> TYPE: PRT
<213> ORGANISM: Homo sapiens

<400> SEQUENCE: 395

Val Lys Lys Asp Asn His Lys Lys Gln Leu Arg Cys Trp Asn Thr Trp
1               5                   10                  15

Ala Lys Met Phe Phe Met Val Phe Leu Ile Ile Trp Gln Asn Thr Met
            20                  25                  30

Phe

<210> SEQ ID NO 396
<211> LENGTH: 34
<212> TYPE: PRT
<213> ORGANISM: Homo sapiens

<400> SEQUENCE: 396

Val Lys Lys Asp Asn His Lys Lys Gln Leu Arg Cys Trp Asn Thr
1               5                   10                  15

Trp Ala Lys Met Phe Phe Met Val Phe Leu Ile Ile Trp Gln Asn Thr
            20                  25                  30

Met Phe

<210> SEQ ID NO 397
<211> LENGTH: 11
<212> TYPE: PRT
<213> ORGANISM: Homo sapiens

<400> SEQUENCE: 397

Val Lys Lys Asp Asn His Lys Lys Lys Asn Ser
1               5                   10

<210> SEQ ID NO 398
<211> LENGTH: 10
<212> TYPE: PRT
<213> ORGANISM: Homo sapiens

<400> SEQUENCE: 398

Val Lys Lys Asp Asn His Lys Lys Asn Ser
1               5                   10

<210> SEQ ID NO 399
<211> LENGTH: 35
<212> TYPE: PRT
<213> ORGANISM: Homo sapiens

<400> SEQUENCE: 399

Gly Ala Glu Glu Ser Gly Pro Phe Asn Arg Gln Val Gln Leu Lys Val
1               5                   10                  15

His Ala Ser Gly Met Gly Arg His Leu Trp Asn Cys Pro Ala Phe Trp
            20                  25                  30

Ser Glu Val
        35

<210> SEQ ID NO 400
<211> LENGTH: 10
<212> TYPE: PRT
<213> ORGANISM: Homo sapiens

<400> SEQUENCE: 400

His Pro Ser Pro Pro Glu Lys Arg Ser
1               5                   10

<210> SEQ ID NO 401
<211> LENGTH: 11
<212> TYPE: PRT
<213> ORGANISM: Homo sapiens

<400> SEQUENCE: 401

His Pro Ser Pro Pro Glu Lys Lys Arg Ser
1               5                   10

<210> SEQ ID NO 402
<211> LENGTH: 44
<212> TYPE: PRT
<213> ORGANISM: Homo sapiens

<400> SEQUENCE: 402

His Pro Ser Pro Pro Glu Lys Lys Gly Ala Glu Glu Ser Gly Pro
1               5                   10                  15

Phe Asn Arg Gln Val Gln Leu Lys Val His Ala Ser Gly Met Gly Arg
            20                  25                  30

His Leu Trp Asn Cys Pro Ala Phe Trp Ser Glu Val
            35                  40

<210> SEQ ID NO 403
<211> LENGTH: 43
<212> TYPE: PRT
<213> ORGANISM: Homo sapiens

<400> SEQUENCE: 403

His Pro Ser Pro Pro Glu Lys Gly Ala Glu Glu Ser Gly Pro Phe
1               5                   10                  15

-continued

Asn Arg Gln Val Gln Leu Lys Val His Ala Ser Gly Met Gly Arg His
            20                  25                  30
Leu Trp Asn Cys Pro Ala Phe Trp Ser Glu Val
            35                  40

<210> SEQ ID NO 404
<211> LENGTH: 39
<212> TYPE: PRT
<213> ORGANISM: Homo sapiens

<400> SEQUENCE: 404

Met Gln Val Leu Ser Lys Thr His Met Asn Leu Phe Pro Gln Val Leu
1               5                   10                  15
Leu Gln Met Phe Leu Arg Gly Leu Lys Arg Leu Leu Gln Asp Leu Glu
            20                  25                  30
Lys Ser Lys Lys Arg Lys Leu
            35

<210> SEQ ID NO 405
<211> LENGTH: 8
<212> TYPE: PRT
<213> ORGANISM: Homo sapiens

<400> SEQUENCE: 405

Arg Cys Lys Ser Ala Arg Leu Ile
1               5

<210> SEQ ID NO 406
<211> LENGTH: 48
<212> TYPE: PRT
<213> ORGANISM: Homo sapiens

<400> SEQUENCE: 406

Val Gln Thr Gln Pro Ala Ile Lys Lys Met Gln Val Leu Ser Lys Thr
1               5                   10                  15
His Met Asn Leu Phe Pro Gln Val Leu Leu Gln Met Phe Leu Arg Gly
            20                  25                  30
Leu Lys Arg Leu Leu Gln Asp Leu Glu Lys Ser Lys Lys Arg Lys Leu
            35                  40                  45

<210> SEQ ID NO 407
<211> LENGTH: 49
<212> TYPE: PRT
<213> ORGANISM: Homo sapiens

<400> SEQUENCE: 407

Val Gln Thr Gln Pro Ala Ile Lys Lys Lys Met Gln Val Leu Ser Lys
1               5                   10                  15
Thr His Met Asn Leu Phe Pro Gln Val Leu Leu Gln Met Phe Leu Arg
            20                  25                  30
Gly Leu Lys Arg Leu Leu Gln Asp Leu Glu Lys Ser Lys Lys Arg Lys
            35                  40                  45
Leu

<210> SEQ ID NO 408
<211> LENGTH: 17
<212> TYPE: PRT
<213> ORGANISM: Homo sapiens

```
<400> SEQUENCE: 408

Val Gln Thr Gln Pro Ala Ile Lys Arg Cys Lys Ser Ala Arg Leu
1               5                   10                  15

Ile

<210> SEQ ID NO 409
<211> LENGTH: 16
<212> TYPE: PRT
<213> ORGANISM: Homo sapiens

<400> SEQUENCE: 409

Val Gln Thr Gln Pro Ala Ile Lys Arg Cys Lys Ser Ala Arg Leu Ile
1               5                   10                  15

<210> SEQ ID NO 410
<211> LENGTH: 11
<212> TYPE: PRT
<213> ORGANISM: Homo sapiens

<400> SEQUENCE: 410

Ala Arg Ser Gly Lys Lys Gln Lys Arg Lys Leu
1               5                   10

<210> SEQ ID NO 411
<211> LENGTH: 12
<212> TYPE: PRT
<213> ORGANISM: Homo sapiens

<400> SEQUENCE: 411

Ala Arg Ser Gly Lys Lys Gln Lys Lys Arg Lys Leu
1               5                   10

<210> SEQ ID NO 412
<211> LENGTH: 13
<212> TYPE: PRT
<213> ORGANISM: Homo sapiens

<400> SEQUENCE: 412

Ala Arg Ser Gly Lys Lys Gln Lys Lys Glu Asn Ser Phe
1               5                   10

<210> SEQ ID NO 413
<211> LENGTH: 12
<212> TYPE: PRT
<213> ORGANISM: Homo sapiens

<400> SEQUENCE: 413

Ala Arg Ser Gly Lys Lys Gln Lys Glu Asn Ser Phe
1               5                   10

<210> SEQ ID NO 414
<211> LENGTH: 14
<212> TYPE: PRT
<213> ORGANISM: Homo sapiens

<400> SEQUENCE: 414

Lys Ala Ser Ala Arg Ser Gly Lys Ser Lys Arg Lys Leu
1               5                   10

<210> SEQ ID NO 415
<211> LENGTH: 15
<212> TYPE: PRT
<213> ORGANISM: Homo sapiens
```

```
<400> SEQUENCE: 415

Lys Ala Ser Ala Arg Ser Gly Lys Lys Ser Lys Arg Lys Leu
1               5                   10                  15

<210> SEQ ID NO 416
<211> LENGTH: 16
<212> TYPE: PRT
<213> ORGANISM: Homo sapiens

<400> SEQUENCE: 416

Lys Ala Ser Ala Arg Ser Gly Lys Lys Ala Lys Lys Glu Asn Ser Phe
1               5                   10                  15

<210> SEQ ID NO 417
<211> LENGTH: 15
<212> TYPE: PRT
<213> ORGANISM: Homo sapiens

<400> SEQUENCE: 417

Lys Ala Ser Ala Arg Ser Gly Lys Ala Lys Lys Glu Asn Ser Phe
1               5                   10                  15

<210> SEQ ID NO 418
<211> LENGTH: 15
<212> TYPE: PRT
<213> ORGANISM: Homo sapiens

<400> SEQUENCE: 418

His Leu Asn Lys Gly Arg Arg Leu Gly Asp Lys Ile Arg Ala Thr
1               5                   10                  15

<210> SEQ ID NO 419
<211> LENGTH: 23
<212> TYPE: PRT
<213> ORGANISM: Homo sapiens

<400> SEQUENCE: 419

Val Thr Ser Gly Thr Pro Phe Phe His Leu Asn Lys Gly Arg Arg Leu
1               5                   10                  15

Gly Asp Lys Ile Arg Ala Thr
            20

<210> SEQ ID NO 420
<211> LENGTH: 24
<212> TYPE: PRT
<213> ORGANISM: Homo sapiens

<400> SEQUENCE: 420

Val Thr Ser Gly Thr Pro Phe Phe Phe His Leu Asn Lys Gly Arg Arg
1               5                   10                  15

Leu Gly Asp Lys Ile Arg Ala Thr
            20

<210> SEQ ID NO 421
<211> LENGTH: 10
<212> TYPE: PRT
<213> ORGANISM: Homo sapiens

<400> SEQUENCE: 421

Val Thr Ser Gly Thr Pro Phe Phe Phe Ile
1               5                   10
```

<210> SEQ ID NO 422
<211> LENGTH: 9
<212> TYPE: PRT
<213> ORGANISM: Homo sapiens

<400> SEQUENCE: 422

Val Thr Ser Gly Thr Pro Phe Phe Ile
1               5

<210> SEQ ID NO 423
<211> LENGTH: 51
<212> TYPE: PRT
<213> ORGANISM: Homo sapiens

<400> SEQUENCE: 423

Val Thr Leu Leu Tyr Val Asn Thr Val Thr Leu Ala Pro Asn Val Asn
1               5                   10                  15

Met Glu Ser Ser Arg Asn Ala His Ser Pro Ala Thr Pro Ser Ala Lys
            20                  25                  30

Arg Lys Asp Pro Asp Leu Thr Trp Gly Gly Phe Val Phe Phe Cys
        35                  40                  45

Gln Phe His
    50

<210> SEQ ID NO 424
<211> LENGTH: 60
<212> TYPE: PRT
<213> ORGANISM: Homo sapiens

<400> SEQUENCE: 424

Lys Cys Arg Cys Lys Pro Asn Phe Phe Val Thr Leu Leu Tyr Val Asn
1               5                   10                  15

Thr Val Thr Leu Ala Pro Asn Val Asn Met Glu Ser Ser Arg Asn Ala
            20                  25                  30

His Ser Pro Ala Thr Pro Ser Ala Lys Arg Lys Asp Pro Asp Leu Thr
        35                  40                  45

Trp Gly Gly Phe Val Phe Phe Cys Gln Phe His
    50                  55                  60

<210> SEQ ID NO 425
<211> LENGTH: 61
<212> TYPE: PRT
<213> ORGANISM: Homo sapiens

<400> SEQUENCE: 425

Lys Cys Arg Cys Lys Pro Asn Phe Phe Val Thr Leu Leu Tyr Val
1               5                   10                  15

Asn Thr Val Thr Leu Ala Pro Asn Val Asn Met Glu Ser Ser Arg Asn
            20                  25                  30

Ala His Ser Pro Ala Thr Pro Ser Ala Lys Arg Lys Asp Pro Asp Leu
        35                  40                  45

Thr Trp Gly Gly Phe Val Phe Phe Cys Gln Phe His
    50                  55                  60

<210> SEQ ID NO 426
<211> LENGTH: 10
<212> TYPE: PRT
<213> ORGANISM: Homo sapiens

```
<400> SEQUENCE: 426

Lys Cys Arg Cys Lys Pro Asn Phe Phe Leu
1               5                   10

<210> SEQ ID NO 427
<211> LENGTH: 9
<212> TYPE: PRT
<213> ORGANISM: Homo sapiens

<400> SEQUENCE: 427

Lys Cys Arg Cys Lys Pro Asn Phe Leu
1               5

<210> SEQ ID NO 428
<211> LENGTH: 9
<212> TYPE: PRT
<213> ORGANISM: Homo sapiens

<400> SEQUENCE: 428

Ser Leu Val Arg Leu Ser Ser Cys Val
1               5

<210> SEQ ID NO 429
<211> LENGTH: 14
<212> TYPE: PRT
<213> ORGANISM: Homo sapiens

<400> SEQUENCE: 429

Leu Val Lys Lys Leu Lys Glu Lys Lys Met Asn Trp Ile Leu
1               5                   10

<210> SEQ ID NO 430
<211> LENGTH: 15
<212> TYPE: PRT
<213> ORGANISM: Homo sapiens

<400> SEQUENCE: 430

Leu Val Lys Lys Leu Lys Glu Lys Lys Met Asn Trp Ile Leu
1               5                   10                  15

<210> SEQ ID NO 431
<211> LENGTH: 10
<212> TYPE: PRT
<213> ORGANISM: Homo sapiens

<400> SEQUENCE: 431

Leu Val Lys Lys Leu Lys Glu Lys Lys Arg
1               5                   10

<210> SEQ ID NO 432
<211> LENGTH: 9
<212> TYPE: PRT
<213> ORGANISM: Homo sapiens

<400> SEQUENCE: 432

Leu Val Lys Lys Leu Lys Glu Lys Arg
1               5

<210> SEQ ID NO 433
<211> LENGTH: 9
<212> TYPE: PRT
<213> ORGANISM: Homo sapiens
```

```
<400> SEQUENCE: 433

Ala Ala Ile Val Lys Asp Cys Cys Arg
1               5

<210> SEQ ID NO 434
<211> LENGTH: 11
<212> TYPE: PRT
<213> ORGANISM: Homo sapiens

<400> SEQUENCE: 434

Ser Gln Pro Ala Ser Ile Leu Gly Arg Lys Leu
1               5                   10

<210> SEQ ID NO 435
<211> LENGTH: 12
<212> TYPE: PRT
<213> ORGANISM: Homo sapiens

<400> SEQUENCE: 435

Ser Gln Pro Ala Ser Ile Leu Gly Lys Arg Lys Leu
1               5                   10

<210> SEQ ID NO 436
<211> LENGTH: 18
<212> TYPE: PRT
<213> ORGANISM: Homo sapiens

<400> SEQUENCE: 436

Ser Gln Pro Ala Ser Ile Leu Gly Lys Ala Ala Ile Val Lys Asp Cys
1               5                   10                  15

Cys Arg

<210> SEQ ID NO 437
<211> LENGTH: 17
<212> TYPE: PRT
<213> ORGANISM: Homo sapiens

<400> SEQUENCE: 437

Ser Gln Pro Ala Ser Ile Leu Gly Ala Ala Ile Val Lys Asp Cys Cys
1               5                   10                  15

Arg

<210> SEQ ID NO 438
<211> LENGTH: 18
<212> TYPE: PRT
<213> ORGANISM: Homo sapiens

<400> SEQUENCE: 438

Lys Ser Leu Val Arg Leu Ser Ser Cys Val Pro Val Ala Leu Met Ser
1               5                   10                  15

Ala Met

<210> SEQ ID NO 439
<211> LENGTH: 9
<212> TYPE: PRT
<213> ORGANISM: Homo sapiens

<400> SEQUENCE: 439

Arg Leu Ser Ser Cys Val Pro Val Ala
1               5
```

```
<210> SEQ ID NO 440
<211> LENGTH: 9
<212> TYPE: PRT
<213> ORGANISM: Homo sapiens

<400> SEQUENCE: 440

Val Arg Leu Ser Ser Cys Val Pro Val
1               5

<210> SEQ ID NO 441
<211> LENGTH: 9
<212> TYPE: PRT
<213> ORGANISM: Homo sapiens

<400> SEQUENCE: 441

Leu Val Arg Leu Ser Ser Cys Val Pro
1               5

<210> SEQ ID NO 442
<211> LENGTH: 9
<212> TYPE: PRT
<213> ORGANISM: Homo sapiens

<400> SEQUENCE: 442

Ser Cys Val Pro Val Ala Leu Met Ser
1               5

<210> SEQ ID NO 443
<211> LENGTH: 9
<212> TYPE: PRT
<213> ORGANISM: Homo sapiens

<400> SEQUENCE: 443

Ser Ser Cys Val Pro Val Ala Leu Met
1               5

<210> SEQ ID NO 444
<211> LENGTH: 9
<212> TYPE: PRT
<213> ORGANISM: Homo sapiens

<400> SEQUENCE: 444

Leu Ser Ser Cys Val Pro Val Ala Leu
1               5

<210> SEQ ID NO 445
<211> LENGTH: 9
<212> TYPE: PRT
<213> ORGANISM: Homo sapiens

<400> SEQUENCE: 445

Val Pro Val Ala Leu Met Ser Ala Met
1               5

<210> SEQ ID NO 446
<211> LENGTH: 9
<212> TYPE: PRT
<213> ORGANISM: Homo sapiens

<400> SEQUENCE: 446

Cys Val Pro Val Ala Leu Met Ser Ala
1               5
```

```
<210> SEQ ID NO 447
<211> LENGTH: 9
<212> TYPE: PRT
<213> ORGANISM: Homo sapiens

<400> SEQUENCE: 447

Lys Lys Lys Ser Leu Val Arg Leu Ser
1               5

<210> SEQ ID NO 448
<211> LENGTH: 9
<212> TYPE: PRT
<213> ORGANISM: Homo sapiens

<400> SEQUENCE: 448

Glu Lys Lys Lys Ser Leu Val Arg Leu
1               5

<210> SEQ ID NO 449
<211> LENGTH: 9
<212> TYPE: PRT
<213> ORGANISM: Homo sapiens

<400> SEQUENCE: 449

Lys Glu Lys Lys Lys Ser Leu Val Arg
1               5

<210> SEQ ID NO 450
<211> LENGTH: 9
<212> TYPE: PRT
<213> ORGANISM: Homo sapiens

<400> SEQUENCE: 450

Met Lys Glu Lys Lys Lys Ser Leu Val
1               5

<210> SEQ ID NO 451
<211> LENGTH: 9
<212> TYPE: PRT
<213> ORGANISM: Homo sapiens

<400> SEQUENCE: 451

Ile Met Lys Glu Lys Lys Lys Ser Leu
1               5

<210> SEQ ID NO 452
<211> LENGTH: 9
<212> TYPE: PRT
<213> ORGANISM: Homo sapiens

<400> SEQUENCE: 452

Lys Cys Ile Met Lys Glu Lys Lys Ala
1               5

<210> SEQ ID NO 453
<211> LENGTH: 9
<212> TYPE: PRT
<213> ORGANISM: Homo sapiens

<400> SEQUENCE: 453

Cys Ile Met Lys Glu Lys Lys Ala Trp
1               5
```

```
<210> SEQ ID NO 454
<211> LENGTH: 9
<212> TYPE: PRT
<213> ORGANISM: Homo sapiens

<400> SEQUENCE: 454

Cys Ile Met Lys Glu Lys Lys Lys Ala
1               5

<210> SEQ ID NO 455
<211> LENGTH: 9
<212> TYPE: PRT
<213> ORGANISM: Homo sapiens

<400> SEQUENCE: 455

Ile Met Lys Glu Lys Lys Lys Ala Trp
1               5

<210> SEQ ID NO 456
<211> LENGTH: 13
<212> TYPE: PRT
<213> ORGANISM: Homo sapiens

<400> SEQUENCE: 456

His Pro Ser Trp Pro Trp Thr Arg Cys Leu Arg Met Arg
1               5                   10

<210> SEQ ID NO 457
<211> LENGTH: 14
<212> TYPE: PRT
<213> ORGANISM: Homo sapiens

<400> SEQUENCE: 457

Arg His Pro Ser Trp Pro Trp Thr Arg Cys Leu Arg Met Arg
1               5                   10

<210> SEQ ID NO 458
<211> LENGTH: 16
<212> TYPE: PRT
<213> ORGANISM: Homo sapiens

<400> SEQUENCE: 458

Gly Ala Ser Gly Cys Val His Gln Glu Ala Glu Arg Val Ser Gln Ala
1               5                   10                  15

<210> SEQ ID NO 459
<211> LENGTH: 20
<212> TYPE: PRT
<213> ORGANISM: Homo sapiens

<400> SEQUENCE: 459

Asn Thr Trp Ala Lys Met Phe Phe Met Val Phe Leu Ile Ile Trp Gln
1               5                   10                  15

Asn Thr Met Phe
            20
```

The invention claimed is:

1. An isolated BAX gene frameshift-mutation peptide selected from the group consisting of Seq ID No. 1, Seq ID No. 5, and Seq ID No. 9.

2. A composition comprising a peptide according to claim 1 and a carrier or diluent therefor.

3. An isolated peptide consisting of Seq ID No. 1.

4. An isolated peptide consisting of Seq ID No. 5.

5. An isolated peptide consisting of Seq ID No. 9.

6. A composition comprising a peptide according to claim 3 and a carrier or diluent therefor.

7. A composition comprising a peptide according to claim 4 and a carrier or diluent therefor.

8. A composition comprising a peptide according to claim 5 and a carrier or diluent therefor.

9. A method of stimulating the proliferation of human T cells, comprising the steps of: i) obtaining T cells from a human cancer patient and ii) contacting the T cells obtained in step i) with a BAX gene frameshift-mutation peptide selected from the group consisting of Seq ID No. 1, Seq ID No. 5, and Seq ID No. 9, said peptide being capable of inducing T cell proliferation, either in its full length form or after processing by an antigen-presenting cell.

10. The method according to claim 9, wherein the peptide used in step ii) is Seq ID No. 1.

11. The method according to claim 9, wherein the peptide used in step ii) is Seq ID No. 5.

12. The method according to claim 9, wherein the peptide used in step ii) is Seq ID No. 9.

* * * * *

UNITED STATES PATENT AND TRADEMARK OFFICE
CERTIFICATE OF CORRECTION

PATENT NO.         : 7,192,927 B2
APPLICATION NO.    : 10/776224
DATED              : March 20, 2007
INVENTOR(S)        : Gustav Gaudernack et al.

Page 1 of 1

It is certified that error appears in the above-identified patent and that said Letters Patent is hereby corrected as shown below:

ON THE TITLE PAGE [56] REFERENCES CITED:

Other Publications, after "Rampino et al.": "BAX Gen" should read --BAX Gene-- and "Pheotype"." should read --Phenotype".--; and after "Gjertsin et al. (1997),": "CD8$^+$T-Lymphocyt s," should read --CD8$^+$T-Lymphocytes,--.

ON THE TITLE PAGE [62]:

Related U.S. Application Data, "PCT/NO92/00032" should read --PCT/NO99/00143--.

COLUMN 1:

Line 5, "PCT/NO92/00032" should read --PCT/NO99/00143--.

COLUMN 2:

Line 6, "cancer (list?)." should read --cancer.--

Signed and Sealed this

Eighteenth Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,192,927 B2 Page 1 of 11
APPLICATION NO. : 10/776224
DATED : March 20, 2007
INVENTOR(S) : Gustav Guadernack et al.

It is certified that error appears in the above-identified patent and that said Letters Patent is hereby corrected as shown below:

COLUMNS 35-40

Delete column 35, line 2, to column 40, line 64, and replace with attached page 52, line 8, to page 63, line 38, of the original specification as filed.

Signed and Sealed this

Seventh Day of September, 2010

David J. Kappos
*Director of the United States Patent and Trademark Office* result in an overlapping peptide. This has now been proven for CD4 T cells by the results in Fig. 8-11. These results have the following implication:

1) The results in Figure 8 prove that the mutated form of TGFβRII Receptor which occurs in a high proportion of cancer patients with defects in their mismatch repair machinery is a tumour specific antigen.

2) The antigen specificity of the infiltrating T cells commonly observed in colorectal cancer are generally not known. The results in figure 8 demonstrate that one component of the T cells constituting the population of tumour infiltrating lymphocytes in this patients tumour is specific for a frameshift mutation, demonstrating that TGFβRII frameshift peptides are immunogenic *in vivo*, occasionally giving rise to spontaneous T cell activation.

3) It follows from this observation that processing of the non-functional form of the TGFβRII Receptor that is formed by the common frameshift mutation is processed. This processing may take place either in the tumour cell as part of natural breakdown of the aberrant protein, or after the tumour cell itself or a released form of the receptor has been taken up by a professional APC or both.

4) The results in Figure 8 also indicate that the peptide with seq. id. no. 17 is capable of binding to an HLA class II molecule, since pulsing of APC with this peptide results in a specific proliferative response against the peptide, and since CD4 T cell responses always are class II restricted. That this is the case is demonstrated by the results of the experiment shown in Figure 9. Here it is shown that the specific response against the peptide with seq. id. no. 17 is completely blocked by an antibody to HLA-DR, but not with antibodies to the two other HLA class II molecules, HLA-DQ and -DP. Furthermore, by using a panel of standard homozygous Epstein Barr Virus (EBV) transformed B Cell Lines (BCL) covering the relevant HLA class II molecules present on the patients own APC, we were able to identify the class II molecule responsible for presentation of the peptide with seq. id. no. 17 to TLC IMT8 and IMT9 as being HLA-DR 14. Together these findings fit extremely well with the immunohistological observations made in parallel sections taken from the same tumour biopsy, where we could show that activated CD4+ T cells were abundant in the proximity of tumour cells that had been induced to express HLA-DR molecules. The results in Figure 11 demonstrate that these T cell clones are capable of mounting a proliferative response over a range of peptide doses and that the responses are dose dependent.

5) Since these T cell clones were obtained by cloning T cells isolated from a tumour biopsy, another implication of our finding is that activated T cells specific for the peptide with seq. id. no. 17 are capable of homing to the tumour tissue after activation.

6) Since the peptide with seq. id. no. 17 is a tumour specific antigen, and since frameshift mutations giving rise to this peptide or peptides with overlapping sequences are commonly found in cancers with defects in enzymes that are part of the mismatch repair machinery, this peptide may be used as a vaccine to elicit T cell response in cancer patients or patients at high risk for developing cancer. Such T cell responses may potentially influence the growth of an existing tumour or prohibit regrowth of tumour after surgery and other forms of treatment or be given to patients with an inheritable form of cancer where a defect mismatch enzyme is detected or suspected and that have a high chance of developing a cancer where this precise mismatch repair mutation will occur.

Synthesis

The peptides were synthesised by using continuous flow solid phase peptide synthesis. N-a-Fmoc-amino acids with appropriate side chain protection were used. The Fmoc-amino acids were activated for coupling as pentafluorophenyl esters or by using either TBTU or diisopropyl carbodiimide activation prior to coupling. 20% piperidine in DMF was used for selective removal of Fmoc after each coupling. Cleavage from the resin and final removal of side chain protection was performed by 95% TFA containing appropriate scavengers. The peptides were purified and analysed by reversed phase (C18) HPLC. The identity of the peptides was confirmed by using electro-spray mass spectroscopy (Finnigan mat SSQ710).

The peptides used for *in vitro* studies of T cell stimulation were synthesised by this method.

Several other well known methods can be applied by a person skilled in the art to synthesise the peptides.

Examples of the method for determining new frameshift mutation peptides.

In this Example, the BAX gene is used to illustrate the principle.

CERTIFICATE OF CORRECTION (continued)
U.S. Pat. No. 7,192,927 B2

In each of the steps listed below, the 1st line is the gene sequence and 2nd line is amino acid sequence.

In the steps 2-5, the outlined sequences represent the mutant part of the protein.

```
Step one:

Normal BAX.

ATG GGG GGG GAG GCA CCC GAG CTG GCC CTG GAC CCG GTG .....
 M   G   G   E   A   P   E   L   A   L   D   P   V ...

Step two:

1G deleted from gene sequence.

ATG GGG GGG AGG CAC CCG AGC TGG CCC TGG ACC CGG TGC CTC
 M   G   G   R   H   P   S   W   P   W   T   R   C   L

AGG ATG CGT CCA CCA AGA AGC TGA
 R   M   R   P   P   R   S  stop

Step three:

2G deleted from gene sequence.

ATG GGG     GGA GGC ACC CGA GCT GGC CCT GGA CCC GGT GCC
 M   G       G   G   T   R   A   G   P   G   P   G   A

TCA GGA TGC GTC CAC CAA GAA GCT GAG CGA GTG TCT CAA GCG
 S   G   C   V   H   Q   E   A   E   R   V   S   Q   A

CAT CGG GGA CGA ACT GGA CAG TAA
 H   R   G   R   T   G   Q  stop
```

Step four:

1G inserted in gene sequence.

ATG GGG GGG *GGA* GGC ACC CGA GCT GGC CCT GGA CCC GGT GCC
M    G    G    G    G    T    R    A    G    P    G    P    G    A

TCA GGA TGC GTC CAC CAA GAA GCT GAG CGA GTG TCT CAA GCG
S    G    C    V    H    Q    E    A    E    R    V    S    Q    A

CAT CGG GGA CGA ACT GGA CAG *TAA*
H    R    G    R    T    G    Q    stop

Step five:

2G inserted in gene sequence.

ATG GGG GGG GGG *AGG* CAC CCG AGC TGG CCC TGG ACC CGG TGC
M    G    G    G    R    H    P    S    W    P    W    T    R    C

CTC AGG ATG CGT CCA CCA AGA AGC *TGA*
L    R    M    R    P    P    R    S    stop In the next Example, the TGFβRII gene is used to illustrate the principle.

In each of the steps listed below, the 1st line is the gene sequence and 2nd line is amino acid sequence.
In the steps 2-5, the outlined sequences represent the mutant part of the protein.

Step one:

Normal TGFβRII.

<u>GAA AAA AAA AA</u>G CCT GGT GAG ACT TTC TTC ATG TGT TCC....
E    K    K    K    P    G    E    T    F    F    M    C    S...

Step two:

1A deleted from gene sequence.

<u>GAA AAA AAA AGC</u> CTG GTG AGA CTT TCT TCA TGT GTT CCT GTA
E   K   K   S   L   V   R   L   S   S   C   V   P   V

GCT CTG ATG AGT GCA ATG ACA ACA TCA TCT TCT CAG AAG AAT
A   L   M   S   A   M   T   T   S   S   S   Q   K   N

ATA ACA CCA GCA ATC CTG ACT TGT TGC <u>TAG</u>
I   T   P   A   I   L   T   C   C   stop Step three:

2A deleted from gene sequence.

<u>GAA AAA AAA</u> GCC TGG <u>TGA</u>
E   K   K   A   W   stop

Step four:

1A inserted in gene sequence.

<u>GAA AAA AAA AAA</u> GCC TGG <u>TGA</u>
E   K   K   K   A   W   stop

Step five:

2A inserted in gene sequence.

<u>GAA AAA AAA AAA</u> AGC CTG GTG AGA CTT TCT TCA TGT GTT CCT
E   K   K   K   S   L   V   R   L   S   S   C   V   P

GTA GCT CTG ATG AGT GCA ATG ACA ACA TCA TCT TCT CAG AAG
V   A   L   M   S   A   M   T   T   S   S   S   Q   K

AAT ATA ACA CCA GCA ATC CTG ACT TGT TGC <u>TAG</u>
N   I   T   P   A   I   L   T   C   C   stop Thus the peptides of the invention may be used in a method for the treatment of cancers with cancer cells harbouring genes with frameshift mutations, which treatment comprises administering at least one peptide of the present invention *in vivo* or *ex vivo* to a human patient in need of such treatment.

In another embodiment the peptides of the invention may be used to vaccinate a human being disposed for cancers with cancer cells harbouring genes with frameshift mutations, by administering at least one peptide of the present invention to said human being.

It is further considered to be an advantage to administer to a human individual a mixture of the peptides of this invention, whereby each of the peptides of the invention can bind to different types of HLA class I and/or class II molecules of the individual.

It is further anticipated that the power of an anticancer vaccine or peptide drug as disclosed in the above mentioned PCT/NO92/00032 application, can be greatly enhanced if the peptides of the present invention were included. Thus in another embodiment of the present invention peptides of the present invention are administered together with, either simultaneously or in optional sequence, with the peptides disclosed in PCT/NO92/00032.

It is considered that the peptides may be administered together, either simultaneously or separately, with compounds such as cytokines and/or growth factors, i.e. interleukin-2 (IL-2), interleukin-12 (IL-12), granulocyte macrophage colony stimulating factor (GM-CSF), Flt-3 ligand or the like in order to strengthen the immune response as known in the art.

The peptides according to the present invention can be used in a vaccine or a therapeutical composition either alone or in combination with other materials, such as for instance standard adjuvants or in the form of a lipopeptide conjugate which as known in the art can induce high-affinity cytotoxic T lymphocytes, (K. Deres, Nature, Vol. 342, (Nov. 1989)).

The peptides according to the present invention may be useful to include in either a peptide or recombinant fragment based vaccine.

The peptides according to the present invention can be included in pharmaceutical compositions or in vaccines together with usual additives, diluents, stabilisers or the like as known in the art.

According to this invention, a pharmaceutical composition or vaccine may include the peptides alone or in combination with at least one pharmaceutically acceptable carrier or diluent.

Further a vaccine or therapeutical composition can comprise a selection of peptides which are fragments of the mutant proteins arising from insertion or deletion of bases in a repeat sequence of the gene.

Further a vaccine composition can comprise at least one peptide selected for one cancer, which vaccine would be administered to a person carrying a genetic disposition for this particular cancer.

Further a vaccine composition can comprise at least one peptide selected for one cancer, which vaccine would be administered to a person belonging to a high risk group for this particular cancer.

The cancer vaccine according to this invention may further be administered to the population in general for example as a mixture of peptides giving rise to T cell immunity against various common cancers connected with frameshift mutation genes.

The peptides according to this invention may be administered as single peptides or as a mixture of peptides. Alternatively the peptides may be covalently linked with each other to form larger polypeptides or even cyclic polypeptides.

A cancer therapy according to the present invention may be administered both in vivo or ex vivo having as the main goal the raising of specific T cell lines or clones against the mutant gene product associated with the cancer type with which the patient is afflicted.

Further, the frameshift mutant peptides of this invention may be administered to a patient by various routes including but not limited to subcutaneous, intramuscular, intradermal, intraperitoneal, intravenous or the like. In one embodiment the peptides of this invention are administered intradermally. The peptides may be administered at single or multiple injection sites to a patient in a therapeutically or prophylactically effective amount.

The peptides of this invention may be administered only once or alternatively several times, for instance once a week over a period of 1-2 months with a repeated sequence later all according to the need of the patient being treated.

The peptides of this invention can be administered in an amount in the range of 1 microgram (1 µg) to 1 gram (1g) to an average human patient or individual to be vaccinated. It is preferred to use a smaller dose in the range of 1 microgram (1 µg) to 1 milligram (1 mg) for each administration.

The invention further encompasses DNA sequences which encodes a frameshift mutation peptide.

The invention additionally encompasses isolated DNA sequences comprising a DNA sequence encoding at least one frameshift mutant peptide, and administration of such isolated DNA sequences as a vaccine for treatment or prophylaxis of cancers associated with frameshift mutations in the genes.

The peptides according to this invention may be administered to an individual in the form of DNA vaccines. The DNA encoding these peptides may be in the form of cloned plasmid DNA or synthetic oligonucleotide. The DNA may be delivered together with cytokines, such as IL-2, and/or other co-stimulatory molecules. The cytokines and/or co-stimulatory molecules may themselves be delivered in the form of plasmid or oligonucleotide DNA. The response to a DNA vaccine has been shown to be increased by the presence of immunostimulatory DNA sequences (ISS). These can take the form of hexameric motifs containing methylated CpG, according to the formula: 5'-purine-purine-CG-pyrimidine-pyrimidine-3'. Our DNA vaccines may therefore incorporate these or other ISS, in the DNA encoding the peptides, in the DNA encoding the cytokine or other co-stimulatory molecules, or in both. A review of the advantages of DNA vaccination is provided by Tighe et al (1998, *Immunology Today*, 19(2), 89-97).

In one embodiment, the DNA sequence encoding the mutant BAX peptides comprises:

```
Normal BAX.

ATG GGG GGG GAG GCA CCC GAG CTG GCC CTG GAC CCG GTG .....

1G deleted from BAX gene sequence.

ATG GGG GGG AGG CAC CCG AGC TGG CCC TGG ACC CGG TGC CTC

AGG ATG CGT CCA CCA AGA AGC TGA 2G deleted from BAX gene sequence.

ATG GGG  GGA GGC ACC CGA GCT GGC CCT GGA CCC GGT GCC

TCA GGA TGC GTC CAC CAA GAA GCT GAG CGA GTG TCT CAA GCG

CAT CGG GGA CGA ACT GGA CAG TAA 1G inserted in BAX gene sequence.

ATG GGG GGG GGA GGC ACC CGA GCT GGC CCT GGA CCC GGT GCC

TCA GGA TGC GTC CAC CAA GAA GCT GAG CGA GTG TCT CAA GCG

CAT CGG GGA CGA ACT GGA CAG TAA 2G inserted in BAX gene sequence.
ATG GGG GGG GGG AGG CAC CCG AGC TGG CCC TGG ACC CGG TGC

CTC AGG ATG CGT CCA CCA AGA AGC TGA
```

In a second embodiment, the DNA sequence encoding the mutant TGFβRII peptides comprises:

```
Normal TGFβRII gene.

GAA AAA AAA AAG CCT GGT GAG ACT TTC TTC ATG TGT TCC....

1A deleted from TGFβRII gene sequence.

GAA AAA AAA AGC CTG GTG AGA CTT TCT TCA TGT GTT CCT GTA

GCT CTG ATG AGT GCA ATG ACA ACA TCA TCT TCT CAG AAG AAT